United States Patent
Hutchison et al.

(10) Patent No.: US 7,253,168 B2
(45) Date of Patent: Aug. 7, 2007

(54) SUBSTITUTED 1-BENZYL-4-SUBSTITUTED PIPERAZINE ANALOGUES

(75) Inventors: Alan J. Hutchison, Madison, CT (US); Bertrand L. Chenard, Waterford, CT (US); James G. Tarrant, Hamden, CT (US); Guiying Li, Branford, CT (US); Manuka Ghosh, Madison, CT (US); George P. Luke, Clinton, CT (US); John M. Peterson, Durham, CT (US); Wallace C. Pringle, Guilford, CT (US); Mary-Margaret E. O'Donnell, Shelton, CT (US); Kyungae Lee, Newton, MA (US); Linda M. Gustavson, Ringoes, NJ (US); Dario Doller, Wallingford, CT (US)

(73) Assignee: Neurogen Corporation, Branford, CT (US)

(*) Notice: Subject to any disclaimer, the term of this patent is extended or adjusted under 35 U.S.C. 154(b) by 0 days.

(21) Appl. No.: 11/100,355

(22) Filed: Apr. 6, 2005

(65) Prior Publication Data

US 2006/0142301 A1 Jun. 29, 2006

Related U.S. Application Data

(60) Provisional application No. 60/560,417, filed on Apr. 7, 2004.

(51) Int. Cl.
- A07D 241/36 (2006.01)
- A61K 31/498 (2006.01)
- A61P 3/04 (2006.01)
- A61P 3/10 (2006.01)
- C07D 239/70 (2006.01)
- C07D 487/08 (2006.01)
- C07D 471/14 (2006.01)
- A61K 31/517 (2006.01)
- A61K 31/407 (2006.01)

(52) U.S. Cl. ........ 514/249; 544/349; 544/253; 544/355; 544/238; 544/295; 544/357; 548/453; 514/256; 514/414; 514/314; 514/338; 514/252.11; 514/307; 514/252.02; 546/168; 546/276.7; 546/146

(58) Field of Classification Search .......... 544/349, 544/238, 295; 514/249, 252.02
See application file for complete search history.

(56) References Cited

U.S. PATENT DOCUMENTS

| | | | |
|---|---|---|---|
| 4,140,775 A | 2/1979 | McCall | |
| 4,370,329 A | 1/1983 | Scherm et al. | |
| 4,370,330 A | 1/1983 | Scherm et al. | |
| 4,414,389 A | 11/1983 | Freed | |
| 4,616,086 A | 10/1986 | Witte et al. | |
| 4,673,675 A | 6/1987 | Robba et al. | |
| 4,704,382 A | 11/1987 | Chorvat et al. | |
| 4,806,536 A | 2/1989 | Cross et al. | |
| 4,868,194 A | 9/1989 | Carr et al. | |
| 4,921,863 A | 5/1990 | Sugimoto et al. | |
| 4,937,246 A | 6/1990 | Sugihara et al. | |
| 5,179,095 A | 1/1993 | Oinuma et al. | |
| 5,569,659 A | 10/1996 | Reitz | |
| 5,652,242 A | 7/1997 | Wayne et al. | |
| 5,681,954 A | 10/1997 | Yamamoto et al. | |
| 5,688,798 A | 11/1997 | Godel et al. | |
| 5,753,659 A | 5/1998 | Mills | |
| 5,859,246 A | 1/1999 | Thurkauf et al. | |
| 5,869,488 A | 2/1999 | Shue et al. | |
| 5,883,096 A | 3/1999 | Lowe et al. | |
| 5,965,560 A | 10/1999 | Glase et al. | |

(Continued)

FOREIGN PATENT DOCUMENTS

| | | |
|---|---|---|
| EP | 0390654 A1 | 10/1990 |
| EP | 0624584 B1 | 11/1994 |
| GB | 1378964 | 1/1975 |
| JP | 2002-322163 | 11/2002 |

(Continued)

OTHER PUBLICATIONS

J.R. Boissier et al., "Synthesis and Pharmacological Study of New Piperazine Derivatives", Sep. 1963, pp. 551-554.

(Continued)

Primary Examiner—Mark L. Berch
Assistant Examiner—Susanna Moore
(74) Attorney, Agent, or Firm—Cantor Colburn LLP

(57) ABSTRACT

Compounds of Formula I are provided, in which variables are as described herein:

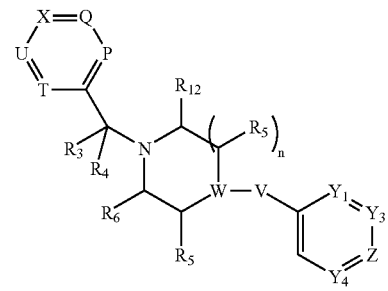

Such compounds may be used to modulate MCH binding to MCH receptors in vivo or in vitro, and are particularly useful in the treatment of a variety of metabolic, feeding and sexual disorders in humans, domesticated companion animals and livestock animals. Pharmaceutical compositions and methods for treating such disorders are provided, as are methods for using such ligands for detecting MCH receptors (e.g., receptor localization studies).

26 Claims, No Drawings

U.S. PATENT DOCUMENTS

| | | | |
|---|---|---|---|
| 6,048,876 | A | 4/2000 | Annoura et al. |
| 6,057,371 | A | 5/2000 | Glennon et al. |
| 6,121,267 | A | 9/2000 | Glase et al. |
| 6,172,229 | B1 | 1/2001 | Thurkauf et al. |
| 6,200,986 | B1 | 3/2001 | Bhatnagar et al. |
| 6,251,893 | B1 | 6/2001 | Maddaford et al. |
| 6,313,127 | B1 | 11/2001 | Waterson et al. |
| 6,414,149 | B1 | 7/2002 | Chu-Moyer et al. |
| 6,455,528 | B1 | 9/2002 | Adachi et al. |
| 6,479,495 | B1 | 11/2002 | Kosley, Jr. et al. |
| 6,518,273 | B1 | 2/2003 | Chapman et al. |
| 6,541,477 | B2 | 4/2003 | Lewicki et al. |
| 6,569,861 | B2 | 5/2003 | Bakthavatchalam et al. |
| 6,753,336 | B2 | 6/2004 | Bakthavatchalam et al. |
| 2001/0039286 | A1 | 11/2001 | Dinnell et al. |
| 2001/0049367 | A1 | 12/2001 | Bennani et al. |
| 2002/0065278 | A1 | 5/2002 | Apodaca et al. |
| 2003/0018034 | A1 | 1/2003 | Adachi et al. |
| 2003/0055064 | A1 | 3/2003 | Adachi et al. |
| 2003/0207882 | A1 | 11/2003 | Stocker et al. |
| 2003/0220324 | A1 | 11/2003 | Fotsch et al. |
| 2004/0229883 | A1 | 11/2004 | Bakthavatchalam et al. |
| 2005/0065162 | A1 | 3/2005 | Hutchison et al. |

FOREIGN PATENT DOCUMENTS

| | | |
|---|---|---|
| JP | 2004-256526 A | 9/2004 |
| WO | 9316057 | 8/1993 |
| WO | WO 97/44334 | 11/1997 |
| WO | WO 99/16746 | 4/1999 |
| WO | WO 99/65906 | 12/1999 |
| WO | WO 01/17965 A2 | 3/2001 |
| WO | WO 01-36386 A1 | 5/2001 |
| WO | WO 01/64676 A2 | 9/2001 |
| WO | WO 02/051809 A1 | 7/2002 |
| WO | 02094799 A2 | 11/2002 |
| WO | WO 2004/035556 A1 | 4/2004 |
| WO | WO 2004/037800 A1 | 5/2004 |
| WO | 2005110989 A1 | 11/2005 |
| WO | 2005110989 A1 | 1/2007 |

OTHER PUBLICATIONS

Tokushi Hanano et al.; "Novel DMARDs on the Basis of a New Concept of Dual Cytokine Regulation, TNF-x Suppression and IL-10 Augmentation", Bioorganic & Medicinal Chemistry Letters 10 (2000) pp. 881-884.

Dina Manetti et al., "Hybridized and Isosteric Analogues of N1-Acetyl-N4—dimethyl-piperazinium Iodide (ADMP) and N1-Phenyl-N4—dimethyl-piperazinium Iodide (DMPP) with Central Nicotinic Action", Bioorganic & Medicinal Chemistry 7 (1999) pp. 457-465.

International Search Report for co-owned Application No. PCT/US2005/011890, mailed Jul. 11, 2005.

Premilla N. Arasasingham, et al., "Structure-Activity Relationship of (1-Aryl-2-piperazinylethyl) piperazines: Antagonists for the AGRP/Melanocortin Receptor Binding", J. Med. Chem. (2003) 46: 9-11.

Kje-Kee Kim et al., "Synthesis and Biological Evaluation of 3-(4-substituted-phenyl)-$N$-hydroxy-2-propenamides, a new Class of Histone Deacetylase Inhibitors", J. Med. Chem. (2003) 46: 5745-5751.

Marc Nazare et al., "Novel factor Xa inhibitors based on a benzoic acid scaffold and incorporating a neutral P1 ligand", Bioorganic & Medicinal Chemistry Letters (2004) 14: 2801-2805.

Ning Xi et al., "Synthesis of novel melanocortin 4 receptor agonists and antagonists containing a succinamide core", Bioorganic & Medicinal Chemistry Letters (2004) 14: 377-381.

International Search Report for International Application No.: PCT/US2005/011896, Mailed Dec. 12, 2005.

Carpenter, A. J. and D. L. Hertzog "Melanin-Concentrating Hormone Receptor Antagonists as Potential Antiobesity Agents," Expert Opin. Ther. Patents (2002) 12(11): 1639-1646.

Gilbert, A. M. et al "Modulation of Selective Serotonin Reuptake Inhibitor and 5-HTIA Antagonist Activity in 8-aza-bicyclo[3.2.1]octane Derivatives of 2,3-dihydro-1,4-benzodioxane," Bioorganic and Medicinal Chemistry Letters (2004) 14: 515-518.

Saleh, M. A. et al. "The Synthesis of 2,7-Substituted Octahydro-2H-Pyrido[1,2-a] Pyrazines, Analogues of Quinolizidine and Piperazine Drugs," Tetrahedron (1994) 50(6): 1811-1820.

Written Opinion of the International Searching Authority for International Application No. PCT/US2005/021340. Mailed Oct. 31, 2006.

Written Opinion of the International Searching Authority for International Application No. PCT/2005/011890. Mailed Jul. 11, 2005.

SUBSTITUTED 1-BENZYL-4-SUBSTITUTED PIPERAZINE ANALOGUES

CROSS REFERENCE TO RELATED APPLICATIONS

This application claims priority from U.S. Provisional Patent Application No. 60/560,417, filed Apr. 7, 2004, which is hereby incorporated by reference in its entirety.

FIELD OF THE INVENTION

This invention relates generally to substituted 1-benzyl-4-substituted piperazine analogues. The invention further relates to the use of such compounds for treating a variety of metabolic, eating and sexual disorders, and as probes for the detection and localization of melanin concentrating hormone receptors.

BACKGROUND OF THE INVENTION

Melanin concentrating hormone, or MCH, is a cyclic 19 amino acid neuropeptide first identified as a regulator of skin coloration in fish and other vertebrates, and subsequently as a regulator of food intake and energy balance in higher vertebrates. In many species, including humans, MCH is produced in the hypothalamus. MCH is also produced at various peripheral sites, including the gastrointestinal tract and testis.

The postulated role of MCH in feeding behavior and body weight regulation is confirmed by the finding that i.c.v. injection of MCH increases caloric consumption in rats over similarly treated control animals. Furthermore, rats having the ob/ob genotype exhibit a 50-80% increase in MCH mRNA expression as compared to leaner ob/+ genotype mice, and prepro-MCH knockout mice, as well as MCH receptor knockout mice, are leaner than normal mice, due to hypophagia and an increased metabolic rate.

MCH activity is mediated via binding to specific receptors. Like other G protein-coupled receptors (e.g., neuropeptide Y and beta-adrenergic receptors), MCH receptors are membrane-spanning proteins that are generally found on cell surfaces, and consist of a single contiguous amino acid chain comprising an extracellular N-terminal domain, seven membrane-spanning alpha helical domains (connected by three intracellular loop domains alternating with three extracellular loop domains), and an intracellular C-terminal domain. Signal transduction is typically initiated by the binding of extracellular MCH to the receptor, which elicits conformational changes in the extracellular domains. When the receptor is functioning properly, these conformational changes propagate through the transmembrane domains and result in a coordinated change in the intracellular portions of the receptor. This precise alteration in the intracellular domains acts to trigger the associated G-protein complex to modulate intracellular signaling.

Human Melanin Concentrating Hormone Receptor-1 (MCH1R) is a 353 amino acid, 7-transmembrane, alpha-helical, G protein-coupled receptor, initially reported as orphan receptor SLC-1. Immunohistochemistry studies of rat brain sections indicate that MCH1R is widely expressed in brain. MCH1R expression is found in olfactory tubercle, cerebral cortex, substantia nigra, basal forebrain CA1, CA2, and CA3 fields of the hippocampus, amygdala, and in nuclei of the hypothalamus, thalamus, midbrain and hindbrain. Strong signals are observed in the ventromedial and dorsomedial nuclei of the hypothalamus, two areas of the brain involved in feeding behavior. Upon binding MCH, MCH1R recombinantly expressed in HEK 293 cells mediates a dose dependent release of intracellular calcium. Cells expressing MCH1R also exhibit a pertussis toxin sensitive dose-dependent inhibition of forskolin-elevated cyclic AMP, indicating that the receptor couples to a $G_{i/o}$ G-protein alpha subunit. Certain monkey and human MCH1R sequences, as well as various chimeric MCH1R proteins, have been disclosed in U.S. patent application Ser. No. 10/309,515 (published as 2003/0114644 on Jun. 19, 2003).

A second MCH receptor (designated MCH2R) has also been identified. MCH2R has an overall amino acid identity of more than 30% with MCH1R, and is detected specifically in the same regions of the brain as MCH1R. Monkey and canine MCH2R sequences, as well as various chimeric MCH2R proteins, have been disclosed in U.S. patent application Ser. No. 10/291,990 (which published as 2003/0148457 on Aug. 7, 2003).

Agents capable of modulating MCH receptor activity are highly desirable for the treatment of a variety of diseases and disorders, including obesity, eating disorders (e.g., bulimia and anorexia), sexual disorders (e.g., anorgasmic or psychogenic impotence) and metabolic disorders, such as diabetes. Small molecule, non-peptide antagonists of MCH receptors would be of particular value for such therapies. The present invention fulfills this need, and provides further related advantages.

SUMMARY OF THE INVENTION

The present invention provides compounds of Formula I, including pharmaceutically acceptable salts thereof:

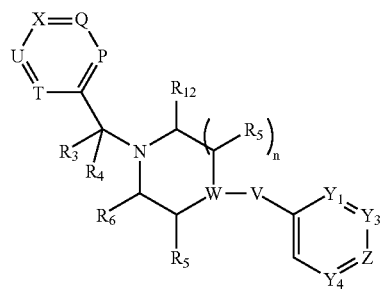

Formula I

Within Formula I:

V is absent or —(C=O)—.

W is nitrogen, CH, C—CN or C—OH.

$Y_1$, $Y_3$ and $Y_4$ are independently $CR_1$ or nitrogen, and Z is nitrogen or $CR_2$; in certain embodiments at least one of $Y_3$, $Y_4$ and Z is nitrogen.

Each $R_1$ is independently:
  (i) hydrogen, halogen, hydroxy, nitro, cyano, amino, $C_1$-$C_6$alkyl, $C_2$-$C_6$alkenyl, $C_2$-$C_6$alkynyl, $C_1$-$C_6$alkoxy, halo$C_1$-$C_6$alkyl, halo$C_1$-$C_6$alkoxy, amino$C_1$-$C_6$alkyl, mono- or di-($C_1$-$C_6$alkyl)amino$C_0$-$C_6$alkyl, ($C_3$-$C_7$cycloalkyl)$C_0$-$C_6$alkyl or (3- to 7-membered heterocycloalkyl)$C_0$-$C_6$alkyl; or
  (ii) taken together with $R_2$ to form a fused 5- or 6-membered carbocycle or heterocycle, each of which is substituted with from 0 to 3 substituents independently chosen from halogen, hydroxy, nitro, cyano, amino, $C_1$-$C_4$alkyl, $C_1$-$C_4$alkoxy, halo$C_1$-$C_4$alkyl and halo$C_1$-$C_4$alkoxy.

$R_2$ is hydrogen, halogen, nitro, cyano, amino, acetyl, carboxamide, imino, $C_1$-$C_6$alkyl, $C_2$-$C_6$alkenyl, $C_2$-$C_6$alkynyl, $C_2$-$C_6$alkanoyl, $C_2$-$C_6$alkyloxime, $C_1$-$C_6$alkoxy, ($C_1$-$C_6$alkoxy)$C_1$-$C_4$alkyl, hydroxy$C_1$-$C_6$alkyl, $C_1$-$C_6$alkoxycarbonyl, mono- or di-alkylcarboxamide, $C_1$-$C_6$alkylthio, $C_1$-$C_6$alkylsulfonyl, halo$C_1$-$C_6$alkyl, halo$C_1$-$C_6$alkoxy, amino$C_1$-$C_6$alkyl, mono- or di-($C_1$-$C_6$alkyl)amino$C_0$-$C_6$alkyl or ($C_3$-$C_7$cycloalkyl)$C_0$-$C_6$alkyl, or $R_2$ is (3- to 7-membered heterocycloalkyl)$C_0$-$C_6$alkyl, phenyl$C_0$-$C_2$alkyl, phenyl$C_1$-$C_2$alkoxy or heteroaryl$C_0$-$C_2$alkyl, each of which is substituted with 0 to 3 substituents independently chosen from halogen, $C_1$-$C_2$alkoxy and $C_1$-$C_2$alkyl; or $R_2$ is taken together with a $R_1$ to form a fused 5- or 6-membered carbocycle or heterocycle, each of which is substituted with from 0 to 3 substituents independently chosen from halogen, hydroxy, nitro, cyano, amino, $C_1$-$C_4$alkyl, $C_1$-$C_4$alkoxy, halo$C_1$-$C_4$alkyl and halo$C_1$-$C_4$alkoxy.

The variable n is 1 or 2.

$R_3$ is: (i) hydrogen, $C_1$-$C_6$alkyl, $C_2$-$C_6$alkenyl or halo$C_1$-$C_6$alkyl; or (ii) taken together with one or both of $R_6$ and $R_{10}$ to form a fused carbocycle or heterocycle having one or two rings, wherein each ring contains from 5 to 8 ring members and 0, 1 or 2 heteroatoms.

$R_4$ is hydrogen, $C_1$-$C_6$alkyl or halo$C_1$-$C_6$alkyl.

Each $R_5$ is independently: (i) hydrogen, halogen, hydroxy, nitro, cyano, amino, $C_1$-$C_6$alkyl, $C_2$-$C_6$alkenyl, $C_2$-$C_6$alkynyl, $C_1$-$C_6$alkoxy, halo$C_1$-$C_6$alkyl, halo$C_1$-$C_6$alkoxy, mono- or di-($C_1$-$C_6$alkyl)amino or amino$C_1$-$C_6$alkyl; or (ii) taken together with $R_6$ to form a 5- to 8-membered carbocycle or heterocycle or a methylene or ethylene bridge.

$R_6$ is: (i) hydrogen, halogen, hydroxy, nitro, cyano, amino, $C_1$-$C_6$alkyl, $C_2$-$C_6$alkenyl, $C_2$-$C_6$alkynyl, $C_1$-$C_6$alkoxy, halo$C_1$-$C_6$alkyl, halo$C_1$-$C_6$alkoxy, mono- or di-($C_1$-$C_6$alkyl)amino, or amino$C_1$-$C_6$alkyl; (ii) taken together with $R_3$ form a fused carbocycle or heterocycle; or (iii) taken together with $R_5$ to form a fused carbocycle or heterocycle or a methylene or ethylene bridge.

P is N or $CR_7$; Q is N or $CR_8$; U is N or $CR_9$; T is N or $CR_{10}$; and X is N or $CR_{11}$.

$R_7$ is: (i) hydrogen, halogen, hydroxy, nitro, cyano, —COOH or a group of the formula L-M; or (ii) taken together with $R_8$ or $R_{12}$ to form a fused 5- or 6-membered carbocycle or heterocycle.

$R_8$ is: (i) hydrogen, halogen, hydroxy, nitro, cyano, —COOH or a group of the formula L-M; or (ii) taken together with $R_7$ to form a fused 5- or 6-membered carbocycle or heterocycle.

$R_9$ is: (i) hydrogen, halogen, hydroxy, nitro, cyano, —COOH or a group of the formula L-M; or (ii) taken together with $R_{10}$ or $R_{11}$ to form a fused 5- to 10-membered carbocycle or heterocycle.

$R_{10}$ is: (i) hydrogen, halogen, hydroxy, nitro, cyano, —COOH or a group of the formula L-M; or (ii) taken together with $R_3$ or $R_9$ to form a fused carbocycle or heterocycle.

$R_{11}$ is: (i) hydrogen, halogen, hydroxy, nitro, cyano, —COOH or a group of the formula L-M; or (ii) taken together with $R_9$ to form a fused carbocycle or heterocycle.

$R_{12}$ is: (i) hydrogen, halogen, hydroxy, nitro, cyano, amino, $C_1$-$C_6$alkyl, $C_2$-$C_6$alkenyl, $C_2$-$C_6$alkynyl, $C_1$-$C_6$alkoxy, halo$C_1$-$C_6$alkyl, halo$C_1$-$C_6$alkoxy, mono- or di-($C_1$-$C_6$alkyl)amino or amino$C_1$-$C_6$alkyl; or (ii) taken together with $R_7$ to form a fused carbocycle or heterocycle.

Each L is independently a single covalent bond, $N(R_{13})$

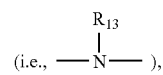

O, C(=O)

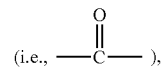

$SO_2$, $SO_2NH$

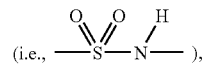

$C(=O)N(R_{13})$

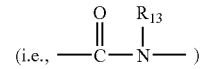

or $N(R_{13})C(=O)$

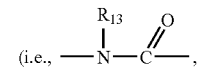

wherein each $R_{13}$ is independently hydrogen, $C_1$-$C_6$alkyl, $C_2$-$C_6$alkenyl, $C_2$-$C_6$alkynyl or halo$C_1$-$C_6$alkyl; and Each M is independently hydrogen, $C_1$-$C_6$alkyl, $C_2$-$C_6$alkenyl, $C_2$-$C_6$alkynyl, halo$C_1$-$C_6$alkyl, amino$C_1$-$C_6$alkyl or a 5- to 10-membered cycloalkyl or heterocycloalkyl; preferably M is not hydrogen if L is a single covalent bond.

Within certain aspects, compounds as described herein (i.e., a compound of Formula I or a pharmaceutically acceptable salt thereof) are MCH receptor modulators and exhibit a $K_i$ of no greater than 1 micromolar, 500 nanomolar, 100 nanomolar, or 10 nanomolar in a MCH receptor binding assay and/or have an $EC_{50}$ or $IC_{50}$ value of no greater than 1 micromolar, 500 nanomolar, 100 nanomolar, or 10 nanomolar in an assay for determining MCH receptor agonist or antagonist activity.

Within certain aspects, compounds as described herein are labeled with a detectable marker (e.g., radiolabeled or fluorescein conjugated).

The present invention further provides, within other aspects, pharmaceutical compositions comprising at least one compound as described herein in combination with a physiologically acceptable carrier or excipient. Within certain embodiments, a pharmaceutical composition provided herein may further comprise one or more additional active agents (i.e., drugs). Pharmaceutical compositions provided herein may be formulated, for example, as an injectable fluid, an aerosol, a cream, a gel, a pill, a capsule, a syrup, or a transdermal patch.

The present invention further provides, within other aspects, methods for treating a disease or disorder associated with MCH receptor activation, comprising administering to a patient in need of such treatment a therapeutically effective amount of a MCH receptor modulator as described above. Such diseases and disorders include, for example, eating disorders (e.g., obesity and bulimia nervosa), sexual disorders, diabetes, heart disease, and stroke. The MCH receptor modulator may be administered orally, or via another means such as intranasally, intravenously, or topically. Within certain embodiments, the patient is a human, companion animal, or livestock animal.

Methods are provided, within other aspects, for determining the presence or absence of MCH receptor in a sample, comprising: contacting a sample with a compound as described above under conditions that permit binding of the compound to MCH receptor; and detecting a level of the compound bound to MCH receptor. Within certain embodiments, the compound is radiolabeled, and the step of detection comprises: separating unbound compound from bound compound; and determining an amount of bound compound in the sample. Detection may be achieved, for example, using autoradiography.

The present invention further provides, within other aspects, methods for modulating binding of ligand to MCH receptor. Certain such methods are performed in vitro, and comprise contacting MCH receptor with MCH receptor modulator as described above, under conditions and in an amount sufficient to detectably modulate MCH binding to MCH receptor. Other such methods may be performed in vivo, and comprise contacting cells expressing MCH receptor with a MCH receptor modulator as described above in an amount that is sufficient to detectably modulate MCH binding to cells expressing a cloned MCH receptor in vitro.

Methods are further provided for modulating binding of MCH to MCH receptor in a patient, comprising administering to a patient (i.e., a human or non-human animal) a MCH receptor modulator as described above. Patients include, for example, companion animals such as dogs.

Within further aspects, the present invention provides methods for modulating the signal-transducing activity of MCH receptor, comprising contacting an MCH receptor, either in vivo or in vitro, with an amount of an MCH receptor modulator sufficient to detectably alter MCH receptor activity, under conditions suitable for binding of MCH to MCH receptor. Preferably, the MCH receptor is a MCH1R.

Packaged pharmaceutical preparations, comprising: (a) a pharmaceutical composition as described above in a container; and (b) instructions for using the composition to treat a patient suffering from or at risk for developing a disease or disorder associated with MCH receptor activation. Such disorders include, for example eating disorders (e.g., obesity and bulimia nervosa), sexual disorders, diabetes, heart disease, and stroke, are also provided herein.

In yet another aspect, methods of preparing the compounds disclosed herein, including the intermediates, are also provided herein.

These and other aspects of the present invention will become apparent upon reference to the following detailed description.

DETAILED DESCRIPTION OF THE INVENTION

As noted above, the present invention provides substituted 1-benzyl-4-substituted piperazine analogues of Formula I. Certain such compounds are MCH receptor modulators that may be used in vitro or in vivo, to inhibit MCH binding to MCH receptors, activate MCH receptors, or to otherwise modulate MCH receptor activity in a variety of contexts, as discussed in further detail below.

Terminology

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Compound descriptions are intended to encompass compounds with all possible isotopes of atoms occurring in the compounds. Isotopes are those atoms having the same atomic number but different mass numbers. By way of general example, and without limitation, isotopes of hydrogen include tritium and deuterium and isotopes of carbon include $^{11}C$, $^{13}C$ and $^{14}C$. Certain compounds are described herein using a general formula that includes variables (e.g., X, V, $R_3$). Unless otherwise specified, each variable within such a formula is defined independently of any other variable, and any variable that occurs more than one time in a formula is defined independently at each occurrence. In general, the variables may have any definition described herein that results in a stable compound.

The term "substituted 1-benzyl-4-substituted piperazine analogues" as used herein, encompasses all compounds that satisfy Formula I, including any enantiomers, racemates and stereoisomers, as well as all pharmaceutically acceptable salts of such compounds.

A "pharmaceutically acceptable salt" of a compound recited herein is an acid or base salt that is suitable for use in contact with the tissues of human beings or animals without excessive toxicity carcinogenicity, and preferably without irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0-4, and the like. Similarly, pharmaceutically acceptable cations include, but are not limited to sodium, potassium, calcium, aluminum, lithium, and ammonium. Those of ordinary skill in the art will recognize further pharmaceutically acceptable salts for the compounds provided herein, including those listed by *Remington's Pharmaceutical Sciences,* 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of nonaqueous media, such as ether, ethyl acetate, ethanol, isopropanol, or acetonitrile, is preferred.

It will be apparent that each compound of Formula I may, but need not, be formulated as a hydrate, solvate or noncovalent complex. In addition, the various crystal forms and polymorphs are within the scope of the present invention. Also provided herein are prodrugs of the compounds of Formula I. A "prodrug" is a compound that may not fully satisfy the structural requirements of the compounds provided herein, but is modified in vivo, following administration to a patient, to produce a compound of Formula I. For example, a prodrug may be an acylated derivative of a compound as provided herein. Prodrugs include compounds wherein hydroxy, amine or sulfhydryl groups are bonded to any group that, when administered to a mammalian subject, cleaves to form a free hydroxyl, amino or sulfhydryl group, respectively. Examples of prodrugs include, but are not limited to, acetate, formate, phosphate and benzoate derivatives of alcohol and amine functional groups within the compounds provided herein. Prodrugs of the compounds provided herein may be prepared by modifying functional groups present in the compounds in such a way that the modifications are cleaved in vivo to yield the parent compounds.

"Acetyl" refers to a group of the formula —(C═O)CH$_3$.

As used herein, the term "alkyl" refers to a straight chain or branched chain saturated aliphatic hydrocarbon. An alkyl group may be bonded to an atom within a molecule of interest via any chemically suitable portion. Alkyl groups include groups having from 1 to 8 carbon atoms ($C_1$-$C_8$alkyl), from 1 to 6 carbon atoms ($C_1$-$C_6$alkyl) and from 1 to 4 carbon atoms ($C_1$-$C_4$alkyl), such as methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl. "$C_0$-$C_n$alkyl" refers to a single covalent bond ($C_0$) or an alkyl group having from 1 to n carbon atoms. For example "$C_0$-$C_6$alkyl" refers to a single covalent bond or a $C_1$-$C_6$alkyl group. The term "alkylene" refers to a divalent alkyl group.

Similarly, "alkenyl" refers to a straight or branched chain alkene group, in which at least one unsaturated carbon-carbon double bond is present. Alkenyl groups include $C_2$-$C_8$alkenyl, $C_2$-$C_6$alkenyl and $C_2$-$C_4$alkenyl groups, which have from 2 to 8, 2 to 6, or 2 to 4 carbon atoms, respectively, such as ethenyl, allyl or isopropenyl. "Alkynyl" refers to straight or branched chain alkyne groups, which have one or more unsaturated carbon-carbon bonds, at least one of which is a triple bond. Alkynyl groups include $C_2$-$C_8$alkynyl, $C_2$-$C_6$alkynyl and $C_2$-$C_4$alkynyl groups, which have from 2 to 8, 2 to 6, or 2 to 4 carbon atoms, respectively. Alkenyl and alkynyl groups may be straight or branched chain.

By "alkoxy," as used herein, is meant an alkyl group as described above attached via an oxygen bridge. Alkoxy groups include $C_1$-$C_8$alkoxy, $C_1$-$C_6$alkoxy and $C_1$-$C_4$alkoxy groups, which have from 1 to 8, 1 to 6, or 1 to 4 carbon atoms, respectively. Alkoxy groups include, for example, methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy and 3-methylpentoxy. Similarly, "alkylthio" refers to an alkyl group as described above attached via a sulfur bridge and "alkylsufonyl" refers to an alkyl groups as described above attached via a —(SO$_2$)— bridge.

An "alkoxyalkyl" group is an alkoxy group as described above attached via an oxygen bridge to an alkyl group, as described above, attached via a single covalent bond on an alkyl carbon.

As used herein the term "alkoxycarbonyl" indicates an alkoxy group, as defined above, having the indicated number of carbon atoms, attached through a keto (—(C═O)—) bridge. The alkoxy moiety of the alkoxycarbonyl group has the indicated number of carbon atoms, the carbon of the keto bridge is not included in this number. $C_3$alkoxycarbonyl group indicates for example, groups of the formula CH$_3$(CH$_2$)$_2$—O—(C═O)— or (CH$_3$)$_2$(CH)—O—(C═O)—.

"Alkanoyl" indicates an alkyl group as defined above, attached through a keto (—(C═O)—) bridge. Alkanoyl groups have the indicated number of carbon atoms, with the carbon of the keto group being included in the numbered carbon atoms. For example a $C_2$alkanoyl group is an acetyl group having the formula CH$_3$(C═O)—.

"Alkylamino" refers to a secondary or tertiary amine having the general structure —NH(alkyl) or —N(alkyl)(alkyl), wherein each alkyl may be the same or different. Such groups include, for example, mono- and di-($C_1$-$C_8$alkyl)amino groups, in which each alkyl may be the same or different and contain from 1 to 8 carbon atoms, as well as mono- and di-(C1-C6alkyl)amino groups and mono- and di-(C1-C4alkyl)amino groups.

"Alkylaminoalkyl" refers to an alkylamino group linked via an alkylene group (i.e., a group having the general structure -alkyl-NH-alkyl or -alkyl-N(alkyl)(alkyl)) in which each alkyl is selected independently. Such groups include, for example, mono- and di-($C_1$-$C_6$alkyl)amino$C_1$-$C_6$alkyl and mono- and di-($C_1$-$C_4$alkyl)amino$C_1$-$C_4$alkyl, in which each alkyl may be the same or different. "Mono- or di-($C_1$-$C_6$alkyl)amino$C_0$-$C_6$alkyl" refers to a mono- or di-($C_1$-$C_6$alkyl)amino group linked via a single covalent bond or a $C_1$-$C_6$alkylene group. The following are representative alkylaminoalkyl groups:

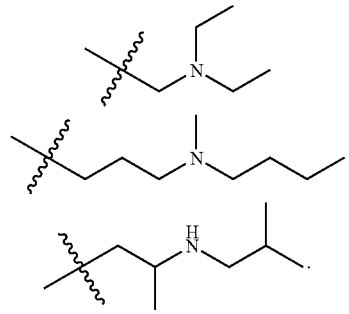

As used herein the term "mono- and/or di-alkylcarboxamide" refers to groups of formula (alkyl$_1$)-NH—(C═O)— and (alkyl$_1$)(alkyl$_2$)-N—(C═O)— in which the alkyl$_1$ and alkyl$_2$ groups are independently chosen alkyl groups as defined above having the indicated number of carbon atoms. "Carboxamide" is a group of the formula —(C═O)NH$_2$.

"Alkyloxime" is an alkyl group as described above attached via a —(C═NOH)— linker.

A "carbocycle" has from 1 to 3 fused, pendant or spiro rings, each of which has only carbon ring members. Typically, a carbocycle that has a single ring contains from 3 to 8 ring members (rings having from 4 or 5 to 7 ring members are recited in certain embodiments) and carbocycles comprising fused, pendant or spiro rings typically contain from 9 to 14 ring members. Carbocycles may be optionally substituted with a variety of substituents, as indicated. Unless otherwise specified, a carbocycle may be a cycloalkyl group (i.e., each ring is saturated or partially saturated) or an aryl group (i.e., at least one ring within the group is aromatic). Certain carbocycles are 4- to 7-membered or 5- to 7-membered groups that are optionally substituted. Representative aromatic carbocycles are phenyl, naphthyl and biphenyl. In certain embodiments preferred carbocycles have a single ring, such as phenyl and 3- to 7-membered cycloalkyl groups. Certain carbocycles may be linked via a single covalent bond or an alkyl or alkoxy linker. For example, phenyl$C_0$-$C_2$alkyl is a phenyl group that is linked via a single covalent bond or a methylene or ethylene group. Similarly, phenyl$C_1$-$C_2$alkoxy is a phenyl group that is linked via a methoxy or ethoxy group, in which the oxygen atom is the point of attachment.

A "cycloalkyl" group is a carbocycle as described above, which is fully or partially saturated. In certain embodiments preferred cycloalkyl groups are 3- to 7-membered cycloalkyl groups having a single saturated ring (e.g., cyclopropyl, cyclopentyl or cyclohexyl), or a partially saturated variant thereof (e.g., cyclopropenyl, cyclopentenyl or cyclohexenyl). A "cycloalkyl$C_0$-$C_n$alkyl" is a cycloalkyl group linked via a single covalent bond or a $C_1$-$C_n$alkylene group (e.g., a $C_1$-$C_4$alkylene group). For example, a ($C_3$-$C_7$cycloalkyl)$C_0$-$C_6$alkyl group is a 3- to 7-membered cycloalkyl group that is linked via a single covalent bond or a $C_1$-$C_6$alkylene group.

The term "halogen" refers to fluorine, chlorine, bromine and iodine.

A "haloalkyl" is a branched or straight-chain alkyl group, substituted with 1 or more halogen atoms (e.g., "halo$C_1$-$C_6$alkyl" groups have from 1 to 6 carbon atoms; "halo$C_1$-$C_4$alkyl" groups have from 1 to 4 carbon atoms). Examples of haloalkyl groups include, but are not limited to, mono-, di- or tri-fluoromethyl; mono-, di- or tri-chloromethyl; mono-, di-, tri-, tetra- or penta-fluoroethyl; mono-, di-, tri-, tetra- or penta-chloroethyl; and 1,2,2,2-tetrafluoro-1-trifluoromethyl-ethyl. Typical haloalkyl groups are trifluoromethyl and difluoromethyl.

"Haloalkoxy" indicates a haloalkyl group as defined above attached through an oxygen bridge. "HaloC1-C6alkoxy" groups have from 1 to 6 carbon atoms.

As used herein, "hydroxyalkyl" is an alkyl group as defined herein, having the indicated number of carbon atoms, and substituted with at least one hydroxyl substituent (—OH). When indicated, hydroxyalkyl groups, like other groups described herein, may be additionally substituted.

A dash ("-") that is not between two letters or symbols is used to indicate a point of attachment for a substituent. For example, —CONH2 is attached through the carbon atom.

A "heteroatom," as used herein, is oxygen, sulfur or nitrogen.

A "heterocycle" has from 1 to 3 fused, pendant or spiro rings, at least one of which is a heterocyclic ring (i.e., one or more ring atoms is a heteroatom, with the remaining ring atoms being carbon). Typically, a heterocyclic ring comprises 1, 2, 3 or 4 independently chosen heteroatoms; within certain embodiments each heterocyclic ring has 1 or 2 heteroatoms per ring, with the remaining ring atoms being carbon. Each ring within a heterocycle generally contains from 3 to 8 ring members (rings having from 4 or 5 to 7 ring members are recited in certain embodiments) and heterocycles comprising fused, pendant or spiro rings typically contain from 9 to 14 ring members. Certain heterocyclic groups are 4- to 7-membered or 5- to 7-membered groups that are optionally substituted. Certain heterocycles comprise a sulfur atom as a ring member; in certain embodiments, the sulfur atom is oxidized to SO or $SO_2$. Heterocycles may be optionally substituted with a variety of substituents, as indicated.

Unless otherwise specified, a heterocycle may be a heterocycloalkyl group (i.e., each ring is saturated or partially saturated) or a heteroaryl group (i.e., at least one ring within the group is aromatic). In certain embodiments, preferred heterocycloalkyl groups are 5- to 7-membered heterocycloalkyl groups having a single saturated ring with 5 to 7 ring members, 1 or 2 ring members independently chosen from N, O and S, with remaining ring members being carbon. A "heterocycloalkyl$C_0$-$C_n$alkyl" is a heterocycloalkyl group linked via a single covalent bond or $C_1$-$C_n$alkylene group, such as a $C_1$-$C_4$alkylene group. 4- to 7-membered heterocycloalkyl groups include, for example, piperidinyl, piperazinyl, pyrrolidinyl, azepanyl, morpholino, thiomorpholino and 1,1-dioxo-thiomorpholin-4-yl. Representative aromatic heterocycles are azocinyl, pyridyl, pyrimidyl, pyridazinyl, imidazolyl and tetrazolyl.

A "substituent," as used herein, refers to a molecular moiety that is covalently bonded to an atom within a molecule of interest. For example, a ring substituent may be a moiety such as a halogen, alkyl group, haloalkyl group or other group discussed herein that is covalently bonded to an atom (preferably a carbon or nitrogen atom) that is a ring member. The term "substitution" refers to replacing a hydrogen atom in a molecular structure with a substituent, such that the valence on the designated atom is not exceeded, and such that a chemically stable compound (i.e., a compound that can be isolated, characterized and tested for biological activity) results from the substitution.

Groups that are "optionally substituted" are unsubstituted or are substituted by other than hydrogen at one or more available positions, typically 1, 2, 3, 4 or 5 positions, by one or more suitable groups (which may be the same or different). Optional substitution is also indicated by the phrase "substituted with 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents).

The term "MCH receptor" refers to any naturally-occurring mammalian (especially human, monkey or canine) MCH type 1 or type 2 receptor, as well as chimeric receptors in which one or more domains of a naturally-occurring MCH1R or MCH2R are replaced with a corresponding domain of a different G protein-coupled receptor, such that the ability of the chimeric receptor to bind MCH and mediate a dose-dependent release of intracellular calcium is not diminished. MCH receptors for use within the various assays and other methods described herein include, for example, recombinantly expressed human MCH receptor (e.g., Genbank Accession No. Z86090; SEQ ID NO:29 of U.S. Patent Application Publication Number 2003/0148457), monkey MCH receptor (e.g., SEQ ID NO:2, 34 or 36 of U.S. Patent Application Publication Number 2003/0114644) or canine MCH receptor (e.g., SEQ ID NO:39 of U.S. Patent Application Publication Number 2003/0114644). Chimeric MCH receptors that may be used as described herein include, for example, those disclosed in U.S. Patent Application Publication Numbers 2003/0114644 and 2003/0148457.

A "MCH receptor modulator," also referred to herein as a "modulator," is a compound that alters (increases or decreases) MCH receptor activation and/or MCH receptor-mediated signal transduction. MCH receptor modulators specifically provided herein are compounds of Formula I and pharmaceutically acceptable salts of such compounds. A modulator may be a MCH receptor agonist or antagonist. In certain embodiments, a MCH receptor modulator may exhibit an $EC_{50}$ or $IC_{50}$ at MCH receptor that is less than 1 micromolar, 500 nM, 200 nM, 100 nM, 50 nM, 25 nM or 10 nM in a standard calcium mobilization assay (as described in Example 10, herein) and/or an agonist-stimulated GTP gamma$^{35}$S binding assay (as described in Example 14, herein). A modulator may be a MCH receptor agonist or antagonist, although, for certain purposes described herein, a modulator preferably inhibits MCH receptor activation resulting from binding of MCH (i.e., the modulator is an antagonist).

A MCH receptor modulator binds with "high affinity" if the Ki at a MCH receptor is less than 1 micromolar, preferably less than 500 nanomolar, 100 nanomolar or 10 nanomolar. A modulator binds "specifically" to MCH receptor if it binds to a MCH receptor (total binding minus nonspecific binding) with a $K_i$ that is 10-fold, preferably 100-fold, and more preferably 1000-fold, less than the $K_i$ measured for modulator binding to other G protein-coupled receptors. For example, a modulator may have a $K_i$ of 500 nanomolar or less in an MCH receptor ligand binding assay and a $K_i$ of at least 1 micromolar in a dopamine receptor ligand binding assay, such as the assay described in Example 7 (pages 111-112) of PCT International Publication Number WO 02/094799, which is hereby incorporated by reference. Representative assays for determining $K_i$ at MCH receptor are provided in Examples 9, 10, 12 and 14, herein.

A modulator is considered an "antagonist" if it detectably inhibits MCH binding to MCH receptor and/or MCH-mediated signal transduction (using, for example, the representative assay provided in Example 10 or Example 14); in general, such an antagonist has a $IC_{50}$ value of less than 1 micromolar, preferably less than 100 nanomolar, and more preferably less than 10 nanomolar within the assay provided in Example 10 and/or the assay provided in Example 14. MCH receptor antagonists include neutral antagonists and inverse agonists.

An "inverse agonist" is a compound that reduces the activity of MCH receptor below its basal activity level in the absence of added ligand. Inverse agonists may also inhibit the activity of MCH at MCH receptor, and/or may also inhibit binding of MCH to MCH receptor. The ability of a compound to inhibit the binding of MCH to MCH receptor may be measured by a binding assay, such as the binding assays given in Example 9 and Example 12. The basal activity of MCH receptor, as well as the reduction in MCH receptor activity due to the presence of antagonist, may be determined from a calcium mobilization assay, such as the assay of Example 10, or an agonist-stimulated GTP gamma$^{35}$S binding assay, such as the assay described in Example 14.

A "neutral antagonist" of MCH receptor is a compound that inhibits the activity of MCH at MCH receptor, but does not significantly change the basal activity of the receptor (e.g., within an assay as described in Example 10 or Example 14 performed in the absence of ligand, MCH receptor activity is reduced by no more than 10%, more preferably by no more than 5%, and even more preferably by no more than 2%; most preferably, there is no detectable reduction in activity). Neutral antagonists may also inhibit ligand binding of ligand to MCH receptor.

As used herein a "MCH receptor agonist" is a compound that elevates the activity of the receptor above the basal activity level of the receptor (i.e., enhances MCH receptor activation and/or MCH receptor-mediated signal transduction). MCH receptor agonist activity may be identified using the representative assays provided in Example 10 and Example 14. In general, such an agonist has an $EC_{50}$ value of less than 1 micromolar, preferably less than 100 nanomolar, and more preferably less than 10 nanomolar within the assay provided in Example 10 and/or in the assay provided in Example 14.

A "therapeutically effective amount" (or dose) is an amount that, upon administration, is sufficient to provide a discernible patient benefit. For example, a therapeutically effective amount may reduce symptom severity or frequency and/or may result in detectable weight loss. Alternatively, or in addition, a therapeutically effective amount may improve patient status or outcome and/or prevent or delay disease or symptom onset. A therapeutically effective amount or dose generally results in a concentration of compound in a body fluid (such as blood, plasma, serum, CSF, synovial fluid, lymph, cellular interstitial fluid, tears or urine) that is sufficient to alter the binding of ligand to MCH receptor in vitro (using the assay provided in Example 9 or Example 12) and/or MCH-mediated signal transduction (using an assay provided in Example 10 or Example 14).

A "disease or disorder associated with MCH receptor activation," as used herein is any condition that is characterized by inappropriate stimulation of MCH receptor, regardless of the amount of MCH present locally, and/or that is responsive to modulation of MCH receptor activity (i.e., the condition or a symptom thereof is alleviated by such modulation). Such conditions include, for example, metabolic disorders (such as diabetes), heart disease, stroke, eating disorders (such as obesity and bulimia nervosa) and sexual disorders such as anorgasmic and psychogenic impotence, as well as other diseases and disorders recited herein.

A "patient" is any individual treated with a MCH modulator as provided herein. Patients include humans, as well as other animals such as companion animals (e.g., dogs and cats) and livestock. Patients may be experiencing one or more symptoms of a condition associated with MCH receptor modulation, or may be free of such symptom(s) (i.e., treatment may be prophylactic).

Melanin Concentrating Hormone Receptor Modulators

As noted above, the present invention provides substituted 1-benzyl-4-substituted piperazine analogues of Formula I. Certain such compounds are MCH receptor modulators, which may be specific for a particular MCH receptor (e.g., type 1 or type 2) or may inhibit or enhance ligand binding to multiple MCH receptors. MCH receptor modulators may be used to modulate MCH receptor activity in vivo, especially in the treatment of metabolic, feeding and sexual disorders in humans, domesticated companion animals and livestock animals. Modulators may also be used within a variety of in vitro assays, such as assays for receptor activity, as probes for detection and localization of MCH receptors and as standards in assays of MCH binding and MCH-mediated signal transduction.

The substituted 1-benzyl-4-substituted piperazine analogues provided herein are generally multi-aryl (i.e., have a plurality of unfused or fused aryl groups), non-peptide and amino acid free, and detectably modulate MCH receptor activity at submicromolar concentrations, preferably at sub-nanomolar concentrations.

Within certain compounds of Formula I:

W is nitrogen, CH or C—OH;

$Y_1$ is CH or nitrogen;

$Y_3$ and $Y_4$ are independently $CR_1$ or nitrogen; and Z is nitrogen or $CR_2$; such that at least one of $Y_3$, $Y_4$ and Z is nitrogen, and at least one of $Y_3$, $Y_4$ and Z is substituted carbon;

$R_2$ is halogen, nitro, cyano, amino, acetyl, carboxamide, imino, $C_1$-$C_6$alkyl, $C_2$-$C_6$alkenyl, $C_2$-$C_6$alkynyl, $C_2$-$C_6$alkanoyl, $C_2$-$C_6$alkyloxime, $C_1$-$C_6$alkoxy, $C_1$-$C_6$alkoxyC$_1$-C$_4$alkyl, hydroxyC$_1$-$C_6$alkyl, $C_1$-$C_6$alkoxycarbonyl, mono- or di-alkylcarboxamide, $C_1$-$C_6$alkylthio, $C_1$-$C_6$alkylsulfonyl, haloC$_1$-$C_6$alkyl, haloC$_1$-$C_6$alkoxy, aminoC$_1$-$C_6$alkyl, mono- or di-($C_1$-$C_6$alkyl)aminoC$_0$-$C_6$alkyl, or ($C_3$-$C_7$cycloalkyl)C$_0$-$C_6$alkyl, or $R_2$ is (3- to 7-membered heterocycloalkyl)C$_0$-$C_6$alkyl, phenylC$_0$-$C_2$alkyl, phenylC$_1$-$C_2$alkoxy or (5- or 6-membered heteroaryl)C$_0$-$C_2$alkyl, each of which is substituted with 0 to 3 substituents independently chosen from halogen, $C_1$-$C_2$alkoxy and $C_1$-$C_2$alkyl; or $R_2$ is taken together with a $R_1$ to form a fused 5- or 6-membered carbocycle or heterocycle, which is substituted with 0 to 3 substituents independently chosen from halogen, $C_1$-$C_2$alkoxy and $C_1$-$C_2$alkyl;

$R_8$ is: (i) halogen, hydroxy, nitro, cyano, —COOH or a group of the formula L-M; or (ii) taken together with $R_7$ to form a fused 5- or 6-membered carbocycle or heterocycle;

$R_{11}$ is: (i) halogen, hydroxy, nitro, cyano, —COOH or a group of the formula L-M; or (ii) taken together with $R_9$ to form a fused carbocycle or heterocycle;

If $Y_1$ and $Y_3$ are both nitrogen and $R_{11}$ is trifluoromethyl, then $R_2$ is not amino;

and the remaining variables are as described above for Formula I.

Such compounds are referred to herein as compounds of Formula Ia.

Certain compounds of Formulas I and Ia satisfy one or more of the following conditions:

(a) Q is $CR_8$ and X is $CR_{11}$.

(b) P is $CR_7$.

(c) P is $CR_7$ and $R_7$ is not hydrogen.

(d) $R_{11}$ is $C_1$-$C_4$alkoxy.

(e) U is $CR_9$ and T is $CR_{10}$.

(f) $R_7$ and $R_9$ are each chosen from $C_1$-$C_4$alkyl.

(g) $R_3$ is methyl and $R_4$ is hydrogen.

(h) $R_3$ is taken together with $R_6$ to form a fused 5- to 7-membered heterocycloalkyl.

(i) V is C=O.

(j) Z is $CR_2$.

(k) $R_2$ is halogen, cyano, amino, $C_1$-$C_4$alkyl, $C_2$-$C_4$alkenyl, $C_2$-$C_4$alkynyl, $C_1$-$C_4$alkoxy, $C_1$-$C_4$alkylthio, haloC$_1$-$C_4$alkyl, mono- or di-($C_1$-$C_4$alkyl)amino, ($C_3$-$C_7$cycloalkyl)C$_0$-$C_4$alkyl or (4- to 7-membered heterocycloalkyl)C$_0$-$C_4$alkyl, or $R_2$ is taken together with a $R_1$ to form a fused 5- or 6-membered carbocycle or heterocycle. In certain embodiments, $R_2$ is halogen, cyano, methyl, ethyl, isopropyl, methoxy, ethoxy, methylthio, ethylthio, trifluoromethyl or mono- or di-methylamino.

Certain compounds of Formula I also satisfy Formula II or Formula III:

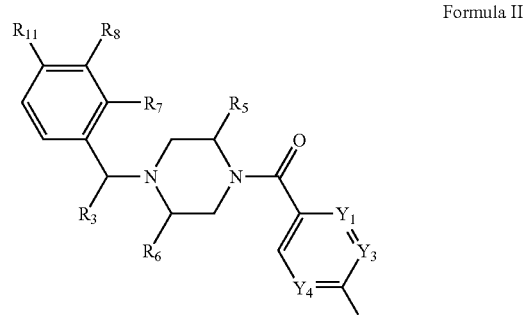

Formula II

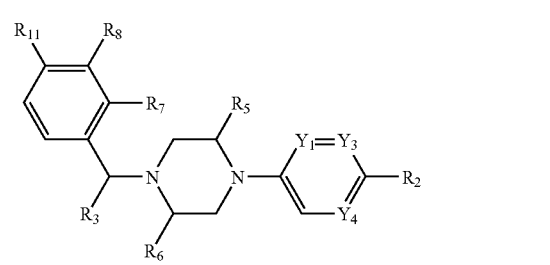

Formula III

Within Formulas II and III:

$Y_1$ is CH, C—CH$_3$ or nitrogen.

$Y_3$ and $Y_4$ are independently $CR_1$ or nitrogen, such that at least one of $Y_3$ and $Y_4$ is nitrogen, and $Y_1$ is carbon if $Y_3$ is nitrogen.

Each $R_1$ is independently: (i) hydrogen, halogen, hydroxy, cyano, amino, $C_1$-$C_6$alkyl, $C_2$-$C_6$alkenyl, $C_2$-$C_6$alkynyl, $C_1$-$C_6$alkoxy, haloC$_1$-$C_6$alkyl, aminoC$_1$-$C_6$alkyl or ($C_3$-$C_7$cycloalkyl)C$_0$-$C_2$alkyl; or (ii) taken together with $R_2$ to form a fused 5- or 6-membered carbocycle or heterocycle.

$R_2$ is halogen, cyano, amino, $C_1$-$C_4$alkyl, $C_2$-$C_4$alkenyl, $C_2$-$C_4$alkynyl, $C_1$-$C_4$alkoxy, $C_1$-$C_4$alkylthio, haloC$_1$-$C_4$alkyl, mono- or di-($C_1$-$C_4$alkyl)amino, ($C_3$-$C_7$cycloalkyl)C$_0$-$C_4$alkyl, (4- to 7-membered heterocycloalkyl)C$_0$-$C_4$alkyl or taken together with a $R_1$ to form a fused 5- or 6-membered carbocycle or heterocycle.

$R_3$ is: (i) hydrogen or $C_1$-$C_4$alkyl; or (ii) taken together with $R_6$ to form a fused 5- to 7-membered heterocycloalkyl.

$R_5$ is: (i) hydrogen, halogen, hydroxy, nitro, cyano, amino, $C_1$-$C_6$alkyl, $C_2$-$C_6$alkenyl, $C_2$-$C_6$alkynyl, $C_1$-$C_6$alkoxy, haloC$_1$-$C_6$alkyl, haloC$_1$-$C_6$alkoxy, mono- or di-($C_1$-$C_6$alkyl)amino or aminoC$_1$-$C_6$alkyl; or (ii) taken together with $R_6$ to form a methylene bridge.

$R_6$ is: (i) selected from hydrogen, halogen, hydroxy, nitro, cyano, amino, $C_1$-$C_6$alkyl, $C_2$-$C_6$alkenyl, $C_2$-$C_6$alkynyl, $C_1$-$C_6$alkoxy, haloC$_1$-$C_6$alkyl, haloC$_1$-$C_6$alkoxy, mono- and di-($C_1$-$C_6$alkyl)amino and aminoC$_1$-$C_6$alkyl; (ii) taken together with $R_3$ to form a fused heterocycloalkyl; or (iii) taken together with $R_5$ to form a methylene bridge. In some embodiments, $R_5$ and $R_6$ are each independently hydrogen or methyl.

$R_7$ is hydrogen, halogen, hydroxy, cyano, $C_1$-$C_6$alkyl, $C_2$-$C_6$alkenyl, $C_2$-$C_6$alkynyl or $C_1$-$C_6$alkoxy. In certain embodiments, $R_7$ is not hydrogen.

$R_8$ is halogen, hydroxy, cyano, $C_1$-$C_6$alkyl, $C_2$-$C_6$alkenyl, $C_2$-$C_6$alkynyl or $C_1$-$C_{C6}$alkoxy. In certain embodiments, $R_8$ is $C_1$-$C_4$alkyl.

$R_{11}$ is halogen, hydroxy, cyano, amino, $C_1$-$C_6$alkyl, $C_2$-$C_6$alkenyl, $C_2$-$C_6$alkynyl, $C_1$-$C_6$alkoxy, $C_1$-$C_6$alkylamino, halo$C_1$-$C_6$alkyl, halo$C_1$-$C_6$alkoxy or amino$C_1$-$C_6$alkyl. In some embodiments, $R_{11}$ is $C_1$-$C_4$alkoxy.

Within certain compounds of Formula II and Formula III, $R_5$ and $R_6$ are taken together to form a methylene bridge.

Within certain compounds of Formula II and Formula III, $R_6$ is taken together with $R_3$ to form a fused 6-membered heterocycloalkyl.

Within certain compounds of Formula II and Formula III, $R_7$ is methyl, $R_8$ is methyl and $R_{11}$ is methoxy.

Certain compounds of Formula I also satisfy Formula IV or Formula V, in which the variables are as described for Formula I:

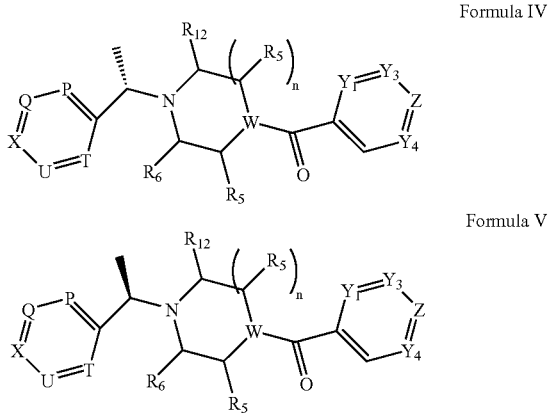

Formula IV

Formula V

Within certain compounds of Formula IV and Formula V, W is N.

Certain compounds of Formula IV or Formula V further satisfy Formula VI (in which variables are as described for Formulas IV and V):

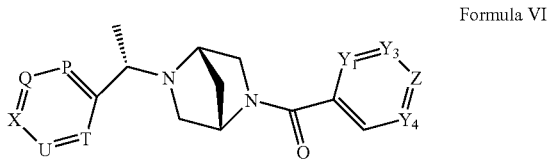

Formula VI

Also provided herein are compounds of Formulas IV-VI that satisfy one or more of the following conditions:

(a) Q is $CR_8$ and X is $CR_{11}$.
(b) P is $CR_7$.
(c) $R_7$ is not hydrogen.
(d) $R_{11}$ is $C_1$-$C_4$alkoxy.
(e) $R_8$ is $C_1$-$C_4$alkyl.
(f) Z is $CR_2$.
(g) $R_2$ is halogen, cyano, amino, $C_1$-$C_4$alkyl, $C_2$-$C_4$alkenyl, $C_2$-$C_4$alkynyl, $C_1$-$C_4$-$C_4$alkylthio, halo$C_1$-$C_4$alkyl, halo$C_1$-$C_4$alkoxy, mono- or di-($C_1$-$C_4$alkyl)amino, ($C_3$-$C_7$cycloalkyl)$C_0$-$C_4$alkyl, (4- to 7-membered heterocycloalkyl)$C_0$-$C_4$alkyl or taken together with a $R_1$ to form a fused 5- or 6-membered carbocycle or heterocycle. In some embodiments $R_2$ is halogen, cyano, methyl, ethyl, isopropyl, methoxy, ethoxy, methylthio, ethylthio, trifluoromethyl or mono- or di-methylamino.

Representative compounds of Formulas I-VI include, but are not limited to, those specifically described in Examples 1-8. It will be apparent that the compounds recited therein are representative only, and are not intended to limit the scope of the present invention. Further, as noted above, all compounds may be present, for example, as free base or as a pharmaceutically acceptable salt.

In certain embodiments, compounds provided herein detectably alter (modulate) MCH binding to MCH1R and/or MCH2R, as determined using a standard in vitro MCH receptor binding assay and/or functional assay (such as the assays provided in Examples 10 and 14). References herein to a "MCH receptor ligand binding assay" refer to either of the standard in vitro receptor binding assays provided in Example 9 and Example 12. Within such assays, the receptor is incubated with labeled MCH (or other suitable ligand) and a test compound. A test compound that detectably modulates binding to MCH receptor will result in a decrease or increase in the amount of label bound to the MCH receptor preparation, relative to the amount of label bound in the absence of the compound. Preferably, such a compound will exhibit a $K_i$ at an MCH receptor of less than 1 micromolar, more preferably less than 500 nM, 100 nM, 20 nM or 10 nM, within an assay performed as described in Example 9 and/or within an assay performed as described in Example 12. Certain preferred compounds are MCH receptor antagonists, and exhibit $IC_{50}$ values of about 4 micromolar or less, more preferably 1 micromolar or less, still more preferably about 100 nanomolar or less, or 10 nanomolar or less within a standard in vitro MCH receptor mediated calcium mobilization assay, as provided in Example 10 and/or an agonist-stimulated GTP gamma$^{35}$S binding assay, as described in Example 14.

If desired, MCH receptor modulators provided herein may be evaluated for certain pharmacological properties including, but not limited to, oral bioavailability (preferred compounds are orally bioavailable to an extent allowing for oral doses of less than 140 mg/kg, preferably less than 50 mg/kg, more preferably less than 30 mg/kg, even more preferably less than 10 mg/kg, still more preferably less than 1 mg/kg), toxicity (a preferred MCH receptor modulator is nontoxic when a therapeutically effective amount is administered to a subject), side effects (a preferred MCH receptor modulator produces side effects comparable to placebo when a therapeutically effective amount of the compound is administered to a subject), serum protein binding and in vitro and in vivo half-life (a preferred MCH receptor modulator exhibits an in vitro half-life that is equal to an in vivo half-life allowing for Q.I.D. dosing, preferably T.I.D. dosing, more preferably B.I.D. dosing, and most preferably once-a-day dosing). In addition, differential penetration of the blood brain barrier may be desirable for MCH receptor modulators used to treat CNS disorders, while low brain levels of MCH receptor modulators used to treat peripheral disorders are preferred. Routine assays that are well known in the art may be used to assess these properties and identify superior compounds for a particular use. For example, assays used to predict bioavailability include transport across human intestinal cell monolayers, including Caco-2 cell monolayers. Penetration of the blood brain barrier of a compound in humans may be predicted from the brain levels of the compound in laboratory animals given the compound (e.g., intravenously). Serum protein binding may be predicted from albumin binding assays. Compound half-life is inversely proportional to the frequency of dosage of a compound. In vitro half-lives of compounds may be predicted from assays of microsomal half-life as described within Example 16, herein.

As noted above, preferred MCH receptor modulators provided herein are nontoxic. In general, the term "nontoxic" as used herein shall be understood in a relative sense and is intended to refer to any substance that has been approved by the United States Food and Drug Administration ("FDA") for administration to mammals (preferably humans) or, in keeping with established criteria, is susceptible to approval by the FDA for administration to mammals (preferably humans). In addition, a highly preferred nontoxic compound generally satisfies one or more of the following criteria when administered in minimum therapeutically effective amounts, or when contacted with cells at a concentration that is sufficient to inhibit the binding of MCH receptor ligand to MCH receptor in vitro: (1) does not substantially inhibit cellular ATP production; (2) does not significantly prolong heart QT intervals; (3) does not cause substantial liver enlargement and (4) does not cause substantial release of liver enzymes.

As used herein, a compound that does not substantially inhibit cellular ATP production is a compound that satisfies the criteria set forth in Example 15, herein. In other words, cells treated as described in Example 15 with 100 μM of such a compound exhibit ATP levels that are at least 50% of the ATP levels detected in untreated cells. In more highly preferred embodiments, such cells exhibit ATP levels that are at least 80% of the ATP levels detected in untreated cells. The concentration of MCH receptor modulator used in such assays is generally at least 10-fold, 100-fold or 1000-fold greater than the $EC_{50}$ or $IC_{50}$ for the modulator in the calcium mobilization assay of Example 10.

A compound that does not significantly prolong heart QT intervals is a compound that does not result in a statistically significant prolongation of heart QT intervals (as determined by electrocardiography) in guinea pigs, minipigs or dogs upon administration of a dose that yields a serum concentration equal to the $EC_{50}$ or $IC_{50}$ for the compound. In certain preferred embodiments, a dose of 0.01, 0.05, 0.1, 0.5, 1, 5, 10, 40 or 50 mg/kg administered parenterally or orally does not result in a statistically significant prolongation of heart QT intervals. By "statistically significant" is meant results varying from control at the p<0.1 level or more preferably at the p<0.05 level of significance as measured using a standard parametric assay of statistical significance such as a student's T test.

A compound does not cause substantial liver enlargement if daily treatment of laboratory rodents (e.g., mice or rats) for 5-10 days with a dose that yields a serum concentration equal to the $EC_{50}$ or $IC_{50}$ for the compound results in an increase in liver to body weight ratio that is no more than 100% over matched controls. In more highly preferred embodiments, such doses do not cause liver enlargement of more than 75% or 50% over matched controls. If non-rodent mammals (e.g., dogs) are used, such doses should not result in an increase of liver to body weight ratio of more than 50%, preferably not more than 25%, and more preferably not more than 10% over matched untreated controls. Preferred doses within such assays include 0.01, 0.05., 0.1, 0.5, 1, 5, 10, 40 or 50 mg/kg administered parenterally or orally.

Similarly, a compound does not promote substantial release of liver enzymes if administration of twice the minimum dose that yields a serum concentration equal to the $EC_{50}$ or $IC_{50}$ for the compound does not elevate serum levels of ALT, LDH or AST in laboratory rodents by more than 100% over matched mock-treated controls. In more preferred embodiments, such doses do not elevate such serum levels by more than 75% or 50% over matched controls. Alternatively, a compound does not promote substantial release of liver enzymes if, in an in vitro hepatocyte assay, concentrations (in culture media or other such solutions that are contacted and incubated with hepatocytes in vitro) that are equal to the $EC_{50}$ or $IC_{50}$ for the compound do not cause detectable release of any of such liver enzymes into culture medium above baseline levels seen in media from matched mock-treated control cells. In more highly preferred embodiments, there is no detectable release of any of such liver enzymes into culture medium above baseline levels when such compound concentrations are five-fold, and preferably ten-fold, the $EC_{50}$ or $IC_{50}$ for the compound.

In other embodiments, certain preferred compounds do not inhibit or induce microsomal cytochrome P450 enzyme activities, such as CYP1A2 activity, CYP2A6 activity, CYP2C9 activity, CYP2C19 activity, CYP2D6 activity, CYP2E1 activity or CYP3A4 activity at a concentration equal to the $EC_{50}$ or $IC_{50}$ for the compound.

Certain preferred compounds are not clastogenic (e.g., as determined using a mouse erythrocyte precursor cell micronucleus assay, an Ames micronucleus assay, a spiral micronucleus assay or the like) at a concentration equal the $EC_{50}$ or $IC_{50}$ for the compound. In other embodiments, certain preferred MCH receptor modulators do not induce sister chromatid exchange (e.g., in Chinese hamster ovary cells) at such concentrations.

For detection purposes, as discussed in more detail below, MCH receptor modulators provided herein may be isotopically-labeled or radiolabeled. For example, compounds of Formula I may have one or more atoms replaced by an atom of the same element having an atomic mass or mass number different from the atomic mass or mass number usually found in nature. Examples of isotopes that can be present in the compounds provided herein include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$. In addition, substitution with heavy isotopes such as deuterium (i.e., $^2H$) can afford certain therapeutic advantages resulting from greater metabolic stability, for example increased in vivo half-life or reduced dosage requirements and, hence, may be preferred in some circumstances.

Pharmaceutical Compositions

Compounds of Formula I can be administered as the neat chemical, but are preferably administered as a pharmaceutical composition comprising such a compound, together with at least one physiologically acceptable carrier, excipient, adjuvant and/or diluent. Pharmaceutical compositions may comprise, for example, water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. Preferred pharmaceutical compositions are formulated for oral delivery to humans or other animals (e.g., companion animals such as dogs).

Pharmaceutical carriers must be of sufficiently high purity and sufficiently low toxicity to render them suitable for administration to the animal being treated. The carrier can be inert or it can possess pharmaceutical benefits. The amount of carrier employed in conjunction with the compound is sufficient to provide a practical quantity of material for administration per unit dose of the compound.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil and corn oil; polyols such as propylene glycol, glycerine, sorbitol, mannitol and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Effective concentrations of one or more of the compounds provided herein are mixed with a suitable pharmaceutical carrier, excipients, adjuvant or vehicle. In instances in which the compounds exhibit insufficient solubility, methods for solubilizing compounds may be used. Such methods are known to those of skill in this art and include, but are not limited to, using cosolvents, such as dimethylsulfoxide (DMSO), using surfactants, such as TWEEN, or dissolution in aqueous sodium bicarbonate. Derivatives of the compounds, such as salts of the compounds or prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the chosen carrier or vehicle.

Compounds may be administered orally, topically, parenterally, by inhalation or spray, sublingually, transdermally, via buccal administration, rectally, as an ophthalmic solution, or by other means, in dosage unit formulations.

Dosage formulations suitable for oral use include, for example, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. Orally administered compositions also include liquid solutions, emulsions, suspensions, powders, granules, elixirs, tinctures, syrups and the like. The pharmaceutically acceptable carriers suitable for preparation of such compositions are well known in the art. Oral formulations may contain preservatives, flavoring agents, sweetening agents, such as sucrose or saccharin, taste-masking agents and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such formulations may also contain a demulcent.

Orally Administered Liquid Formulations

Compounds can be incorporated into oral liquid preparations such as, for example, aqueous or oily suspensions, solutions, emulsions, syrups or elixirs. Moreover, formulations can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel and hydrogenated edible fats), emulsifying agents (e.g., lecithin, sorbitan monsoleate or acacia), non-aqueous vehicles, which can include edible oils (e.g., almond oil, fractionated coconut oil, silyl esters, propylene glycol and ethyl alcohol) and preservatives (e.g., methyl or propyl p-hydroxybenzoate and sorbic acid).

Suspensions

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin or condensation products of an alkylene oxide with fatty acids, for example polyoxyethylene stearate or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavoring agents may be added to provide palatable oral preparations. These compositions may be preserved by the addition of an anti-oxidant such as ascorbic acid.

Emulsions

Pharmaceutical compositions provided herein may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin and esters or partial esters derived from fatty acids and hexitol, anhydrides, for example sorbitan monoleate, and condensation products of the said partial esters with ethylene oxide, for example polyoxyethylene sorbitan monoleate.

Dispersible Powders

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets and Capsules

Tablets typically comprise conventional pharmaceutically compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint and fruit flavors, are useful adjuvants for chewable tablets. Capsules (including time release and sustained release formulations) typically comprise one or more solid diluents disclosed above. The selection of carrier components often depends on secondary considerations like taste, cost and shelf stability.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Injectable and Parenteral Formulations

Pharmaceutical compositions may be in the form of a sterile injectable aqueous or oleaginous suspension. Such a suspension may be formulated according to the known art using dispersing or wetting agents and suspending agents as described above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid are useful in the preparation of injectables.

Compounds may be administered parenterally in a sterile medium. Parenteral administration includes subcutaneous injections, intravenous, intramuscular, intrathecal injection or infusion techniques. The compound(s), depending on the vehicle and concentration used, can either be suspended or dissolved in the vehicle. Adjuvants such as local anesthetics, preservatives and buffering agents can also be dissolved in the vehicle. In many compositions for parenteral administration, the carrier comprises at least about 90% by weight of the total composition. Preferred carriers for parenteral administration include propylene glycol, ethyl oleate, pyrrolidone, ethanol and sesame oil.

Suppositories

Compounds may also be administered in the form of suppositories for rectal administration of the drug. These compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

Topical Formulations

Compounds may be formulated for local or topical application, such as for topical application to the skin and mucous membranes, such as in the eye, in the form of gels, creams and lotions and for application to the eye. Topical compositions of the present invention may be in any form including, for example, solutions, creams, ointments, gels, lotions, milks, cleansers, moisturizers, sprays, skin patches and the like.

Such solutions may be formulated as 0.01%-10% isotonic solutions, pH about 5-7, with appropriate salts. Compounds may also be formulated for transdermal administration as a transdermal patch.

Topical compositions containing the active compound can be admixed with a variety of carrier materials well known in the art, such as, for example, water, alcohols, aloe vera gel, allantoin, glycerine, vitamin A and E oils, mineral oil, propylene glycol, PPG-2 myristyl propionate and the like. Other materials suitable for use in topical carriers include, for example, emollients, solvents, humectants, thickeners and powders. Examples of each of these types of materials, which can be used singly or as mixtures of one or more materials, are as follows: emollients, such as stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate and myristyl myristate; propellants, such as propane, butane, iso-butane, dimethyl ether, carbon dioxide and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose and ethylene glycol monostearate.

Compounds may also be topically administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Other Formulations

Other compositions useful for attaining systemic delivery of the subject compounds include sublingual, buccal and nasal dosage forms. Such compositions typically comprise one or more of soluble filler substances such as sucrose, sorbitol and mannitol, and binders such as acacia, microcrystalline cellulose, carboxymethyl cellulose and hydroxypropyl methylcellulose. Glidants, lubricants, sweeteners, colorants, antioxidants and flavoring agents disclosed above may also be included.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

In addition to or together with the above modes of administration, a modulator may be conveniently added to food or drinking water (e.g., for administration to non-human animals including companion animals, such as dogs and cats and livestock). Animal feed and drinking water compositions may be formulated so that the animal takes in an appropriate quantity of the composition along with its diet. It may also be convenient to present the composition as a premix for addition to feed or drinking water.

Additional Components

The compositions of the present invention may also optionally comprise an activity enhancer. The activity enhancer can be chosen from a wide variety of molecules that function in different ways to enhance MCH receptor modulator effect. Particular classes of activity enhancers include skin penetration enhancers and absorption enhancers.

Pharmaceutical Compositions for Combination Therapy

Pharmaceutical compositions provided herein may also contain additional active agents, which can be chosen from a wide variety of molecules and can function in different ways to enhance the therapeutic effects of a MCH receptor modulator, or to provide a separate therapeutic effect that does not substantially interfere with the activity of the MCH receptor modulator. Such optional active agents, when present, are typically employed in the compositions described herein at a level ranging from about 0.01% to about 50% by weight of the composition, preferably 0.1% to 25%, 0.2% to 15, 0.5% to 10% or 0.5% to 5% by weight of the composition. For example, compositions intended for the treatment of eating disorders, particularly obesity and bulimia nervosa, may further comprise leptin, a leptin receptor agonist, a melanocortin receptor 4 (MC4) agonist, sibutramine, dexfenfluramine, a growth hormone secretagogue, a beta-3 agonist, a 5HT-2 agonist, an orexin antagonist, a neuropeptide $Y_1$ or $Y_5$ antagonist, a galanin antagonist, a CCK agonist, a GLP-1 agonist, a cannabinoid receptor antagonist (e.g., a CB1 antagonist) and/or a corticotropin-releasing hormone agonist. Other active ingredients that may be included within the compositions provided herein include antidepressants, inhibitors of dipeptidyl peptidase IV (DPP IV) and/or diuretics.

In certain embodiments, an additional active agent is a CB1 antagonist. Representative CB1 antagonists include, for example, certain pyrimidines (e.g., PCT International Application Publication No. WO 04/029,204), pyrazines (e.g., PCT International Application Publication Nos. WO 01/111,038; WO 04/111,034 and WO 04/111,033), azetidine derivatives (e.g., U.S. Pat. Nos. 6,518,264; 6,479,479 and 6,355,631; and PCT International Application Publication No. WO 03/053431), pyrazole derivatives (e.g., U.S. Pat. Nos. 6,509,367 and 6,476,060; and PCT International Application Publication Nos. WO 03/020217 and WO 01/029007), pyrazolecarboxylic acid and pyrazole carboxamide derivatives (e.g., U.S. Pat. Nos. 6,645,985; 6,432,984; 6,344,474; 6,028,084; 5,925,768; 5,624,941 and 5,462,960; published US applications US 2004/0039024; US 2003/0199536 and US 2003/0003145; and PCT International Application Publication Nos. WO 03/078413; WO 03/027076; WO 03/026648 and WO 03/026647); aroyl substituted benzofurans (e.g., LY-320135, U.S. Pat. No. 5,747,524); substituted imidazoles (e.g., published US application US 2003/0114495 and PCT International Application Publication Nos. WO 03/063781 and WO 03/040107); substituted furo[2,3-b]pyridine derivatives (e.g., PCT International Application Publication No. WO 04/012671); substituted aryl amides (e.g., PCT International Application Publication Nos. WO 03/087037 and WO 03/077847); substituted bicyclic or spirocyclic amides (e.g., PCT International Application Publication Nos. WO 03/086288 and WO 03/082190); and substituted 2,3-diphenyl pyridines (e.g., PCT International Application Publication No. WO 03/082191). Other CB1 antagonists are cannabidiol and its derivatives. Preferred CB1 antagonists include, for example, aryl substituted pyrazole carboxamides such as SR-141716A (N-piperidin-1-yl)-5-(4-chlorophenyl)-1-(2,4-dichlorophenyl)-4-methyl-1-H-pyrazole-3-carboxamide, also known as RIMONABANT™ or ACOMPLIA™) as well analogues thereof such as AM251 (N-piperidin-1-yl)-5-(4-iodophenyl)-1-(2,4-dichlorophenyl)-4-methyl-1-H-pyrazole-3-carboxamide) and AM281 (N-(morpholin-4-yl)-1-(2,4-dichlorophenyl)-5-(4-iodophenyl)-4-methyl-1-H-pyrazole-3-carboxamide); various azetidine compounds (e.g., U.S. Pat. Nos. 6,518,264; 6,479,479 and 6,355,631) and the imidazoles 1-(4-chlorophenyl)-2-(2-chlorophenyl)-N-[(1S,2S)-2-hydroxycyclohexyl]-1H-imidazole-4-carboxamide and 2-(2-chlorophenyl)-1-(4-chlorophenyl)-N'-[4-(trifluoromethyl)phenyl]-1H-imidazole-4-carbohydrazide.

Packaged Pharmaceutical Preparations

Pharmaceutical compositions may be packaged for treating or preventing a disease or disorder that is associated with MCH receptor activation (e.g., treatment of metabolic disorders such as diabetes, heart disease, stroke, eating disorders such as obesity or bulimia, skin disorders such as vitiligo, or sexual disorders such as anorgasmic or psychogenic impotence), or for promoting weight loss. Other such diseases and disorders are described herein. Packaged pharmaceutical preparations include a container holding a therapeutically effective amount of MCH receptor modulator as described herein and instructions (e.g., labeling) indicating that the contained composition is to be used for treating or preventing a disease or disorder that is associated with MCH receptor activation in the patient. Prescribing information may be provided to a patient or health care provider or as a label in a packaged pharmaceutical formulation. Prescribing information may include, for example, efficacy, dosage and administration, contraindication and adverse reaction information pertaining to the pharmaceutical formulation. Certain packaged pharmaceutical preparations further include a second therapeutic agent as discussed above.

Dosages

Modulators are generally present within a pharmaceutical composition in a therapeutically effective amount. Compositions providing dosage levels ranging from about 0.1 mg to about 140 mg per kilogram of body weight per day are preferred (about 0.5 mg to about 7 g per human patient per day), with dosages ranging from 0.1 mg to 50 mg, 30 mg or 10 mg particularly preferred. The amount of active ingredient that may be combined with the carrier materials to produce a single dosage form will vary depending upon the host treated and the particular mode of administration. Dosage unit forms will generally contain between from about 1 mg to about 500 mg of each active ingredient. It will be understood, however, that the optimal dose for any particular patient will depend upon a variety of factors, including the activity of the specific compound employed; the age, body weight, general health, sex and diet of the patient; the time and route of administration; the rate of excretion; any simultaneous treatment, such as a drug combination; and the type and severity of the particular disease undergoing treatment. Dosage units will generally contain between from about 10 µg to about 500 mg of an active ingredient. Optimal dosages may be established using routine testing and procedures that are well known in the art.

Methods of Use

Within certain aspects, the present invention provides methods for inhibiting the development of a disease or disorder associated with MCH receptor modulation. In other words, therapeutic methods provided herein may be used to treat a patient already afflicted with a disease, or may be used to prevent or delay the onset of such a disease in a patient who is free of detectable disease that is associated with MCH receptor activation. As noted above, a disease or disorder is "associated with MCH receptor activation" if it is characterized by inappropriate stimulation of MCH receptor, regardless of the amount of MCH present locally, and/or is responsive to modulation of MCH receptor activity. Such conditions include, for example, metabolic disorders (such as diabetes), heart disease, stroke, eating disorders (such as obesity and bulimia nervosa), disorders of the skin such as vitiligo, and sexual disorders such as anorgasmic or psychogenic impotence. These conditions may be diagnosed and monitored using criteria that have been established in the art. In addition, MCH antagonists provided herein may be used to promote weight loss in patients, and MCH agonists provided herein may be used to promote weight gain in patients. Patients may include humans, domesticated companion animals (pets, such as dogs) and livestock animals, with dosages and treatment regimes as described above.

Additional conditions that are associated with MCH receptor activation include:

Cognitive impairment and memory disorders, such as Alzheimer's disease, Parkinson's disease, mild cognitive impairment (MCI), age-related cognitive decline (ARCD), stroke, traumatic brain injury, AIDS associated dementia, and dementia associated with depression, anxiety and psychosis (including schizophrenia and hallucinatory disorders);

Anxiety, depression and other mood disorders, including general anxiety disorder (GAD), agoraphobia, panic disorder with and without agoraphobia, social phobia, specific phobia, post traumatic stress disorder, obsessive compulsive disorder (OCD), dysthymia, adjustment disorders with disturbance of mood and anxiety, separation anxiety disorder, anticipatory anxiety acute stress disorder, adjustment disorders and cyclothymia;

Reward system disorders such as addiction (e.g., opioid, nicotine or alcohol);

Pain such as migraine, peripheral inflammatory pain, neuropathic pain and sympathetic nervous system associated pain; and Peripheral indications such as respiratory disorders (e.g., asthma), urinary disorders (e.g., urinary incontinence), gastrointestinal disorders, reproductive function disorders and cardiovascular disorders (e.g., arteriosclerosis and hypertension).

Frequency of dosage may vary depending on the compound used and the particular disease to be treated or prevented. In general, for treatment of most disorders, a dosage regimen of 4 times daily or less is preferred. For the treatment of eating disorders, including obesity, a dosage regimen of 1 or 2 times daily is particularly preferred. For the treatment of impotence a single dose that rapidly reaches effective concentrations is desirable. It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy. In certain embodiments, administration at meal times is preferred. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Within certain aspects, MCH receptor modulators provided herein may be used within combination therapy for the treatment of conditions associated with MCH receptor modulation. Within combination therapy, a MCH receptor modulator is administered to a patient along with a second therapeutic agent that is not a MCH receptor modulator, but that is appropriate for treatment of the condition(s) of interest. The MCH receptor modulator and second therapeutic agent(s) may be present in the same pharmaceutical composition, or may be administered separately in either order. Suitable second therapeutic agents include those listed above.

Suitable dosages for MCH receptor modulator within such combination therapy are generally as described herein. Dosages and methods of administration of other therapeutic agents can be found, for example, in the manufacturer's instructions in the *Physician's Desk Reference*. In certain embodiments, the combination administration results in a reduction of the dosage of the second therapeutic agent required to produce a therapeutic effect (i.e., a decrease in the minimum therapeutically effective amount). Thus, preferably, the dosage of second therapeutic agent in a combination or combination treatment method of the invention is less than the maximum dose advised by the manufacturer for administration of the second therapeutic agent without combination administration of a MCH receptor modulator. More preferably this dosage is less than ¾, even more preferably less than ½, and highly preferably, less than ¼ of the maximum dose, while most preferably the dose is less than 10% of the maximum dose advised by the manufacturer for administration of the second therapeutic agent(s) when administered without combination administration of a MCH receptor modulator. It will be apparent that the dosage amount of MCH receptor modulator component of the combination needed to achieve the desired effect may similarly be affected by the dosage amount and potency of the second therapeutic agent component of the combination.

In certain preferred embodiments, the combination administration of a MCH receptor modulator with a second therapeutic agent is accomplished by packaging one or more MCH receptor modulators and one or more second therapeutic agents in the same package, either in separate containers within the package or in the same container as a mixture of one or more MCH receptor modulators and one or more second therapeutic agents. Preferred mixtures are formulated for oral administration (e.g., as pills, capsules, tablets or the like). In certain embodiments, the package comprises a label bearing indicia indicating that the one or more MCH receptor modulators and one or more second therapeutic agents are to be taken together for the treatment of a condition that is associated with MCH receptor activation, such as obesity.

In certain embodiments, one or more MCH receptor modulators provided herein are used along with one or more CB1 antagonists within a combination therapy. Such combinations are of particular use for weight management, to reduce appetite and/or food intake or to prevent or treat obesity (e.g., promote weight loss). Patients may include humans, domesticated companion animals (pets, such as dogs) and livestock animals, with dosages and treatment regimes as described above. The MCH receptor modulator(s) may be administered to the patient at the same time as the CB1 antagonist(s) (e.g., as a single dosage unit), or may be administered separately (before or after CB1 antagonist). Within preferred embodiments, the MCH receptor modulator(s) and CB1 antagonist(s) are ultimately simultaneously present at effective concentrations in a body fluid (e.g., blood) of the patient. An effective concentration of MCH receptor modulator or CB1 antagonist is a concentration that is sufficient to reduce one or more of food consumption, appetite and/or body mass index in the patient when repeatedly coadministered as described herein.

Within separate aspects, the present invention provides a variety of in vitro uses for the compounds provided herein. For example, such compounds may be used as probes for the detection and localization of MCH receptors, in samples such as tissue sections, as positive controls in assays for receptor activity, as standards and reagents for determining the ability of a candidate agent to bind to MCH receptor, or as radiotracers for positron emission tomography (PET) imaging or for single photon emission computerized tomography (SPECT). Such assays can be used to characterize MCH receptors in living subjects. Such compounds are also useful as standards and reagents in determining the ability of a potential pharmaceutical to bind to melanin concentrating hormone receptor.

Within methods for determining the presence or absence of MCH receptor in a sample, a sample may be incubated with a compound as provided herein under conditions that permit binding of the compound to MCH receptor. The amount of compound bound to MCH receptor in the sample is then detected. For example, a compound may be labeled using any of a variety of well-known techniques (e.g., radiolabeled with a radionucleide such as tritium, as described herein), and incubated with the sample (which may be, for example, a preparation of cultured cells, a tissue preparation or a fraction thereof). A suitable incubation time may generally be determined by assaying the level of binding that occurs over a period of time. Following incubation, unbound compound is removed, and bound compound detected using any method for the label employed (e.g., autoradiography or scintillation counting for radiolabeled compounds; spectroscopic methods may be used to detect luminescent groups and fluorescent groups). As a control, a matched sample may be simultaneously contacted with radiolabeled compound and a greater amount of unlabeled compound. Unbound labeled and unlabeled compound is then removed in the same fashion, and bound label is detected. A greater amount of detectable label in the test sample than in the control indicates the presence of MCH receptor in the sample. Detection assays, including receptor autoradiography (receptor mapping) of MCH receptors in cultured cells or tissue samples may be performed as described by Kuhar in sections 8.1.1 to 8.1.9 of Current Protocols in Pharmacology (1998) John Wiley & Sons, New York.

Compounds provided herein may also be used within a variety of well-known cell culture and cell separation methods. For example, compounds may be linked to the interior surface of a tissue culture plate or other cell culture support, for use in immobilizing MCH receptor-expressing cells for screens, assays and growth in culture. Such linkage may be performed by any suitable technique, such as the methods described above, as well as other standard techniques. Compounds may also be used to facilitate cell identification and sorting in vitro, permitting the selection of cells expressing a MCH receptor. Preferably, the compound(s) for use in such methods are labeled as described herein. Within one preferred embodiment, a compound linked to a fluorescent marker, such as fluorescein, is contacted with the cells, which are then analyzed by fluorescence activated cell sorting (FACS).

Within other aspects, methods are provided for modulating binding of MCH to an MCH receptor in vitro or in vivo, comprising contacting a MCH receptor with a sufficient amount of a modulator provided herein, under conditions suitable for binding of MCH to the receptor. Preferably, within such methods, MCH binding to receptor is inhibited by the modulator. The MCH receptor may be present in solution, in a cultured or isolated cell preparation or within a patient. Preferably, the MCH receptor is a MCH1R receptor present in the hypothalamus. In general, the amount of compound contacted with the receptor should be sufficient to modulate MCH binding to MCH receptor in vitro within, for example, a binding assay as described in Example 9 and/or a binding assay as described in Example 12. MCH receptor preparations used to determine in vitro binding may be obtained from a variety of sources, such as from HEK 293 cells or Chinese Hamster Ovary (CHO) cells transfected with a MCH receptor expression vector, as described herein.

Also provided herein are methods for modulating the signal-transducing activity of cellular MCH receptors, by contacting MCH receptor, either in vitro or in vivo, with a sufficient amount of a modulator as described above, under conditions suitable for binding of MCH to the receptor. Preferably, within such methods, signal-transducing activity is inhibited by the modulator. The MCH receptor may be present in solution, in a cultured or isolated cell preparation or within a patient. In general, the amount of modulator contacted with the receptor should be sufficient to modulate MCH receptor signal transducing activity in vitro within, for example, a calcium mobilization assay as described in Example 10 and/or an agonist-stimulated GTP gamma$^{35}$S binding assay as described in Example 14. An effect on signal-transducing activity may be assessed as an alteration in the electrophysiology of the cells, using standard techniques, such as intracellular patch clamp recording or patch clamp recording. If the receptor is present in an animal, an alteration in the electrophysiology of the cell may be detected as a change in the animal's feeding behavior.

Preparation of MCH Receptor Modulators

Compounds provided herein may generally be prepared using standard synthetic methods. Starting materials are generally readily available from commercial sources, such as Sigma-Aldrich Corp. (St. Louis, Mo.). For example, a synthetic route similar to that shown in any one of the following Schemes may be used. It will be apparent that the final product and any intermediate(s) shown in the following schemes may be extracted, dried, filtered and/or concentrated, and may be further purified (e.g., by chromatography). Each variable (e.g., "R") in the following Schemes, refers to any group consistent with the description of the compounds provided herein. An individual skilled in the art may find modifications of one or several of the synthetic steps described herein without diverting significantly from the overall synthetic scheme. Further experimental details for synthesis of representative compounds via these schemes are provided in Examples 1-8, herein.

In the following Schemes and elsewhere herein, the following abbreviations are used:
Binap [2,2'-bis(diphenylphosphino)-1,1'-binaphthyl]
BOC t-butoxycarbonyl
BOP benzotriazol-1-yl-oxy-tris(dimethylamino)phosphonium hexafluorophosphate
DBU 1,8-diazabicyclo[5.4.0]undec-7-ene
DCC 1,3-dicyclohexylcarbodiimide
DEAD diethyl azodicarboxylate
DMA dimethylamine
DMAP N,N-dimethyl-4-aminopyridine
DMF dimethylformamide
Et$_3$N triethylamine
EtOAc ethyl acetate
Et$_2$O diethyl ether
EtOH ethanol
Eq equivalent(s)
Fe(acac)$_3$ Iron(III)acetylacetonate
HOAc Acetic acid
HOBt 1-hydroxybenzotriazole
KOtBu potassium tert-butoxide
LDA lithium diisopropylamide
MeOH methanol
NMO 4-methylmorpholine N-oxide
Ph$_3$P triphenylphosphine
Pd(Ph$_3$P)$_4$ tetrakis(triphenylphosphine)palladium(0)
Pd$_2$(dba)$_3$ tris(dibenzylideneacetone)dipalladium(0)
pyBrop bromo-tris-pyrrolidine-phosphonium-hexafluorophosphate
TBDMS tert-butyl-dimethyl-silanyl
TFA trifluoroacetic acid
THF tetrahydrofuran
TLC thin layer chromatography
TPAP tetrapropylammonium perruthenate
h hour(s)
min minute(s)

SCHEME A (REDUCTIVE AMINATION)

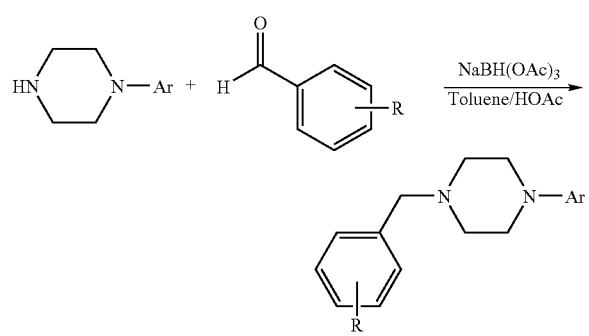

-continued

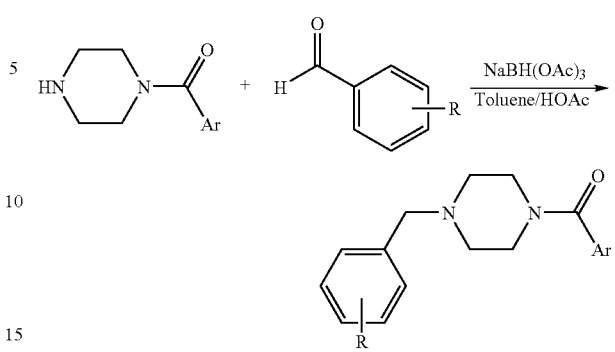

Briefly, one equivalent each of an appropriately substituted piperazine and an appropriately substituted benzaldehyde are reacted under acidic catalysis with an excess of NaBH(OAc)$_3$ under a nitrogen atmosphere until no starting material is detectable by TLC. At that time, the reaction is quenched with saturated aqueous NaHCO$_3$ and extracted with EtOAc to yield the appropriate 1-benzyl-4-substituted piperazine analogue. Extracts may be dried over anhydrous MgSO$_4$, concentrated in vacuo and chromatographed.

SCHEME B (REDUCTIVE AMINATION)

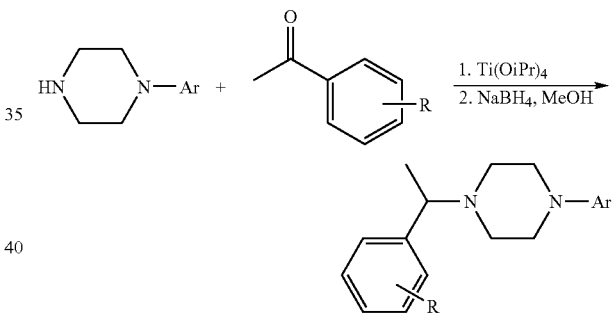

Briefly, one equivalent each of an appropriately substituted piperazine and an appropriately substituted acetophenone are heated with Ti(OiPr)$_4$ (e.g., 70° C. for 2 h). The reaction solution is cooled and after dilution with MeOH, reacted with NaBH$_4$ to yield the 1-benzyl-4-aryl piperazine analogue. The reaction is quenched by the addition of 1 N NaOH and may be extracted with CH$_2$Cl$_2$. CH$_2$Cl$_2$ extracts may be dried over anhydrous MgSO$_4$, concentrated in vacuo, and subjected to chromatography.

SCHEME C
(REDUCTIVE ALKYLATION ALTERNATIVE
TO REDUCTIVE AMINATION)

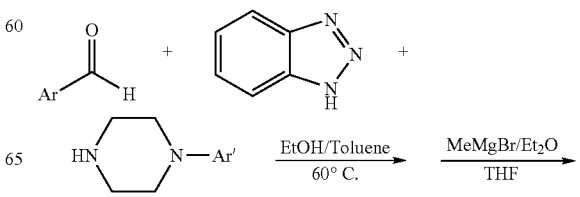

-continued

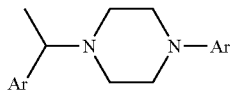

Briefly, a solution containing an appropriately substituted aromatic aldehyde, benzotriazole and an appropriately substituted aromatic piperazine in a mixture of ethanol and toluene is heated and the solution is concentrated. Residue is evaporated with toluene, then dissolved in THF and treated with an excess of methyl magnesium bromide in Et$_2$O to yield the 1-benzyl-4-aryl piperazine analogue.

SCHEME E
(SYNTHESIS OF OCTAHYDRO-PYRIDO[1,2-A] PYRAZINE DERIVATIVES FROM (N$^\alpha$-(T-BUTYLOXYCARBONYL)-β-(BENZYL ESTER)-L-ASPARTIC ACID)

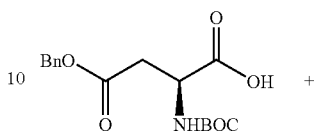

SCHEME D
(SYNTHESIS OF ENANTIOMERICALLY PURE {4-[(R)-1-(4-METHOXY-2,3-DIMETHYL-PHENYL)-ETHYL]-PIPERAZIN-1-YL}DERIVATIVES BY RESOLUTION)

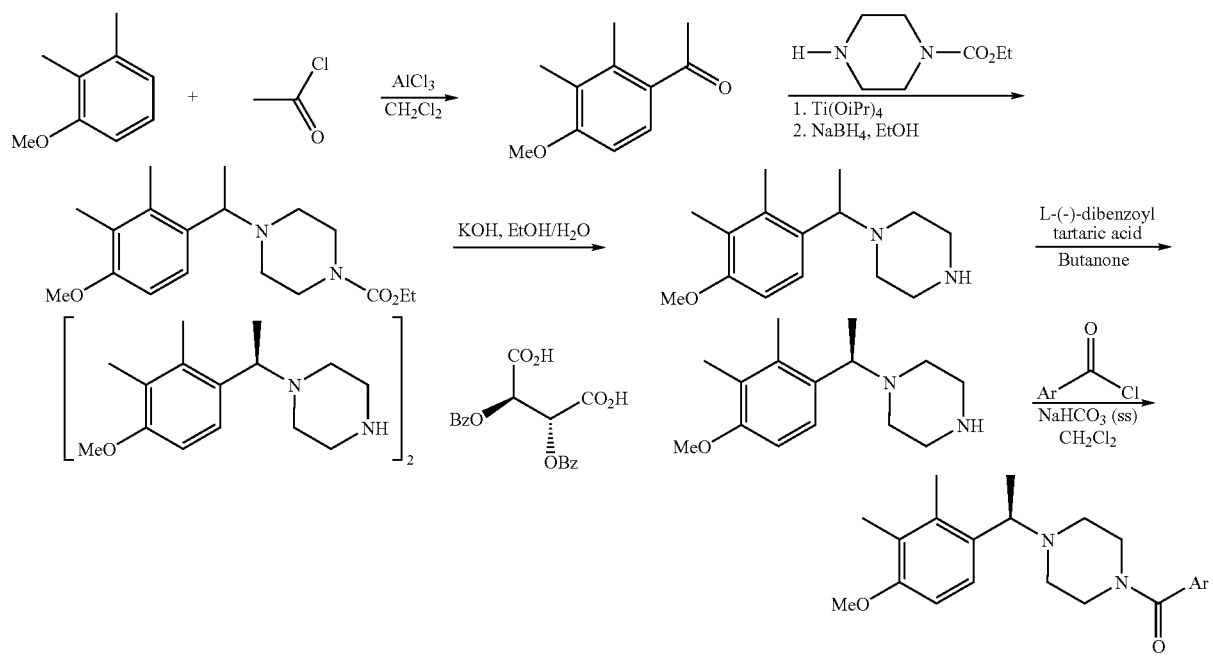

Briefly, 2,3-dimethylanisole is acylated by reaction with acetyl chloride and AlCl$_3$ under Friedel-Crafts reaction conditions to yield 1-(4-methoxy-2,3-dimethyl-phenyl)-ethanone. This is submitted to reductive amination reaction conditions (Scheme B) to produce racemic 4-[1-(4-methoxy-2,3-dimethylphenyl)-ethyl]-piperazine-1-carboxylic acid ethyl ester, which is converted to racemic 1-[1-(4-methoxy-2,3-dimethylphenyl)-ethyl]-piperazine by saponification with a strong base such as LiOH, NaOH, KOH and the like in the presence of a solvent mixture containing water and an alcohol such as methanol, ethanol, isopropanol or n-butanol at temperatures between room temperature and the boiling point of the reaction mixture at atmospheric pressure. The racemic amine is resolved by salt formation, for example with L-(−)-dibenzoyltartaric acid in a solvent such as acetone, butanone, methanol, ethanol, tetrahydrofuran, etc. After converting the enantiomerically pure salt to its free base, acylation reaction with an appropriate acid chloride under Schotten-Bauman reaction conditions yields the corresponding 1-benzyl-4-aroyl piperazine analogue.

-continued

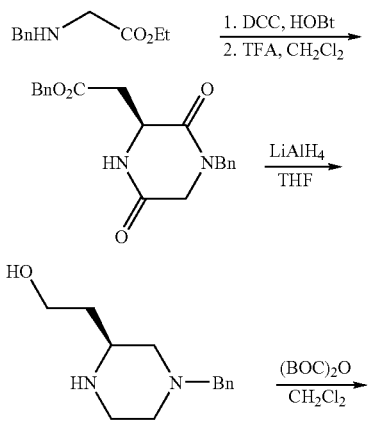

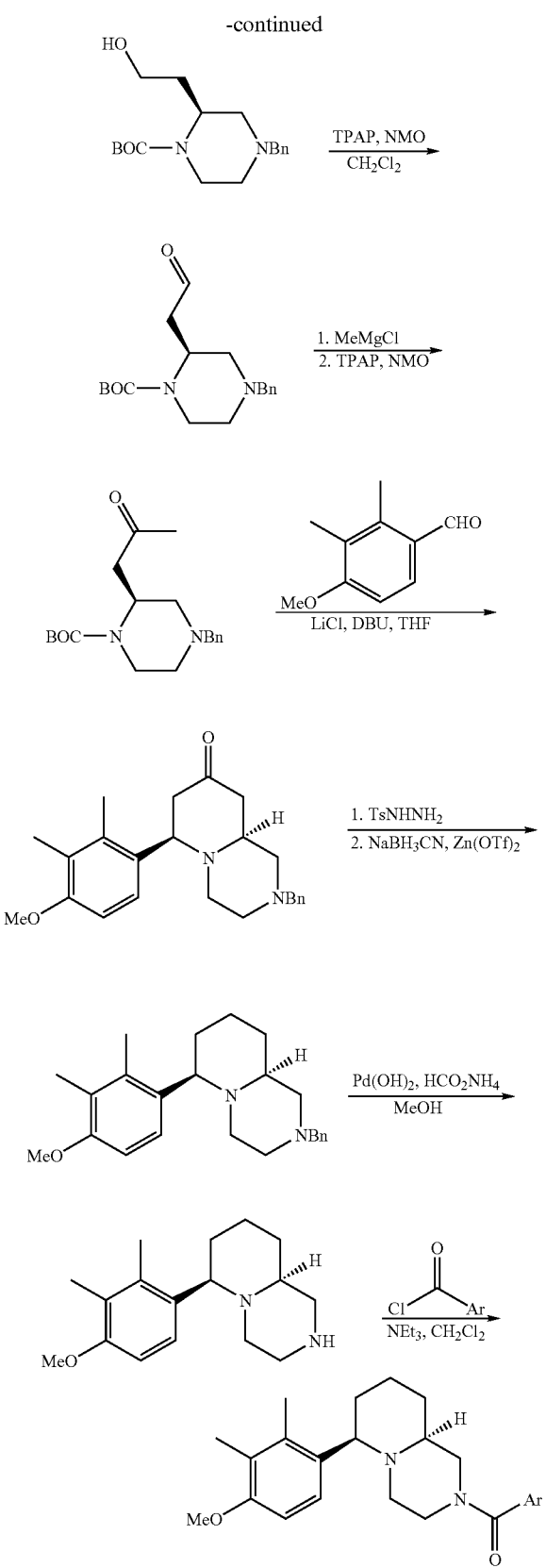

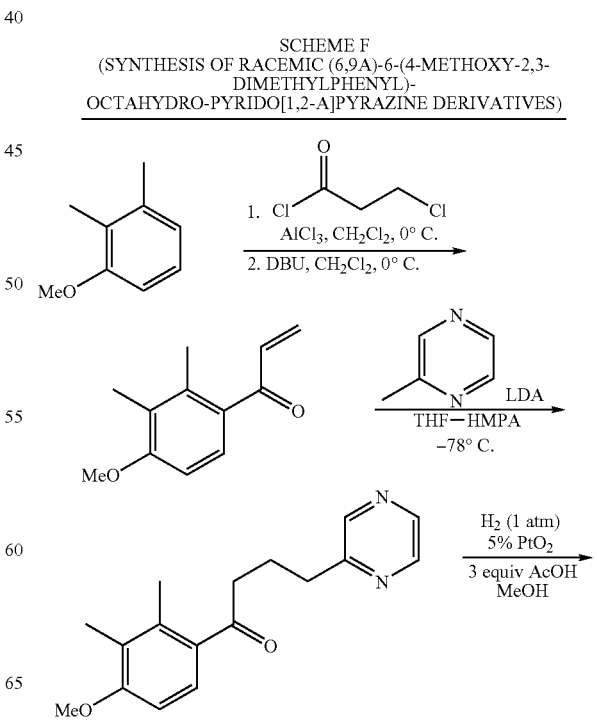

Briefly (and essentially as described in PCT International Publication Numbers WO 98/20001 and WO 99/65922), (Nα-(t-butyloxycarbonyl)-β-(benzyl ester)-L-aspartic acid) is reacted with N-benzylglycine in the presence of DCC and HOBt to produce the corresponding N-benzylglycine amide, which is further reacted with TFA to remove the BOC protecting group, yielding ((S)-4-benzyl-3,6-dioxo-piperazin-2-yl)-acetic acid ethyl ester. This is reduced to 2-((S)-4-benzyl-piperazin-2-yl)-ethanol by reaction with LiAlH$_4$ in THF. Essentially as described in PCT International Publication Number WO 02/094799, the free amine is reacted with (BOC)$_2$O to produce the corresponding carbamate, and the primary alcohol is oxidized with catalytic TPAP in the presence of NMO to the corresponding aldehyde, ((S)-4-benzyl-piperazin-2-yl)-acetaldehyde. This is reacted with MeMgCl under Grignard reaction conditions to produce the secondary alcohol, 1-((S)-4-benzyl-piperazin-2-yl)-propan-2-ol, as a mixture of diastereoisomers, which is oxidized to the corresponding methylketone, 1-((S)-4-benzyl-piperazin-2-yl)-propan-2-one, by reaction with catalytic TPAP and NMO. The methylketone undergoes a tandem aldol condensation/Michael conjugated addition by reaction with 1-(4-methoxy-2,3-dimethylphenyl)-ethanone in the presence of LiCl and DBU as a base in THF as the solvent, yielding bicyclic (6R,9aS)-2-benzyl-6-(4-methoxy-2,3-dimethylphenyl)-octahydro-pyrido[1,2-a]pyrazin-8-one. This is deoxygenated to (6R,9aS)-2-benzyl-6-(4-methoxy-2,3-dimethylphenyl)-octahydro-pyrido[1,2-a]pyrazine by conversion to the corresponding tosylhydrazone and subsequent reduction with NaBH$_3$CN in the presence of zinc triflate. The benzyl group is removed by catalytic transfer hydrogenation reaction promoted by Pd(OH)$_2$ in the presence of excess ammonium formate in MeOH. Finally, (6R,9aS)-6-(4-methoxy-2,3-dimethylphenyl)-octahydro-pyrido[1,2-a]pyrazine is converted to the desired heteroaryl analog by reaction with the corresponding acid chloride under Schotten-Bauman reaction conditions.

SCHEME F
(SYNTHESIS OF RACEMIC (6,9A)-6-(4-METHOXY-2,3-DIMETHYLPHENYL)-OCTAHYDRO-PYRIDO[1,2-A]PYRAZINE DERIVATIVES)

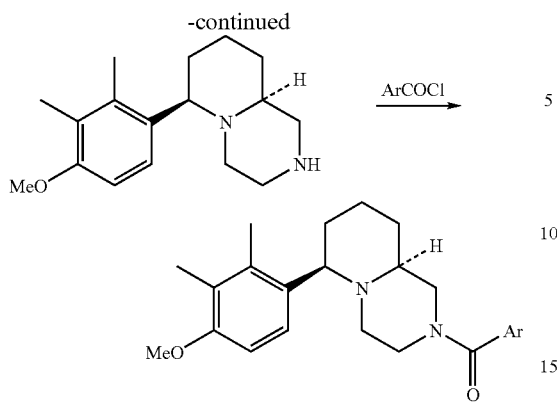

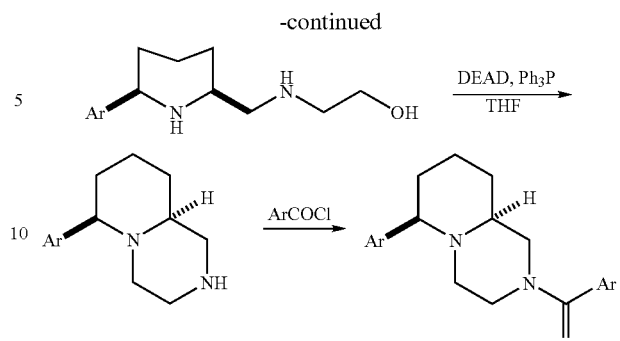

Briefly, 2,3-dimethylanisole is acylated with 3-choropropionyl chloride under Friedel-Crafts reaction conditions in the presence of $AlCl_3$ and the resulting 3-chloro-1-(4-methoxy-2,3-dimethylphenyl)-propan-1-one dehydrochlorinated by treatment with a base such as DBU in a solvent such as but not limited to $CH_2Cl_2$ to produce the vinylic ketone 1-(4-methoxy-2,3-dimethyl-phenyl)-propenone. Michael addition of pyrazinylmethyllithium (obtained by reacting methylpyrazine with LDA in THF) yields 1-(4-methoxy-2,3-dimethyl-phenyl)-4-pyrazin-2-yl-butan-1-one. Transformation to (6,9a)-6-(4-methoxy-2,3-dimethylphenyl)-octahydro-pyrido[1,2-a]pyrazine is accomplished by a one-pot sequence involving catalytic hydrogenation with $H_2$ at atmospheric pressure in the presence of catalytic amounts of Adams catalyst and acetic acid in MeOH as the solvent. Finally, the desired heteroaryl analogue, [(6,9a)-6-(4-methoxy-2,3-dimethylphenyl)-octahydro-pyrido[1,2-a]pyrazin-2-yl]-heteroaryl-methanone, is obtained by reaction with the corresponding acid chloride under Schotten-Bauman reaction conditions.

Briefly, 5-bromopicolinic acid is reacted with thionyl chloride, followed by hydroxyl ethanolamine to yield the corresponding amide, 6-bromopyridine-2-carboxylic acid (2-hydroxy-ethyl)-amide. The amide is then reacted under Suzuki reaction conditions with an aryl boronic acid, KOtBu and catalytic tris(dibenzylideneacetone)-dipalladium(0) until TLC shows no detectable starting material to produce the 6-aryl-pyridine-2-carboxylic acid (2-hydroxy-ethyl)-amide. Reduction of the pyridine ring to the 2,6-cis disubstituted piperidine compound, followed by $LiAlH_4$ reduction of the amide group yields the aminoalcohol 2-[(6-aryl-pyridin-2-ylmethyl)-amino]-ethanol. Intramolecular Mitsunobu reaction is achieved using triphenyl phosphine and diethyl azodicarboxylate, to yield (6,9a)-6-(4-methoxy-2,3-dimethylphenyl)-octahydro-pyrido[1,2-a]pyrazine. Finally, (6,9a)-6-(4-methoxy-2,3-dimethylphenyl)-octahydro-pyrido[1,2-a]pyrazine is converted to the desired heteroaroyl analog by reaction with the corresponding acid chloride under Schotten-Bauman reaction conditions.

SCHEME G
(RACEMIC SYNTHESIS OF
OCTAHYDRO-PYRIDO[1,2-A]PYRAZINE
DERIVATIVES VIA SUZUKI ROUTE)

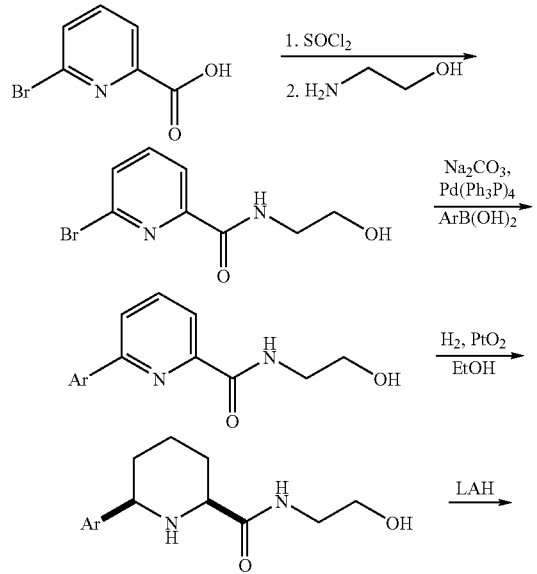

SCHEME H
(SYNTHESIS OF OCTAHYDRO-PYRROLO[1,2-A]PYRAZINE
DERIVATIVES VIA 6,5 BICYCLE SYNTHESIS)

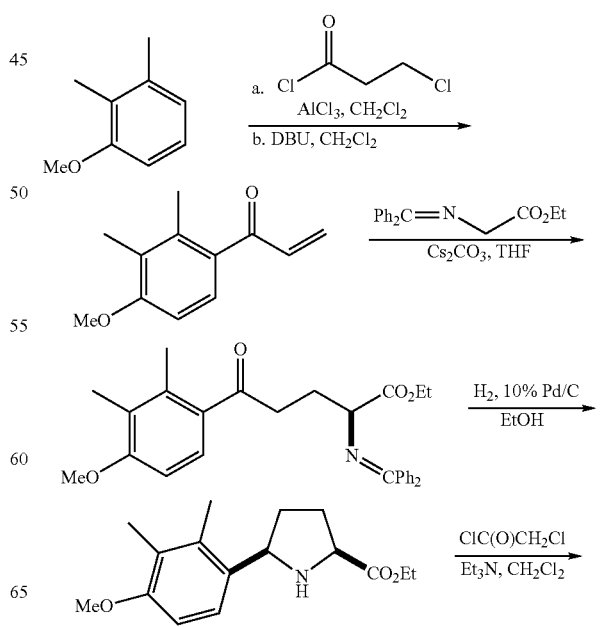

-continued

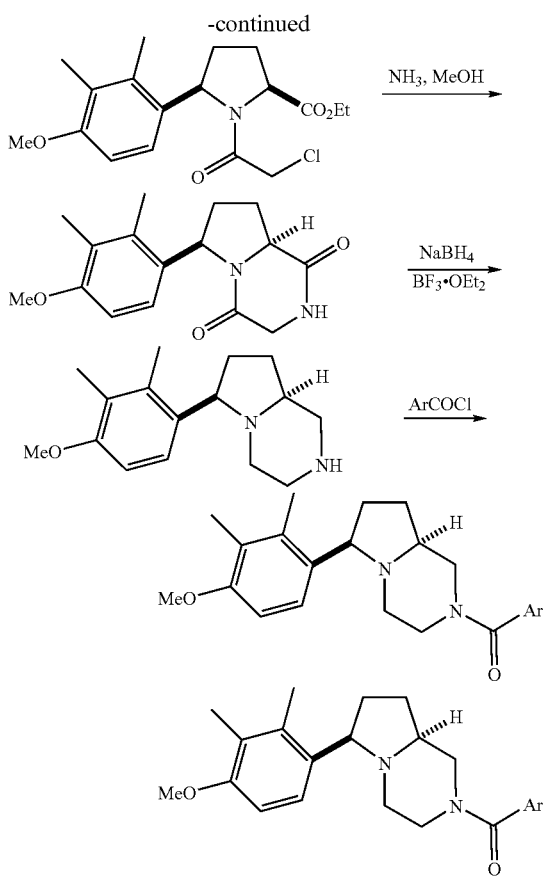

Briefly, 2,3-dimethylanisole is acylated with 3-choropropionyl chloride under Friedel-Crafts reaction conditions in the presence of AlCl₃ and the resulting 3-chloro-1-(4-methoxy-2,3-dimethylphenyl)-propan-1-one dehydrochlorinated by treatment with a base such as DBU in a solvent such as but not limited to CH₂Cl₂ to produce the vinylic ketone 1-(4-methoxy-2,3-dimethyl-phenyl)-propenone. Michael addition of (benzhydrylidene-amino)-acetic acid ethyl ester in the presence of Cs₂CO₃ as a base yields 2-(benzhydrylidene-amino)-5-(4-methoxy-2,3-dimethyl-phenyl)-5-oxo-pentanoic acid ethyl ester. Upon hydrogenolysis with H₂ in the presence of catalytic Pd10%/C in ethanol as the solvent this cyclizes to 2,5-cis-5-(4-methoxy-2,3-dimethylphenyl)-pyrrolidine-2-carboxylic acid ethyl ester, which reacts with chloroacetyl chloride in the presence of Et₃N in a solvent such as but not limited to CH₂Cl₂ to furnish 2,5-cis-1-(2-chloro-acetyl)-5-(4-methoxy-2,3-dimethylphenyl)-pyrrolidine-2-carboxylic acid ethyl ester. Upon treatment with ammonia in alcohol the chloroamide cyclizes to the corresponding cis-(6,8a)-6-(4-methoxy-2,3-dimethylphenyl)-hexahydro-pyrrolo[1,2-a]pyrazine-1,4-dione, which is reduced to cis-(6,8a)-6-(4-methoxy-2,3-dimethylphenyl)-octahydro-pyrrolo[1,2-a]pyrazine by treatment with NaBH₄ in the presence of BF₃.OEt₂. Finally, the desired heteroaryl analogue, cis-[(6,8a)-6-(4-methoxy-2,3-dimethylphenyl)-hexahydro-pyrrolo[1,2-a]pyrazin-2-yl]-aryl-methanone is obtained by reaction with the corresponding acid chloride under Schotten-Bauman reaction conditions.

In certain situations, compounds of the present invention may contain one or more asymmetric carbon atoms, so that the compounds can exist in different stereoisomeric forms. These compounds can be, for example, racemates or optically active forms. As noted above, all stereoisomers are encompassed by the present invention. Nonetheless, it may be desirable to obtain single enantiomers (i.e., optically active forms). Standard methods for preparing single enantiomers include asymmetric synthesis and resolution of the racemates. Resolution of the racemates can be accomplished, for example, by conventional methods such as crystallization in the presence of a resolving agent, or chromatography using, for example a chiral HPLC column. As noted above, for compounds having an alpha-methyl benzyl group (R₃ is methyl, R₄ is hydrogen) the R enantiomer is generally preferred. Asymmetric synthesis of such compounds may be performed using the methods illustrated in Scheme D.

Compounds may be labeled by carrying out their synthesis using precursors comprising at least one atom that is an isotope. Each isotope is preferably carbon (e.g., $^{14}C$), hydrogen (e.g., $^{3}H$ or $^{2}H$), fluorine (e.g., $^{18}F$), sulfur (e.g., $^{35}S$) or iodine (e.g., $^{125}I$). Tritium labeled compounds may also be prepared catalytically via platinum-catalyzed exchange in tritiated acetic acid, acid-catalyzed exchange in tritiated trifluoroacetic acid, or exchange with tritium gas under heterogeneous catalysis using the compound as substrate. In addition, certain precursors may be subjected to tritium-halogen exchange with tritium gas, tritium gas reduction of unsaturated bonds, or reduction using sodium borotritide, as appropriate. Preparation of radiolabeled compounds may be conveniently performed by a radioisotope supplier specializing in custom synthesis of radiolabeled probe compounds.

The following Examples illustrate the synthesis of representative substituted 1-benzyl-4-aryl piperazine analogues. It will be apparent that, through variation of starting compounds, these methods may be used to prepare a wide variety of such compounds.

EXAMPLES

Example 1

Preparation of {(6R,9AS)-6-(2,3-DIMETHYL-4-PROPOXYPHENYL)-HEXAHYDRO-1H-PYRIDO[1,2-A]PYRAZIN-2(6H)-YL}-(6-(TRIFLUOROMETHYL)PYRIDIN-3-YL)METHANONE

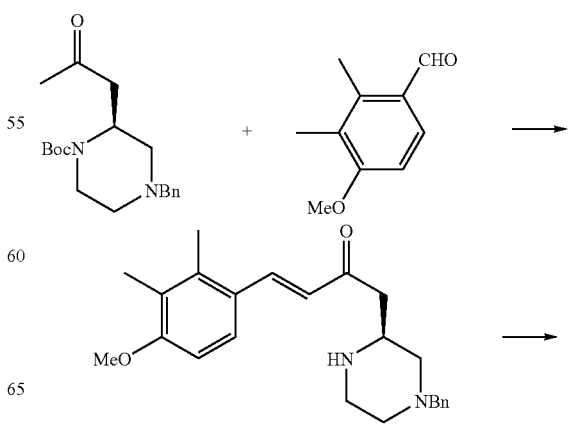

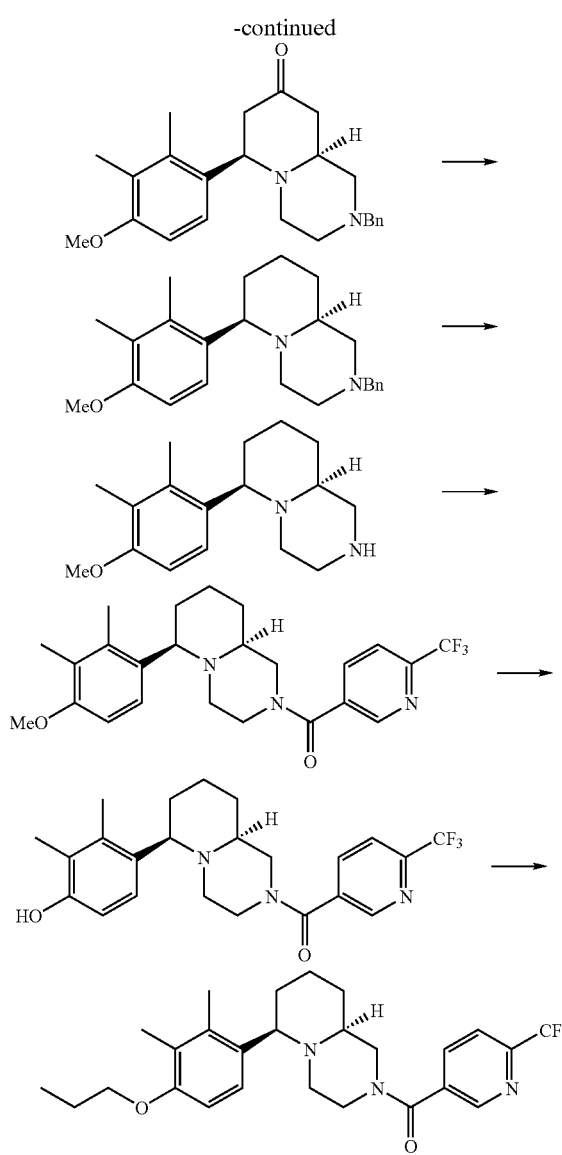

Step 1. (E)-1-((S)-4-benzyl-piperazin-2-yl)-4-(4-methoxy-2,3-dimethylphenyl)-but-3-en-2-one (S)-4-benzyl-2-(2-oxopropyl)-piperazine-1-carboxylic acid tert-butyl ester (15.0 g, 45.0 mmol), 2,3-dimethylanisaldehyde (8.9 g, 54.0 mmol, 1.2 eq), and lithium chloride (9.6 g, 226.0 mmol, 5.0 eq) are stirred together in 225 mL of anhydrous THF under a nitrogen atmosphere for 40 min at ambient temperature to effect dissolution of the lithium chloride. This solution is cooled to 0° C. and treated with DBU (7.45 mL, 49.8 mmol, 1.1 eq), which is added slowly, dropwise via syringe. The mixture is stirred and allowed to slowly warm to ambient temperature. After 22 h, the mixture is diluted with 200 mL water and extracted with EtOAc (3×200 mL). The combined organic extracts are dried over $Na_2SO_4$, filtered, and concentrated in vacuo to provide 23.0 g the Boc-protected enone as a mixture of cis- and trans-isomers, which is used without purification. LCMS: Rt: 2.69 min, 479.31 (M+1). This material is dissolved in 225 mL of MeOH and 52.5 mL of 6N HCl and heated in a 60° C. oil bath for 3 h. After cooling, the solution is concentrated in vacuo. The residue is suspended in about 150 mL additional MeOH and reconcentrated. This is repeated four times to remove the water, leaving the desired crude enone as a red solid, which is used without purification. LC/MS: 379 (M+1).

Step 2. (6R,9aS)-2-benzyl-6-(4-methoxy-2,3-dimethylphenyl)-octahydro-pyrido[1,2-a]pyrazin-8-one The crude enone from step 1 is dissolved in 300 mL MeOH and treated with 160 mL of 2M ammonium acetate. The mixture is stirred at ambient temperature for 14.5 h, then at 60° C. for 2 h. The MeOH is removed in vacuo and the aqueous residue extracted with $CH_2Cl_2$ (3×250 mL). The combined extracts are dried over $Na_2SO_4$, filtered and concentrated. The residue is purified by flash chromatography on silica gel using 80%-60% hexanes/EtOAc as eluent to afford (6R,9aS)-2-benzyl-6-(4-methoxy-2,3-dimethylphenyl)-octahydro-pyrido[1,2-a]pyrazin-8-one as a white foam. LC/MS: 379 (M+1). $^1$H NMR (400 MHz, $CDCl_3$): 7.79 (6H, m), 6.73 (1H, m), 3.80 (3H, s), 3.70 (1H, bs), 3.50 (2H, dd), 3.19 (1H, m), 2.79-2.28 (7H, bm), 2.25-1.94 (9H, bm).

Step 3. (6R,9aS)-2-Benzyl-6-(4-methoxy-2,3-dimethylphenyl)-octahydro-pyrido[1,2-a]pyrazine (6R,9aS)-2-benzyl-6-(4-methoxy-2,3-dimethylphenyl)-octahydro-pyrido[1,2-a]pyrazin-8-one (9.48 g, 25.0 mmol) is stirred with p-toluenesulfonyl hydrazide (5.60 g, 30.0 mmol, 1.2 eq) in 40 mL anhydrous THF and 200 mL anhydrous MeOH for 20 h at ambient temperature under a nitrogen atmosphere. LC/MS analysis indicates complete conversion to the p-toluenesulfonyl hydrazone. The solution is sparged with argon for 30 min and then treated with 50 mL of a 1.5 M solution of $NaCNBH_3$ in MeOH. Zinc trifluoromethanesulfonate (140 mg, 0.376 mmoles, 1.5%) is added and the solution is heated in a 65° C. oil bath for 5.5 h under an argon balloon. LC/MS analysis indicates consumption of the hydrazone. The mixture is allowed to cool and is quenched with 500 mL of saturated $NaHCO_3$. After stirring vigorously for 30 min, the mixture is extracted with $CH_2Cl_2$ (4×200 mL). The combined extracts are dried over $Na_2SO_4$, filtered and concentrated in vacuo. The residue is purified by column chromatography on silica gel eluting with 90%-80% hexanes/EtOAc to yield (6R,9aS)-2-Benzyl-6-(4-methoxy-2,3-dimethylphenyl)-octahydro-pyrido[1,2-a]pyrazine as an oil. LC/MS: 365 (M+1). $^1$H NMR (400 MHz, $CDCl_3$): 7.34 (1H, d), 7.27 (5H, m), 6.72 (1H, d), 3.79 (3H, s), 3.47 (2H, dd), 3.28 (1H, d), 2.68 (3H, m), 2.28-2.04 (8H, bm), 1.98-1.88 (2H, bm), 1.75 (1H, m), 1.59 (1H, d), 1.50-1.30 (4H, bm).

Step 4. (6R,9aS)-6-(4-Methoxy-2,3-dimethylphenyl)-octahydro-pyrido[1,2-a]pyrazine A solution containing the compound obtained in step 3 (2.66 g, 7.30 mmol) and ammonium formate (6.90 g, 109.50 mmol, 15 eq) is treated with 665 mg of 20% palladium hydroxide on carbon, and heated at reflux under a nitrogen balloon for 2 h. The mixture is filtered through a CELITE pad. The pad is washed with 200 mL of chloroform and the solution is concentrated in vacuo. The residue is taken up in 200 mL dichloromethane and washed with 1N NaOH, water and brine (75 mL each) to remove any residual ammonium formate. The organic solution is concentrated in vacuo to afford (6R,9aS)-6-(4-methoxy-2,3-dimethylphenyl)-octahydro-pyrido[1,2-a]pyrazine as an amber colored oil which is used in the next step with no further purification. LC/MS: 275 (M+1). $^1$H NMR (400 MHz, CDCl$_3$): 7.36 (1H, dd), 6.74 (1H, dd), 4.50 (1H, dd), 3.80 (3H, s), 3.28 (1H, d), 2.86 (1H, dd), 2.78 (2H, m), 2.67-2.55 (3H, m), 2.22 (3H, s), 2.17 (3H, s), 1.78-1.67 (4H, bm), 1.56-1.31 (4H, bm).

Step 5. [(6R,9aS)-6-(4-Methoxy-2,3-dimethylphenyl)-octahydro-pyrido[1,2-a]pyrazin-2-yl]-(6-trifluoromethyl-pyridin-3-yl)-methanone A magnetically stirred suspension of 6-trifluoromethyl nicotinic acid (1.54 g, 8.07 mmol) in 50 mL of anhydrous CH$_2$Cl$_2$ (0.16M), under nitrogen, is treated with oxalyl chloride (2M in CH$_2$Cl$_2$, 10.0 mL, 20.0 mmol, 2.5 eq) followed by the careful dropwise addition of 250 μL of DMF. Vigorous gas evolution ensues and the mixture becomes homogeneous. The solution is stirred at ambient temperature for 1.5 h, and then concentrated in vacuo to produce the acid chloride as a white solid. This was suspended in toluene and concentrated again and used with no further purification.

A solution of (6R,9aS)-6-(4-methoxy-2,3-dimethylphenyl)-octahydro-pyrido[1,2-a]pyrazine (1.77 g, 6.45 mmol) in anhydrous CH$_2$Cl$_2$ (50 mL) is treated with Et$_3$N (1.4 mL, 10.08 mmol) and DMAP (78.8 mg, 0.65 mmol). This mixture is stirred under nitrogen and treated with a solution of the previously prepared acid chloride in 10 mL CH$_2$Cl$_2$ (an additional 5 mL is used as a rinse). The mixture is stirred at ambient temperature for 18 h and quenched by the addition of 80 mL 50% saturated NaHCO$_3$. The phases are separated and the aqueous phase is extracted twice with CH$_2$Cl$_2$. The combined extracts are dried over Na$_2$SO$_4$, filtered, and concentrated in vacuo. The residue is purified using flash chromatography on silica gel eluting with 70%-60% hexanes/EtOAc to give [(6R,9aS)-6-(4-methoxy-2,3-dimethylphenyl)-octahydro-pyrido[1,2-a]pyrazin-2-yl]-(6-trifluoromethyl-pyridin-3-yl)-methanone as a white foam. LC/MS: 448 (M+1). $^1$H NMR (mixture of rotamers, 400 MHz, CDCl$_3$): 8.74 (1H, d), 7.90 (1H, dd), 7.76 (1H, dd), 7.34 (1H, dd), 6.74 (1H, dd), 4.50 (1H, dd), 3.79 (3H, d), 3.42-3.32 (2H, bm), 3.23-3.00 (1H, m), 2.91-2.53 (3H, bm), 2.21-2.14 (6H, m), 1.90-1.74 (4H, bm), 1.52-1.30 (3H, bm).

Step 6. [(6R,9aS)-6-(4-Hydroxy-2,3-dimethylphenyl)-octahydro-pyrido[1,2-a]pyrazin-2-yl]-(6-trifluoromethyl-pyridin-3-yl)-methanone A CH$_2$Cl$_2$ solution of [(6R,9aS)-6-(4-methoxy-2,3-dimethylphenyl)-octahydro-pyrido[1,2-a]pyrazin-2-yl]-(6-trifluoromethyl-pyridin-3-yl)-methanone obtained in step 5 (2.30 g, 5.14 mmoles) is treated with 15.4 mL of HCl (1 M in Et$_2$O) and allowed to stand for 10 min. This solution is concentrated in vacuo and then dissolved in 70 mL anhydrous CH$_2$Cl$_2$. This solution is cooled to −70° C. (dry ice/isopropanol bath) under nitrogen and treated with BBr$_3$ (1 M in DCM, 20.6 mL) dropwise via syringe over 20 mins. The mixture is stirred for 18 h while warming to ambient temperature. After this time, the mixture is cooled to 0° C., treated with 150 mL saturated NaHCO$_3$ and stirred vigorously for 30 min. The phases are separated and the aqueous phase is extracted three times with CH$_2$Cl$_2$. The combined extracts are dried over Na$_2$SO$_4$, filtered and concentrated in vacuo to afford [(6R,9aS)-6-(4-hydroxy-2,3-dimethylphenyl)-octahydro-pyrido[1,2-a]pyrazin-2-yl]-(6-trifluoromethyl-pyridin-3-yl)-methanon as a light brown solid which is used without additional purification. LC/MS: 434 (M+1). $^1$H NMR (mixture of rotamers, 400 MHz, CDCl$_3$): 8.74 (1H, d), 7.94 (1H, dd), 7.88 (1H, dd), 7.22 (1H, dd), 6.64 (1H, dd), 4.92 (1H, bs), 4.50 (1H, dd), 3.41-3.30 (2H, bm), 3.21 (1H, m), 3.03 (1H, m), 2.91-2.53 (3H, bm), 2.25-2.14 (6H, m), 1.92-1.58 (5H, bm), 1.20-1.32 (3H, bm).

Step 7. {(6R,9aS)-6-[4-(2-Methoxy-ethoxy)-2,3-dimethylphenyl]-octahydro-pyrido[1,2-a]pyrazin-2-yl}-(6-trifluoromethyl-pyridin-3-yl)-methanone A solution of [(6R,9aS)-6-(4-hydroxy-2,3-dimethylphenyl)-octahydro-pyrido[1,2-a]pyrazin-2-yl]-(6-trifluoromethyl-pyridin-3-yl)-methanone (1.54 g, 3.55 mmol) in CH$_3$CN is treated with powdered KOH (400 mg, 7.10 mmol, 1.5 eq) and 1-bromopropane (5.33 mmol, 2.0 eq) and heated in a sealed tube reactor with stirring in a 60° C. oil bath for 20.5 h. After cooling, the mixture is filtered through a CELITE pad. The pad is washed with CH$_2$Cl$_2$ and the solution is concentrated in vacuo. The residue is purified by flash chromatography on silica gel eluting with 50%-40% hexanes/EtOAc to yield {(6R,9aS)-6-(2,3-dimethyl-4-propoxyphenyl)-hexahydro-1H-pyrido[1,2-a]pyrazin-2(6H)-yl}-(6-(trifluoromethyl)pyridin-3-yl)methanone. LC/MS: 476 (M+1).

The material is dissolved in EtOAc, treated with one equivalent of HCl (1M in Et$_2$O) and allowed to stand for 10 min. The mixture is concentrated in vacuo to afford the desired product (monohydrochloride salt).

Example 2

Preparation of [(6R,9AS)-6-(4-ETHOXY-2,3-DIMETHYL-PHENYL)-OCTAHYDRO-PYRIDO[1,2-A]PYRAZIN-2-YL]-(6-TRIFLUOROMETHYL-PYRIDIN-3-YL)-METHANONE

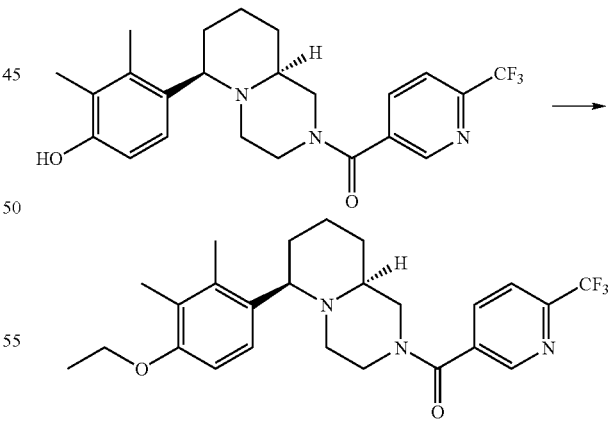

A solution of [(6R,9aS)-6-(4-hydroxy-2,3-dimethylphenyl)-octahydro-pyrido[1,2-a]pyrazin-2-yl]-(6-trifluoromethyl-pyridin-3-yl)-methanone (100 mg, 0.23 mmoles) in CH$_3$CN is treated with powdered KOH (26 mg, 0.461 mmoles, 2.0 equiv.) and 1-bromoethane (0.46 mmol) and heated in a sealed tube with stirring in a 60° C. oil bath for 7 h and then allowed to stand at ambient temperature for 19 h. The mixture is filtered through a CELITE pad, the pad is washed with DCM and the solution is concentrated in vacuo. The residue is purified by preparative thin layer chromatography on a 2 mm silica plate eluting with 60% hexanes/EtOAc to yield the title compound. LC/MS: 462 (M+1).

Example 3

Preparation of [(6R,8AS)-6-(4-METHOXY-2,3-DIMETHYLPHENYL)-HEXAHYDRO-PYRROLO[1,2-A]PYRAZIN-2-YL]-(6-TRIFLUOROMETHYL-PYRIDIN-3-YL)-METHANONE

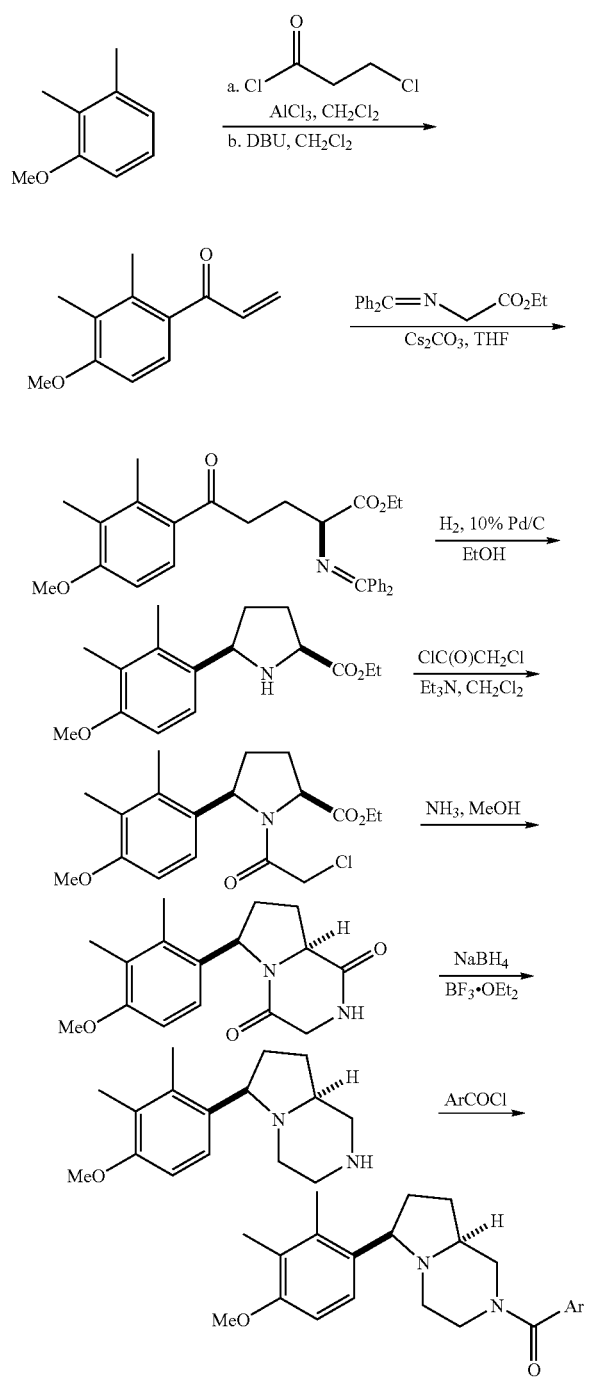

Step 1. Preparation of 3-chloro-1-(4-methoxy-2,3-dimethylphenyl)propan-1-one

3-Chloropropionyl chloride (12.70 g, 100 mmol) is slowly added to a suspension of AlCl$_3$ (16.0 g, 120 mmol) in CH$_2$Cl$_2$ (200 mL) at 0° C. under N$_2$. Next, 2,3-dimethylanisole (13.62 g, 100 mmol) is slowly added at 0° C. The resulting yellow solution is stirred at 0° C. for 30 min, and then quenched by the addition of ice-cold 1.0 N HCl (200 mL) (the first several mL are added very slowly). The resulting mixture is stirred at room temperature for 20 min and then extracted with CH$_2$Cl$_2$. The extract is washed again with water (100 mL) and brine (100 mL), dried over Na$_2$SO$_4$, and concentrated in vacuo to a yield white solid. $^1$H NMR (CDCl$_3$, 400 MHz): 7.50 (d, J=8.6 Hz, 1H), 6.74 (d, J=8.6 Hz, 1H), 3.90 (t, J=6.8 Hz, 2H), 3.87 (s, 3H), 3.34 (t, J=6.8 Hz, 2H), 2.41 (s, 3H), 2.18 (s, 3H).

Step 2. 1-(4-methoxy-2,3-dimethylphenyl)propenone

The crude 3-chloro-1-(4-methoxy-2,3-dimethylphenyl)propan-1-one is redissolved in CH$_2$Cl$_2$ (200 mL). The resulting solution is cooled to 0° C. and treated with DBU (15.0 mL, 100 mmol). After 30 min, additional DBU (0.75 mL, 5 mmol) is added. After an additional 15 min, the reaction mixture is concentrated in vacuo. The residue is partitioned between Et$_2$O and water 150 mL. The layers are separated, and the Et$_2$O extract is washed with additional water (100 mL) and brine (100 mL). The aqueous washes are reextracted once with Et$_2$O, and the combined extracts are dried over Na$_2$SO$_4$ and concentrated to a light yellow oil. $^1$H NMR (CDCl$_3$, 400 MHz): 7.33 (d, J=8.4 Hz, 1H), 6.78 (dd, J=17.4, 10.6 Hz, 1H), 6.73 (d, J=8.4 Hz, 1H), 6.14 (dd, J=17.4, 1.4 Hz, 1H), 5.94 (dd, J=10.4, 1.6 Hz, 1H), 3.86 (s, 3H), 2.33 (s, 3H), 2.18 (s, 3H).

Step 3. Preparation of 2-(benzhydrylideneamino)-5-(4-methoxy-2,3-dimethylphenyl)-5-oxopentanoic acid ethyl ester Cs$_2$CO$_3$ (0.51 g, 1.58 mmol) is added to a solution 1-(4-methoxy-2,3-dimethylphenyl)propenone (3.15 g, 16.56 mmol) and N-(diphenylmethylene)glycine ethyl ester (4.22 g, 15.77 mmol) in THF (40 mL) at 0° C. is added. After 5 min, the ice bath is removed, and the reaction mixture is stirred at room temperature overnight. The reaction mixture is then diluted with Et$_2$O and washed with water (1×50 mL) and brine (1×50 mL). The aqueous washes are reextracted once with Et$_2$O, and the combined extracts are dried over Na$_2$SO$_4$ and concentrated. The crude oil is purified by flash column chromatography on silica gel. Elution with 4:1 hexanes-EtOAc affords 2-(benzhydrylideneamino)-5-(4-methoxy-2,3-dimethylphenyl)-5-oxopentanoic acid ethyl ester as a colorless syrup. $^1$H NMR (CDCl$_3$, 400 MHz): 7.64 (m, 2H), 7.48 (d, J=8.8 Hz, 1H), 7.43-7.37 (m, 4H), 7.32 (m, 2H), 7.15 (m, 2H), 6.69 (d, J=8.8 Hz, 1H), 4.20-4.13 (m, 3H), 3.85 (s, 3H), 2.93 (t, J=7.6 Hz, 2H), 2.31 (m, 2H), 2.31 (s, 3H), 2.16 (s, 3H), 1.25 (t, J=7.0 Hz, 3H). Electrospray MS: m/z 458 [M+1].

Step 4. Preparation of cis-5-(4-methoxy-2,3-dimethylphenyl)pyrrolidine-2-carboxylic acid ethyl ester A solution of 2-(benzhydrylideneamino)-5-(4-methoxy-2,3-dimethylphenyl)-5-oxopentanoic acid ethyl ester (16.56 mmol) in EtOH (80 mL) containing 10% Pd/C (760 mg) is stirred under an atmosphere of H$_2$ (double-stuffed balloon) for 18 h. The reaction mixture is then filtered through of pad of Celite using MeOH for the rinse. The filtrated is concentrated in vacuo to a nearly colorless syrup, which is used in the next reaction without further purification. $^1$H NMR (CDCl$_3$, 400 MHz): 7.46 (d, J=8.6 Hz, 1H), 6.75 (d, J=8.6 Hz, 1H), 4.40 (dd, J=8.8, 6.6 Hz, 1H), 4.23 (q, J=8.8 Hz, 2H), 3.90 (dd, J=8.6, 5.4 Hz, 1H), 3.82 (s, 3H), 2.29 (s, 3H), 2.19 (s, 3H), 2.25-2.05 (m, 4H), 1.72-1.65 (m, 1H), 1.31 (t, J=8.8 Hz, 3H). Electrospray MS: m/z 278 [M+1].

Step 5. Preparation of cis-1-(2-chloroacetyl)-5-(4-methoxy-2,3-dimethylphenyl)pyrrolidine-2-carboxylic acid ethyl ester Chloroacetyl chloride (1.7 mL, 21.5 mmol) To a solution of cis-5-(4-methoxy-2,3-dimethylphenyl)pyrrolidine-2-carboxylic acid ethyl ester (16.56 mmol) and Et$_3$N (3.5 mL, 24.8 mmol) in CH$_2$Cl$_2$ (80 mL) at 0° C. The reaction mixture is stirred at 0° C. for 15 min and then at room temperature for 45 min. The mixture then poured into half-saturated aq. NaHCO$_3$ (100 mL) and extracted with EtOAc. The extract is further washed with water (1×50 mL) and brine (1×50 mL). The aqueous washes are reextracted once with EtOAc, and the combined extracts are dried over Na$_2$SO$_4$, and concentrated. The crude material is used in the next step without further purification. $^1$H NMR (CDCl$_3$, 400 MHz): 7.90 (d, J=8.6 Hz, 1H), 6.78 (d, J=8.6 Hz, 1H), 5.30 (dd, J=7.6, 3.6 Hz, 1H), 4.53 (t, J=8.0 Hz, 1H), 4.37-4.21 (m, 2H), 3.81 (s, 3H), 3.77, 3.65 (ABq, J=13.2 Hz, 2H), 2.50-2.41 (m, 1H), 2.26 (s, 3H), 2.24-2.14 (m, 1H), 2.19 (s, 3H), 2.09-2.00 (m, 1H), 1.96-1.89 (m, 1H), 1.35 (t, J=7.2 Hz, 3H). Electrospray MS: m/z 354 [M+1].

Step 6. Preparation of cis-6-(4-methoxy-2,3-dimethylphenyl)hexahydropyrrolo[1,2-a]pyrazine-1,4-dion A mixture of the crude cis-1-(2-chloroacetyl)-5-(4-methoxy-2,3-dimethyl-phenyl)pyrrolidine-2-carboxylic acid ethyl ester (~16.56 mmol) and ca. 7 M NH$_3$ in MeOH (50 mL) is stirred in a sealed flask at room temperature for 2.5 days. The mixture is then diluted with water (ca. 200-300 mL). The resulting suspension is cooled to 0° C. and stirred well. The mixture is then filtered and the solid thoroughly washed with water followed by Et$_2$O. Drying affords cis-6-(4-methoxy-2,3-dimethylphenyl)hexahydropyrrolo[1,2-a]pyrazine-1,4-dione as a slightly off-white powder. $^1$H NMR (CDCl$_3$, 400 MHz): 6.70 (br, 1H), 6.68 (d, J=8.6 Hz, 1H), 6.64 (d, J=8.6 Hz, 1H), 5.38 (d, J=8.8 Hz, 1H), 4.29 (dd, J=10.8, 6.4 Hz, 1H), 4.10, 3.93 (ABXq, J$_{AB}$=16.8 Hz, J$_{AX}$=1.0 Hz, J$_{BX}$=4.8 Hz, 2H), 3.77 (s, 3H), 2.43-2.31 (m, 1H), 2.26 (s, 3H), 2.24-2.11 (m, 2H), 2.16 (s, 3H), 1.85 (dd, J=12.2, 5.8 Hz, 1H). Electrospray MS: m/z 289 [M+1].

Step 7. Preparation of cis-6-(4-methoxy-2,3-dimethylphenyl)octahydropyrrolo[1,2-a]pyrazine The di-ketopiperazine from step 5 is dissolved in 1,2-dimethoxyethane (30 mL) at room temperature. NaBH$_4$ (0.158 g, 4.18 mmol) is added in one portion, followed by BF$_3$.OEt$_2$ (350 µL, 2.51 mmol). The mixture is heated at reflux temperature (ca. 90° C.) for 3 h and then cooled to 0° C. The reaction is quenched by addition of MeOH (50 mL) and then HCl (conc., 35 mL). The resulting solution is stirred at room temperature for 20 min and then at reflux temperature for 45 min. The organic solvents are evaporated under reduced pressure and the residue is taken with NaOH 1N. Extractive work-up with EtOAc washing with brine, drying with MgSO$_4$, filtration and concentration under reduced pressure affords the desired amine as an oil. Purification is carried out by flash chromatography on silicagel eluting with EtOAc to produce the title compound as a while solid. $^1$H NMR (400 MHz, CDCl$_3$): 7.3 (br, 1H), 6.7 (br, 1H), 4.8 (br, 1H), 3.8 (s, 3H), 3.6 (br, 1H), 3.4 (d, 1H), 3.2 (d, 1H), 2.9 (m, 2H), 2.8 (t, 1H), 2.4 (br, 1H), 2.1-2.3 (m, 8H), 1.9 (m, 1H), 1.5 (m, 1H). LC/MS: 261 (M+1).

Step 8. [(6R,8aS)-6-(4-methoxy-2,3-dimethylphenyl)-hexahydro-pyrrolo[1,2-a]pyrazin-2-yl]-(6-trifluoromethyl-pyridin-3-yl)-methanone 6-Trifluoromethyl nicotinic acid (18.1 mg, 0.12 mmol), BOP (66.3 mg, 0.15 mmol), and Et$_3$N (34.8 µL, 0.25 mmol) are added to a solution of (6R,8aS)-6-(4-methoxy-2,3-dimethylphenyl)-octahydro-pyrrolo[1,2-a]pyrazine (52.2 mg, 0.2 mmol) in anhydrous DMA (0.1 mL). The reaction mixture is stirred at 50° C. for 16 h, diluted with toluene, evaporated to dryness and the residue purified by filtration through an SCX cartridge, eluting with EtOAc-MeOH-NEt$_3$ (10-1-1) to produce an oil (LC/MS: 434).

Example 4

Preparation of (6-CHLOROPYRIDIN-3-YL)((1S,4S)-5-((S)-1-(2,3-DIMETHYL-4-PROPOXYPHENYL)ETHYL)-2,5-DIAZA-BICYCLO[2.2.1]HEPTAN-2-YL)METHANONE

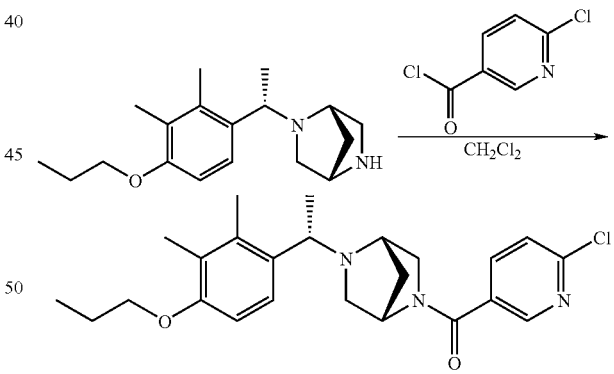

A solution of 6-chloronicotinoyl chloride (151 mg, 0.86 mmol) in 2 mL CH$_2$Cl$_2$ is added to a mixture of (1S,4S)-2-((S)-1-(2,3-dimethyl-4-propoxyphenyl)ethyl)-2,5-diaza-bicyclo[2.2.1]heptane in 5 mL of CH$_2$Cl$_2$ and aqueous NaHCO$_3$ (saturated solution, 3 mL). The mixture is stirred vigorously at room temperature for 1 h. The mixture is then diluted with 1N NaOH (5 mL) and extracted CH$_2$Cl$_2$ (2×25 mL). The combined extracts are dried over Na$_2$SO$_4$, filtered and concentrated under reduced pressure. The crude material is purified by flash chromatography on silicagel, eluting with CHCl$_3$-MeOH (40:1 to 20:1) to afford the title compound. LC/MS: 428 (M+1).

Example 5

Preparation of (6-ETHYLPYRIDIN-3-YL)-((1S, 4S)-5-{(S)-1-(2,3-DIMETHYL-4-PROPOXYPHENYL)ETHYL}-2,5-DIAZA-BICYCLO[2.2.1]HEPTAN-2-YL)-METHANONE

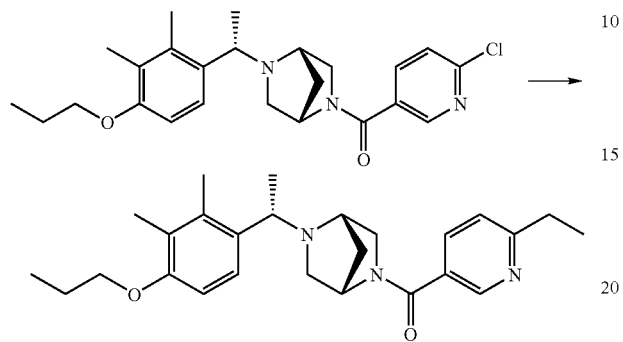

Fe(acac)$_3$ (5 mg) followed by EtMgBr (0.73 mL, 1N in THF) is added to a solution of the amide obtained in Example 4 (129 mg) in 3 mL of THF and 0.3 mL of N-methylpyrrolidinone at room temperature under N$_2$. The dark purple reaction mixture is stirred at room temperature for 50 min and then diluted with brine and extracted 3 times with EtOAc (10 mL). The combined extracts are dried over Na$_2$SO$_4$, filtered and concentrated under reduced pressure. The crude product is purified by preparative thin layer chromatography, developing 2 times with 25-1 CHCl$_3$-MeOH (25-1) to afford the desired product. LC/MS: 422 (M+1).

Example 6

Preparation of {(1S,4S)-5-[(S)-1-(2-CHLORO-4-METHOXY-3-METHYL-PHENYL)-ETHYL]-2,5-DIAZA-BICYCLO[2.2.1]HEPT-2-YL}-(1-OXY-PYRIDIN-4-YL)-METHANONE

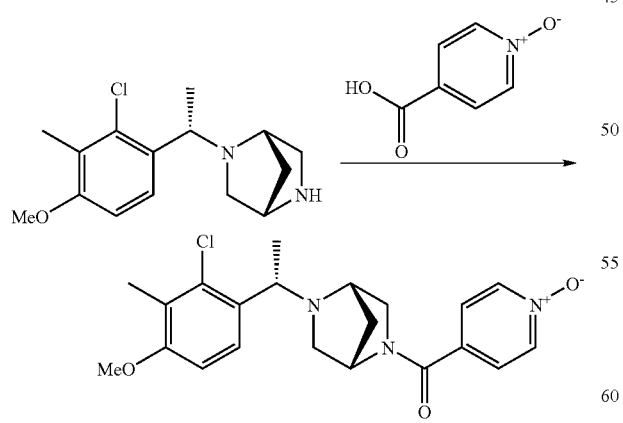

Isonicotinic acid N-oxide (8.3 mg, 0.06 mmol), BOP (33.2 mg, 0.075 mmol), and Et$_3$N (17.4 µL, 0.125 mmol) are added to a solution of (1S,4S)-2-[(S)-1-(2-chloro-4-methoxy-3-methylphenyl)-ethyl]-2,5-diazabicyclo[2.2.1]heptane (14 mg, 0.05 mmol) in anhydrous DMA (1 mL). The reaction mixture is stirred at room temperature for 16 h, diluted with EtOAc, washed with aqueous NaOH 1N (2×8 mL) and brine, dried with Na$_2$SO$_4$, filtered and concentrated under reduced pressure. The residue is purified by preparative thin layer chromatography eluting with CH$_2$Cl$_2$-MeOH—NH$_4$OH (90-9-1) to afford the title compound as a yellow oil. LC/MS: 402 (M+1).

Example 7

Preparation of {(1S,4S)-5-[(S)-1-(4-METHOXY-2, 3-DIMETHYL-PHENYL)-ETHYL]-2,5-DIAZA-BICYCLO[2.2.1]HEPT-2-YL}-PYRIMIDIN-5-YL-METHANONE

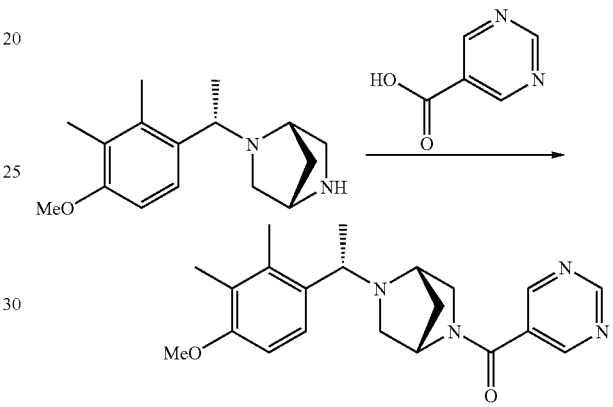

Pyrimidine-5-carboxylic acid (14.9 mg, 0.12 mmol), BOP (66.3 mg, 0.15 mmol), and Et$_3$N (34.8 µL, 0.25 mmol) are added to a solution of (1S,4S)-2-[(S)-1-(4-methoxy-2,3-dimethylphenyl)-ethyl]-2,5-diazabicyclo[2.2.1]heptane (26 mg, 0.1 mmol) in anhydrous DMA (1 mL). The reaction mixture is stirred at room temperature for 16 h, diluted with EtOAc, washed with aqueous NaOH 1N (2×8 mL) and brine, dried with Na$_2$SO$_4$, filtered, and concentrated under reduced pressure. The residue is purified by preparative thin layer chromatography eluting with CH$_2$Cl$_2$-MeOH—NH$_4$OH (90-9-1) to afford a yellow oil. LC/MS: 367 (M+1).

Example 8

Additional 1-BENZYL-4-SUBSTITUTED PIPERAZINE ANALOGUES

Additional representative substituted 1-benzyl-4-substituted piperazine analogues are shown in the following tables, and are prepared according to the methods presented in Schemes A-H and further illustrated in Examples 1-7. The compounds in TABLE I have a K$_i$ of less than 1 micromolar in the MCH1 receptor binding assay of Example 9. The compounds of TABLE II and TABLE III exhibit an EC$_{50}$ of less than 1 micromolar in the calcium mobilization assay of Example 10. The compounds in TABLE IV have a K$_i$ of less than 1 micromolar in the MCH1 agonist-stimulated GTP gamma$^{35}$S binding assay of Example 14.

Mass spectra (MS) reported in this Example and in Examples 1-7 are collected using electrospray MS, obtained in positive ion mode using a Waters ZMD II Mass Spectrometer. MS conditions are as follows:

Capillary voltage: 3.5 kV

Cone voltage: 30 V

Desolvation and source temperature: 250° C. and 120° C. respectively

Mass range: 100-750

Scan time: 0.5 second

Inter scan delay: 0.1 min

TABLE I

| Cpd | STRUCTURE | NAME | MS |
|-----|-----------|------|-----|
| 1 | 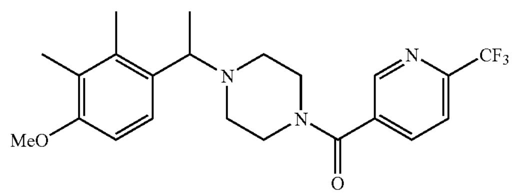 | (4-(1-(4-methoxy-2,3-dimethylphenyl)ethyl)piperazin-1-yl)(6-(trifluoromethyl)pyridin-3-yl)methanone | 422 |
| 2 | 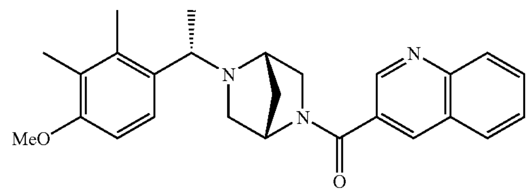 | ((1S,4S)-5-((S)-1-(4-methoxy-2,3-dimethylphenyl)ethyl)-2,5-diaza-bicyclo[2.2.1]heptan-2-yl)(quinolin-3-yl)methanone | 416 |
| 3 | 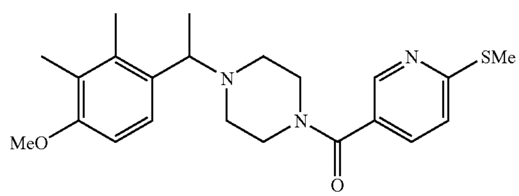 | (4-(1-(4-methoxy-2,3-dimethylphenyl)ethyl)piperazin-1-yl)(6-(methylthio)pyridin-3-yl)methanone | 400 |
| 4 | 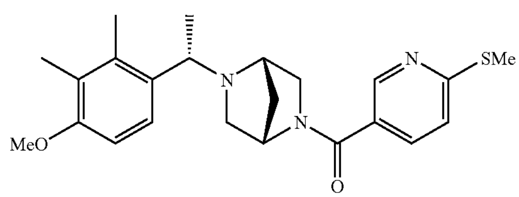 | ((1S,4S)-5-((R)-1-(4-methoxy-2,3-dimethylphenyl)ethyl)-2,5-diaza-bicyclo[2.2.1]heptan-2-yl)(6-(methylthio)pyridin-3-yl)methanone | 412 |
| 5 | 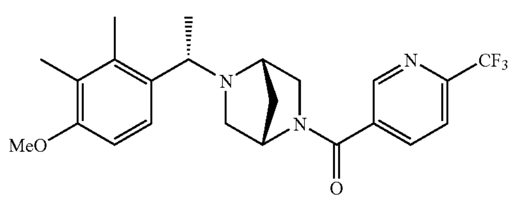 | ((1S,4S)-5-((S)-1-(4-methoxy-2,3-dimethylphenyl)ethyl)-2,5-diaza-bicyclo[2.2.1]heptan-2-yl)(6-(trifluoromethyl)pyridin-3-yl)methanone | 434 |
| 6 | 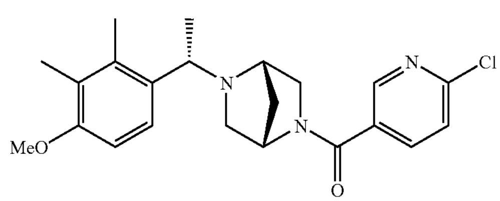 | ((1S,4S)-5-((S)-1-(4-methoxy-2,3-dimethylphenyl)ethyl)-2,5-diaza-bicyclo[2.2.1]heptan-2-yl)(6-chloro-pyridin-3-yl)methanone | 400 |
| 7 | 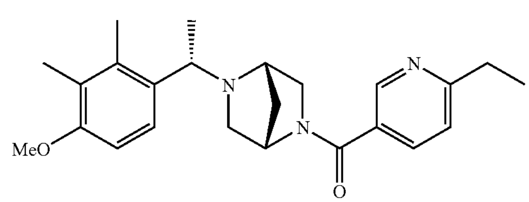 | ((1S,4S)-5-((S)-1-(4-methoxy-2,3-dimethylphenyl)ethyl)-2,5-diaza-bicyclo[2.2.1]heptan-2-yl)(6-ethyl-pyridin-3-yl)methanone | 394 |

TABLE I-continued

| Cpd | STRUCTURE | NAME | MS |
|---|---|---|---|
| 8 | 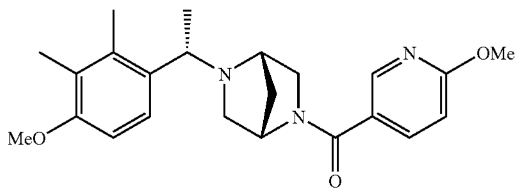 | ((1S,4S)-5-((S)-1-(4-methoxy-2,3-dimethylphenyl)ethyl)-2,5-diaza-bicyclo[2.2.1]heptan-2-yl)(6-methoxy-pyridin-3-yl)methanone | 396 |
| 9 | 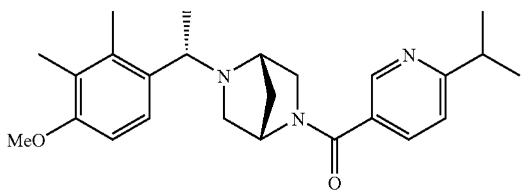 | ((1S,4S)-5-((S)-1-(4-methoxy-2,3-dimethylphenyl)ethyl)-2,5-diaza-bicyclo[2.2.1]heptan-2-yl)(6-isopropyl-pyridin-3-yl)methanone | 408 |
| 10 | 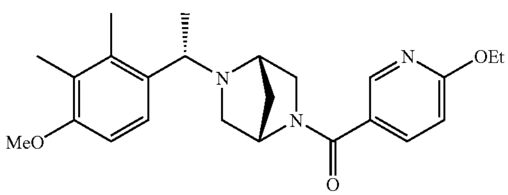 | ((1S,4S)-5-((S)-1-(4-methoxy-2,3-dimethylphenyl)ethyl)-2,5-diaza-bicyclo[2.2.1]heptan-2-yl)(6-ethoxy-pyridin-3-yl)methanone | 410 |
| 11 | 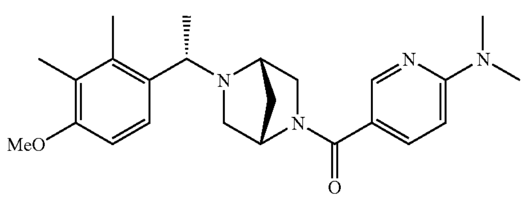 | (6-Dimethylamino-pyridin-3-yl)-{(1S,4S)-5-[(S)-1-(4-methoxy-2,3-dimethyl-phenyl)-ethyl]-2,5-diaza-bicyclo[2.2.1]hept-2-yl}-methanone | 409 |
| 12 | 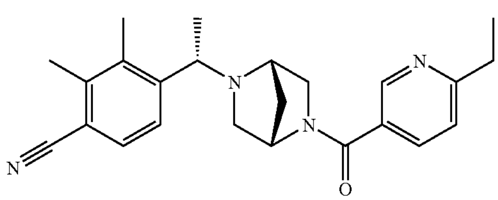 | 4-{(S)-1-[(1S,4S)-5-(6-Ethyl-pyridine-3-carbonyl)-2,5-diaza-bicyclo[2.2.1]hept-2-yl]-ethyl}-2,3-dimethyl-benzonitrile | 389 |
| 13 | 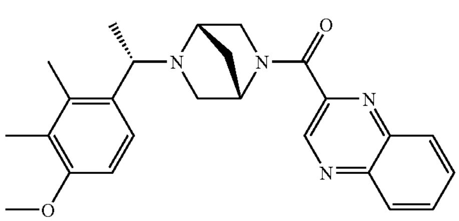 | {(1S,4S)-5-[(S)-1-(4-Methoxy-2,3-dimethyl-phenyl)-ethyl]-2,5-diaza-bicyclo[2.2.1]hept-2-yl}-quinoxalin-2-yl-methanone | 417 |

TABLE II

| Cpd | STRUCTURE | MS | NAME |
|---|---|---|---|
| 14 | 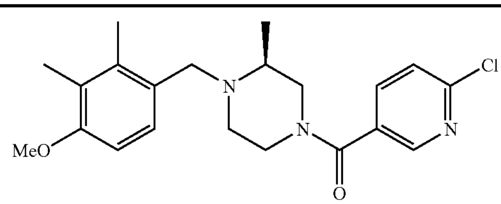 | 388 | (6-Chloro-pyridin-3-yl)-[(S)-4-(4-methoxy-2,3-dimethyl-benzyl)-3-methyl-piperazin-1-yl]-methanone |

TABLE II-continued

| Cpd | STRUCTURE | MS | NAME |
|---|---|---|---|
| 15 | 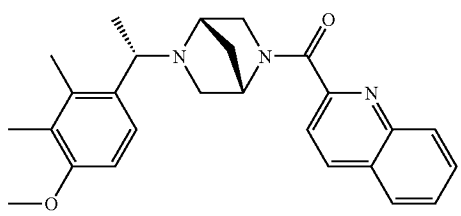 | 416 | {(1S,4S)-5-[(S)-1-(4-Methoxy-2,3-dimethyl-phenyl)-ethyl]-2,5-diaza-bicyclo[2.2.1]-hept-2-yl}-quinolin-2-yl-methanone |
| 16 | 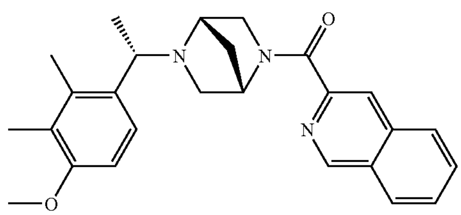 | 416 | Isoquinolin-3-yl-{(1S,4S)-5-[(S)-1-(4-methoxy-2,3-dimethylphenyl)-ethyl]-2,5-diaza-bicyclo-[2.2.1]hept-2-yl}-methanone |
| 17 | 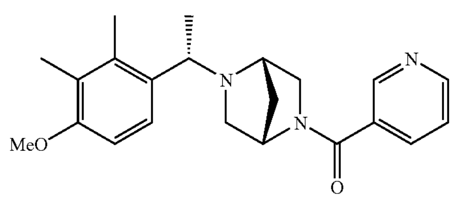 | 366 | {(1S,4S)-5-[(S)-1-(4-Methoxy-2,3-dimethyl-phenyl)-ethyl]-2,5-diaza-bicyclo[2.2.1]-hept-2-yl}-pyridin-3-yl-methanone |
| 18 | 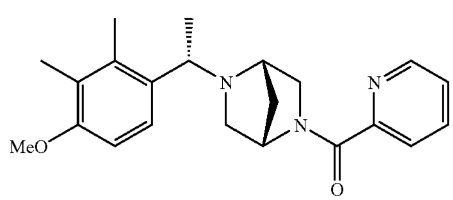 | 366 | {(1S,4S)-5-[(S)-1-(4-Methoxy-2,3-dimethyl-phenyl)-ethyl]-2,5-diaza-bicyclo-[2.2.1]hept-2-yl}-pyridin-2-yl-methanone |
| 19 | 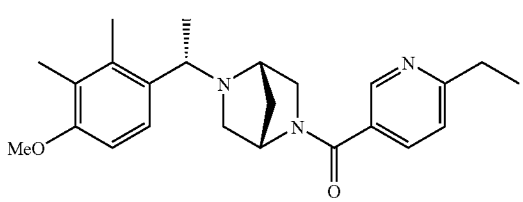 | 394 | (6-Ethyl-pyridin-3-yl)-{(1S,4S)-5-[(S)-1-(4-methoxy-2,3-dimethyl-phenyl)-ethyl]-2,5-diaza-bicyclo-[2.2.1]hept-2-yl}-methanone |
| 20 | 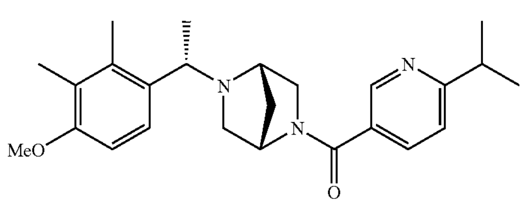 | 408 | (6-Isopropyl-pyridin-3-yl)-{(1S,4S)-5-[(S)-1-(4-methoxy-2,3-dimethylphenyl)-ethyl]-2,5-diaza-bicyclo-[2.2.1]hept-2-yl}-methanone |
| 21 | 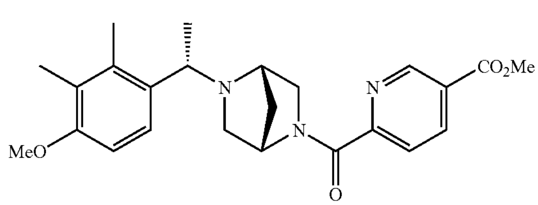 | 422 | 6-{(1S,4S)-5-[(S)-1-(4-Methoxy-2,3-dimethylphenyl)-ethyl]-2,5-diaza-bicyclo-[2.2.1]heptane-2-carbonyl}-nicotinic acid methyl ester |

TABLE II-continued

| Cpd | STRUCTURE | MS | NAME |
|---|---|---|---|
| 22 | 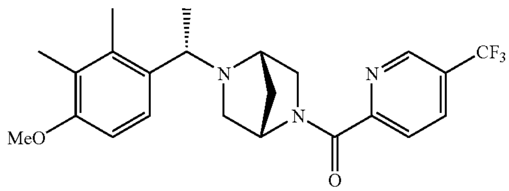 | 414 | {(1S,4S)-5-[(S)-1-(4-Methoxy-2,3-dimethyl-phenyl)-ethyl]-2,5-diaza-bicyclo-[2.2.1]hept-2-yl}-(5-trifluoromethyl-pyridin-2-yl)-methanone |
| 23 | 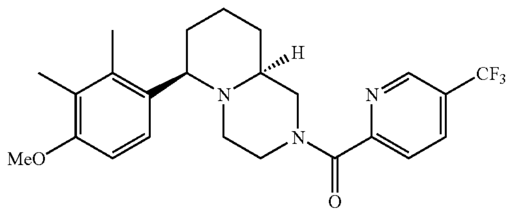 | 448 | [(6R,9aS)-6-(4-Methoxy-2,3-dimethylphenyl)-octahydro-pyrido[1,2-a]pyrazin-2-yl]-(5-trifluoromethyl-pyridin-2-yl)-methanone |
| 24 | 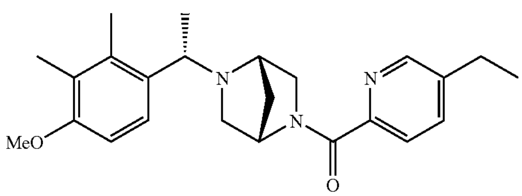 | 394 | (5-Ethyl-pyridin-2-yl)-{(1S,4S)-5-[(S)-1-(4-methoxy-2,3-dimethyl-phenyl)-ethyl]-2,5-diaza-bicyclo[2.2.1]-hept-2-yl)-methanone |
| 25 | 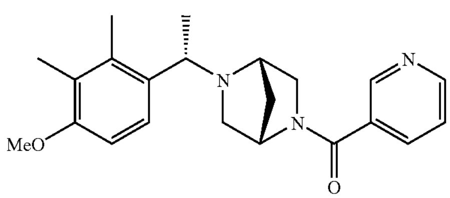 | 366 | {(1S,4S)-5-[(S)-1-(4-Methoxy-2,3-dimethyl-phenyl)-ethyl]-2,5-diaza-bicyclo[2.2.1]-hept-2-yl}-pyridin-3-yl-methanone |
| 26 | 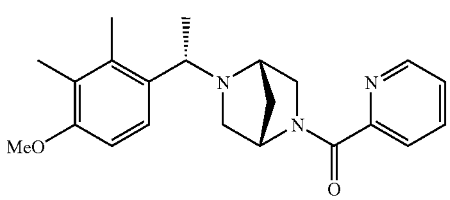 | 366 | {(1S,4S)-5-[(S)-1-(4-Methoxy-2,3-dimethyl-phenyl)-ethyl]-2,5-diaza-bicyclo-[2.2.1]-hept-2-yl}-pyridin-2-yl-methanone |
| 27 | 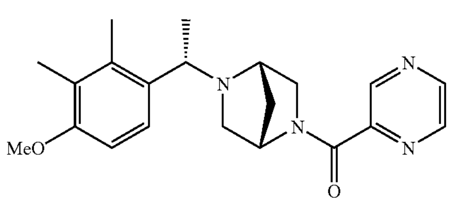 | 367 | {(1S,4S)-5-[(S)-1-(4-Methoxy-2,3-dimethyl-phenyl)-ethyl]-2,5-diaza-bicyclo-[2.2.1]hept-2-yl}-pyrazin 2-yl-methanone |
| 28 | 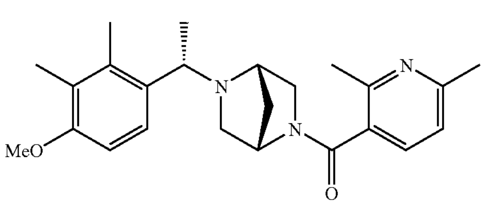 | 394 | (2,6-Dimethyl-pyridin-3-yl)-{(1S,4S)-5-[(S)-1-(4-methoxy-2,3-dimethylphenyl)-ethyl]-2,5-diazabicyclo[2.2.1]-hept-2-yl}-methanone |

TABLE II-continued

| Cpd | STRUCTURE | MS | NAME |
|---|---|---|---|
| 29 | 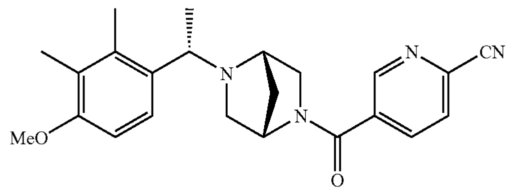 | 391 | 5-{(1S,4S)-5-[(S)-1-(4-Methoxy-2,3-dimethyl-phenyl)-ethyl]-2,5-diaza-bicyclo[2.2.1]-heptane-2-carbonyl}-pyridine-2-carbonitrile |
| 30 | 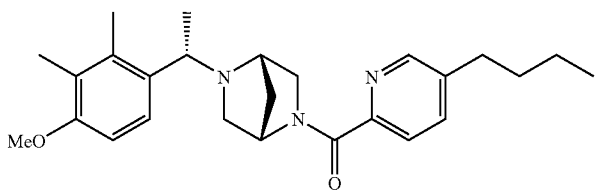 | 422 | (5-Butyl-pyridin-2-yl)-{(1S,4S)-5-[(S)-1-(4-methoxy-2,3-dimethyl-phenyl)-ethyl]-2,5-diaza-bicyclo[2.2.1]-hept-2-yl}-methanone |
| 31 | 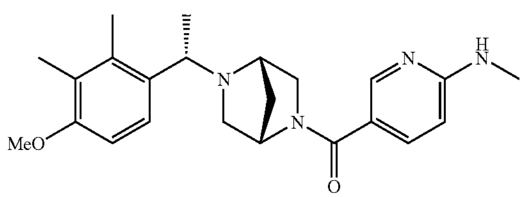 | 395 | {(1S,4S)-5-[(S)-1-(4-Methoxy-2,3-dimethyl-phenyl)-ethyl]-2,5-diaza-bicyclo[2.2.1]-hept-2-yl}-(6-methylamino-pyridin-3-yl)-methanone |
| 32 | 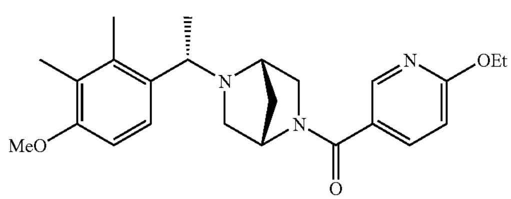 | 410 | (6-Ethoxy-pyridin-3-yl)-{(1S,4S)-5-[(S)-1-(4-methoxy-2,3-dimethylphenyl)-ethyl]-2,5-diaza-bicyclo[2.2.1]hept-2-yl}-methanone |
| 33 | 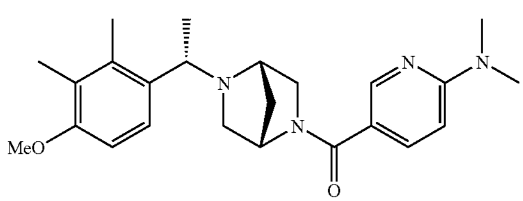 | 409 | (6-Dimethylamino-pyridin-3-yl)-{(1S,4S)-5-[(S)-1-(4-methoxy-2,3-dimethyl-phenyl)-ethyl]-2,5-diaza-bicyclo[2.2.1]hept-2-yl}-methanone |
| 34 | 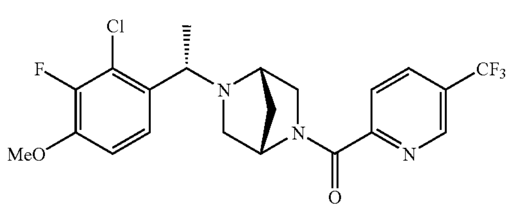 | 458 | {(1S,4S)-5-[(S)-1-(2-Chloro-3-fluoro-4-methoxy-phenyl)-ethyl]-2,5-diaza-bicyclo[2.2.1]hept-2-yl}-(5-trifluoromethyl-pyridin-2-yl)-methanone |
| 35 | 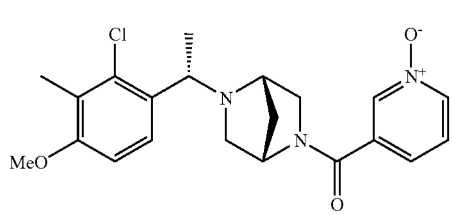 | 402 | {(1S,4S)-5-[(S)-1-(2-Chloro-4-methoxy-3-methyl-phenyl)-ethyl]-2,5-diaza-bicyclo-[2.2.1]hept-2-yl}-(1-oxy-pyridin-3-yl)-methanone |

TABLE II-continued

| Cpd | STRUCTURE | MS | NAME |
|---|---|---|---|
| 36 | 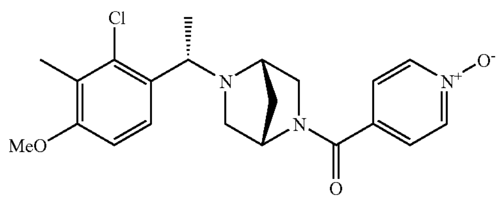 | 402 | {(1S,4S)-5-[(S)-1-(2-Chloro-4-methoxy-3-methyl-phenyl)-ethyl]-2,5-diaza-bicyclo-[2.2.1]hept-2-yl}-(1-oxy-pyridin-4-yl)-methanone |
| 37 | 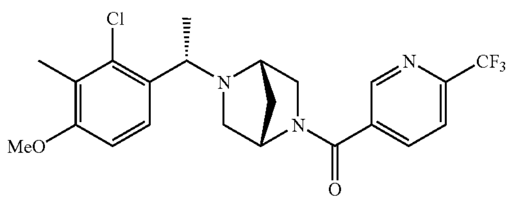 | 454 | {(1S,4S)-5-[(S)-1-(2-Chloro-4-methoxy-3-methyl-phenyl)-ethyl]-2,5-diaza-bicyclo-[2.2.1]hept-2-yl}-(6-trifluoromethyl-pyridin-3-yl)-methanone |
| 38 | 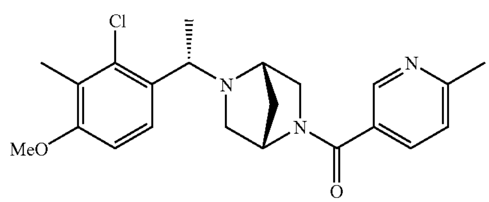 | 400 | {(1S,4S)-5-[(S)-1-(2-Chloro-4-methoxy-3-methyl-phenyl)-ethyl]-2,5-diaza-bicyclo-[2.2.1]hept-2-yl}-(6-methyl-pyridin-3-yl)-methanone |
| 39 | 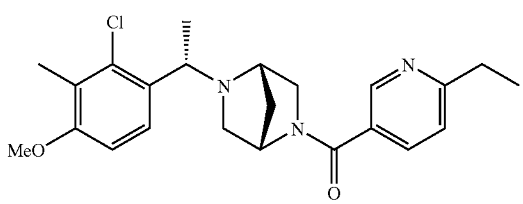 | 414 | {(1S,4S)-5-[(S)-1-(2-Chloro-4-methoxy-3-methyl-phenyl)-ethyl]-2,5-diaza-bicyclo-[2.2.1]hept-2-yl}-(6-ethyl-pyridin-3-yl)-methanone |
| 40 | 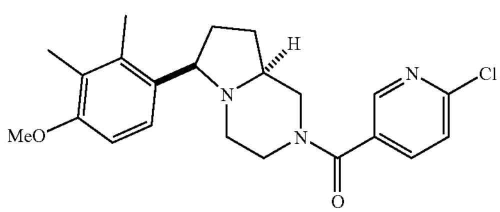 | 400 | (6-Chloro-pyridin-3-yl)-[6-(4-methoxy-2,3-dimethyl-phenyl)-hexahydro-pyrrolo[1,2-a]pyrazin-2-yl]-methanone |
| 41 | 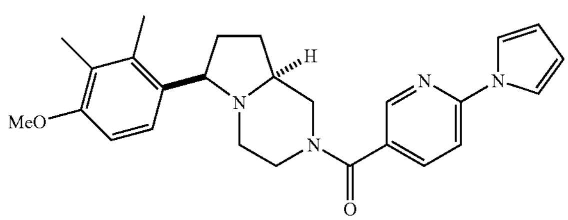 | 431 | [6-(4-Methoxy-2,3-dimethyl-phenyl)-hexahydro-pyrrolo[1,2-a]pyrazin-2-yl]-(6-pyrrol-1-yl-pyridin-3-yl)-methanone |
| 42 | 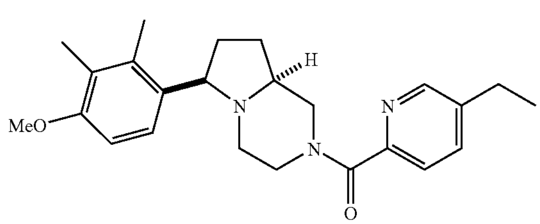 | 394 | (5-Ethyl-pyridin-2-yl)-[6-(4-methoxy-2,3-dimethyl-phenyl)-hexahydro-pyrrolo[1,2-a]pyrazin-2-yl]-methanone |

TABLE II-continued

| Cpd | STRUCTURE | MS | NAME |
|---|---|---|---|
| 43 | 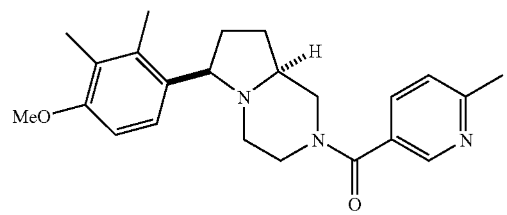 | 380 | [6-(4-Methoxy-2,3-dimethyl-phenyl)-hexahydro-pyrrolo[1,2-a]pyrazin-2-yl]-(6-methyl-pyridin-3-yl)-methanone |
| 44 | 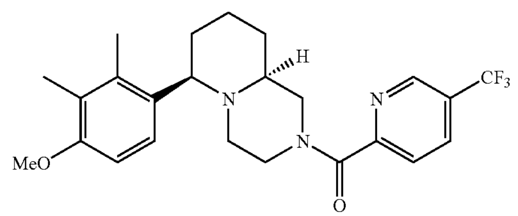 | 448 | [(6R,9aS)-6-(4-Methoxy-2,3-dimethyl-phenyl)-octahydro-pyrido[1,2-a]pyrazin-2-yl]-(5-trifluoromethyl-pyridin-2-yl)-methanone |
| 45 | 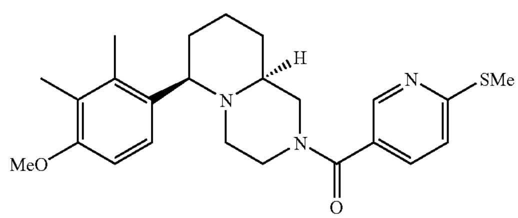 | 426 | [(6R,9aS)-6-(4-Methoxy-2,3-dimethyl-phenyl)-octahydro-pyrido[1,2-a]pyrazin-2-yl]-(6-methylsulfanyl-pyridin-3-yl)-methanone |
| 46 | 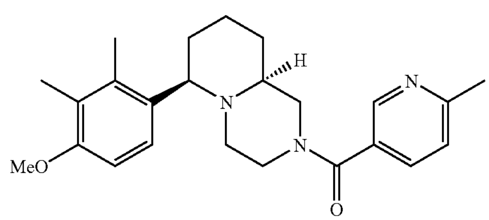 | 394 | [(6R,9aS)-6-(4-Methoxy-2,3-dimethyl-phenyl)-octahydro-pyrido[1,2-a]pyrazin-2-yl]-(6-methyl-pyridin-3-yl)-methanone |
| 47 | 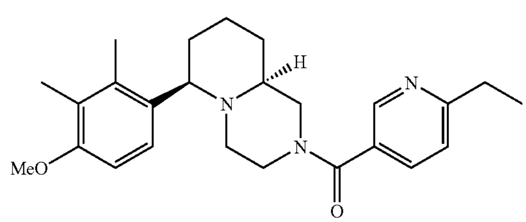 | 408 | (6-Ethyl-pyridin-3-yl)-[(6R,9aS)-6-(4-methoxy-2,3-dimethyl-phenyl)-octahydro-pyrido[1,2-a]pyrazin-2-yl]-methanone |
| 48 | 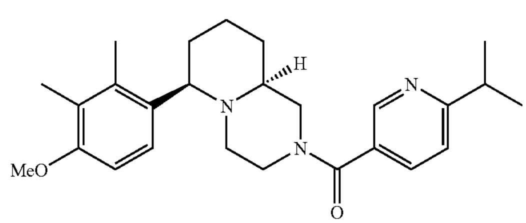 | 422 | (6-Isopropyl-pyridin-3-yl)-[(6R,9aS)-6-(4-methoxy-2,3-dimethyl-phenyl)-octahydro-pyrido[1,2-a]pyrazin-2-yl]-methanone |
| 49 | 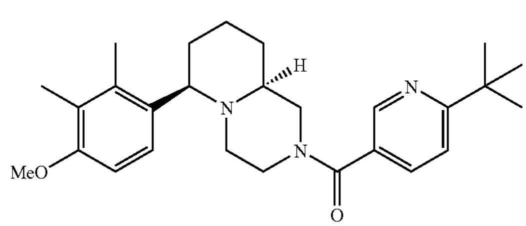 | 436 | (6-tert-Butyl-pyridin-3-yl)-[(6R,9aS)-6-(4-methoxy-2,3-dimethyl-phenyl)-octahydro-pyrido[1,2-a]pyrazin-2-yl]-methanone |

TABLE II-continued

| Cpd | STRUCTURE | MS | NAME |
|---|---|---|---|
| 50 | 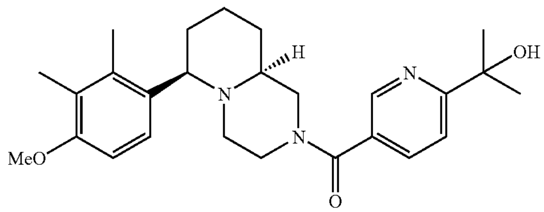 | 438 | [6-(1-Hydroxy-1-methyl-ethyl)-pyridin-3-yl]-[(6R,9aS)-6-(4-methoxy-2,3-dimethyl-phenyl)-octahydro-pyrido[1,2-a]pyrazin-2-yl]-methanone |
| 51 | 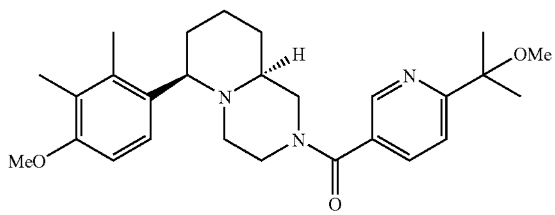 | 452 | [(6R,9aS)-6-(4-Methoxy-2,3-dimethyl-phenyl)-octahydro-pyrido[1,2-a]pyrazin-2-yl]-[6-(1-methoxy-1-methyl-ethyl)-pyridin-3-yl]-methanone |
| 52 | 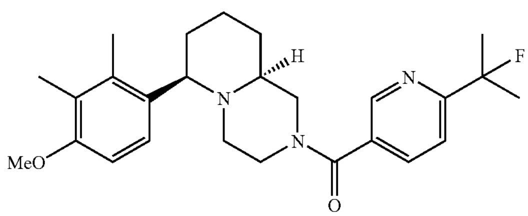 | 440 | [6-(1-Fluoro-1-methyl-ethyl)-pyridin-3-yl]-[(6R,9aS)-6-(4-methoxy-2,3-dimethyl-phenyl)-octahydro-pyrido-[1,2-a]pyrazin-2-yl]-methanone |
| 53 | 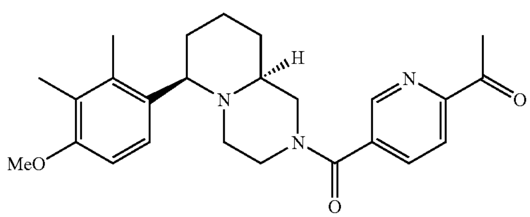 | 422 | 1-{5-[(6R,9aS)-6-(4-Methoxy-2,3-dimethyl-phenyl)-octahydro-pyrido-[1,2-a]pyrazine-2-carbonyl]-pyridin-2-yl}-ethanone |
| 54 | 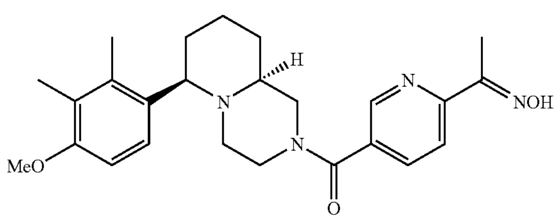 | 437 | 1-{5-[(6R,9aS)-6-(4-Methoxy-2,3-dimethyl-phenyl)-octahydro-pyrido[1,2-a]pyrazine-2-carbonyl]-pyridin-2-yl}-ethanone oxime |
| 55 | 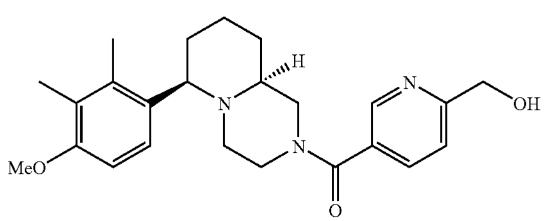 | 410 | (6-Hydroxymethyl-pyridin-3-yl)-[(6R,9aS)-6-(4-methoxy-2,3-dimethyl-phenyl)-octahydro-pyrido[1,2-a]-pyrazin-2-yl]-methanone |
| 56 | 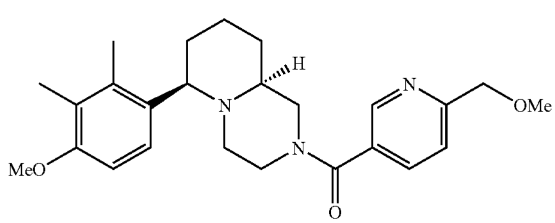 | 424 | [(6R,9aS)-6-(4-Methoxy-2,3-dimethyl-phenyl)-octahydro-pyrido[1,2-a]pyrazin-2-yl]-(6-methoxymethyl-pyridin-3-yl)-methanone |

TABLE II-continued

| Cpd | STRUCTURE | MS | NAME |
|---|---|---|---|
| 57 | 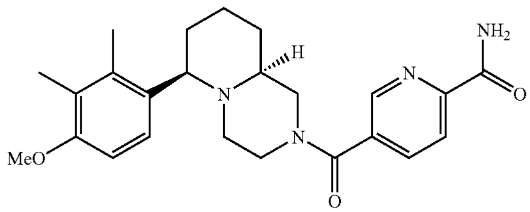 | 423 | 5-[(6R,9aS)-6-(4-Methoxy-2,3-dimethyl-phenyl)-octahydro-pyrido[1,2-a]pyrazine-2-carbonyl]-pyridine-2-carboxylic acid amide |
| 58 | 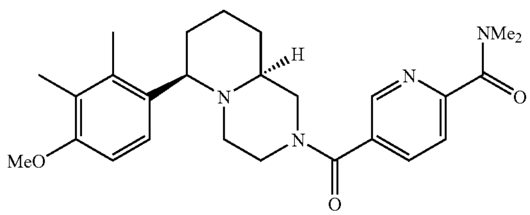 | 451 | 5-[(6R,9aS)-6-(4-Methoxy-2,3-dimethyl-phenyl)-octahydro-pyrido[1,2-a]pyrazine-2-carbonyl]-pyridine-2-carboxylic acid dimethylamide |
| 59 | 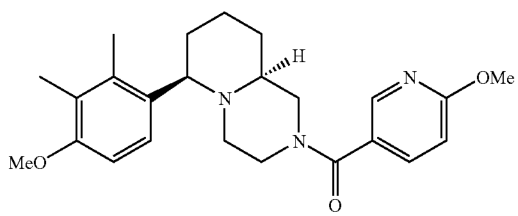 | 410 | [(6R,9aS)-6-(4-Methoxy-2,3-dimethyl-phenyl)-octahydro-pyrido[1,2-a]pyrazin-2-yl]-(6-methoxy-pyridin-3-yl)-methanone |
| 60 | 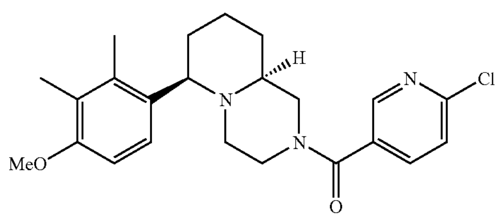 | 414 | (6-Chloro-pyridin-3-yl)-[(6R,9aS)-6-(4-methoxy-2,3-dimethyl-phenyl)-octahydro-pyrido[1,2-a]pyrazin-2-yl]-methanone |
| 61 | 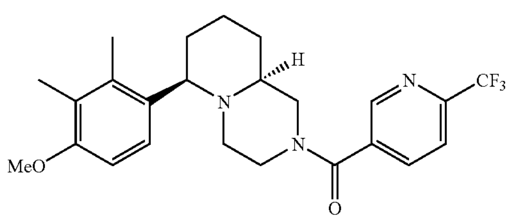 | 448 | [(6R,9As)-6-(4-Methoxy-2,3-dimethyl-phenyl)-octahydro-pyrido[1,2-a]pyrazin-2-yl]-(6-trifluoromethyl-pyridin-3-yl)-methanone |
| 62 | 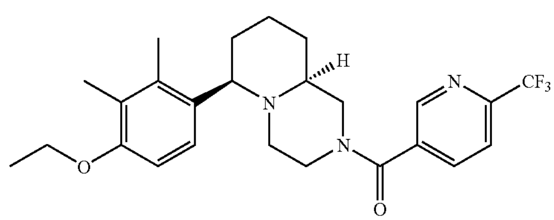 | 462 | [(6R,9aS)-6-(4-Ethoxy-2,3-dimethyl-phenyl)-octahydro-pyrido[1,2-a]pyrazin-2-yl]-(6-trifluoromethyl-pyridin-3-yl)-methanone |
| 63 | 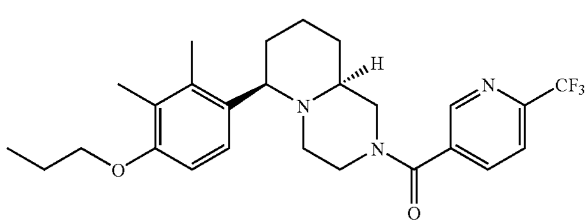 | 476 | [(6R,9aS)-6-(2,3-Dimethyl-4-propoxy-phenyl)-octahydro-pyrido[1,2-a]pyrazin-2-yl]-(6-trifluoromethyl-pyridin-3-yl)-methanone |

TABLE II-continued

| Cpd | STRUCTURE | MS | NAME |
|---|---|---|---|
| 64 | 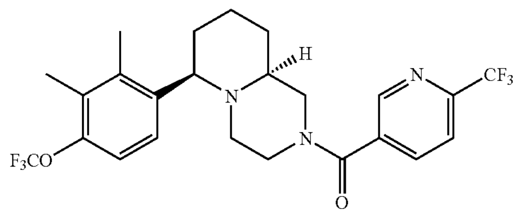 | 502 | [(6R,9aS)-6-(2,3-Dimethyl-4-trifluoromethoxy-phenyl)-octahydro-pyrido[1,2-a]-pyrazin-2-yl]-(6-trifluoro-methyl-pyridin-3-yl)-methanone |
| 65 | 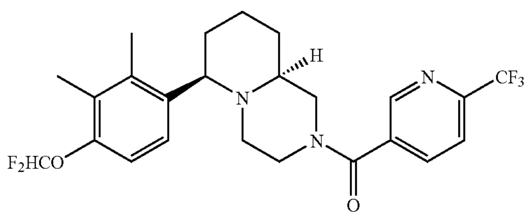 | 484 | [(6R,9aS)-6-(4-Difluoro-methoxy-2,3-dimethylphenyl)-octahydro-pyrido[1,2-a]pyrazin-2-yl]-(6-trifluoromethyl-pyridin-3-yl)-methanone |
| 66 | 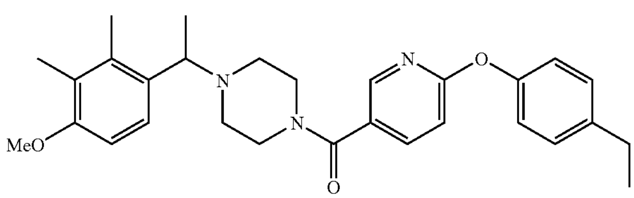 | 474 | [6-(4-Ethyl-phenoxy)-pyridin-3-yl]-{4-[1-(4-methoxy-2,3-dimethyl-phenyl)-ethyl]-piperazin-1-yl}-methanone |
| 67 | 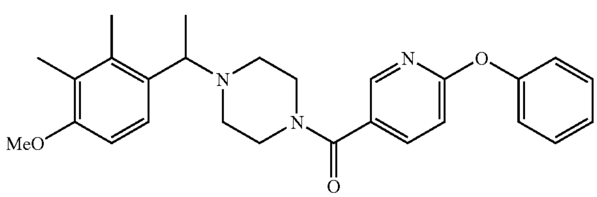 | 446 | {4-[1-(4-Methoxy-2,3-dimethylphenyl)-ethyl]-piperazin-1-yl}-(6-phenoxy-pyridin-3-yl)-methanone |
| 68 | 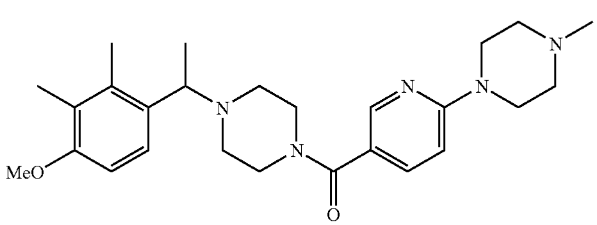 | 452 | {4-[1-(4-Methoxy-2,3-dimethyl-phenyl)-ethyl]-piperazin-1-yl}-[6-(4-methyl-piperazin-1-yl)-pyridin-3-yl]-methanone |
| 69 | 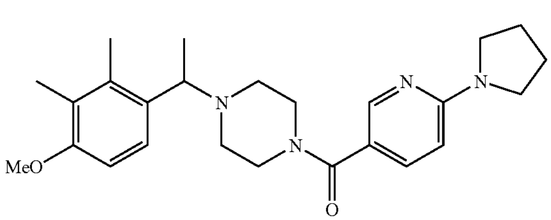 | 423 | {4-[1-(4-Methoxy-2,3-dimethyl-phenyl)-ethyl]-piperazin-1-yl}-(6-pyrrolidin-1-yl-pyridin-3-yl)-methanone |

TABLE III

| Cpd | STRUCTURE | MS | NAME |
|---|---|---|---|
| 70 | 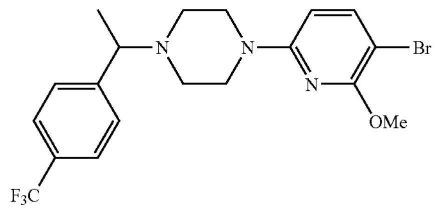 | 444 | 1-(5-Bromo-6-methoxy-pyridin-2-yl)-4-[1-(4-trifluoromethyl-phenyl)-ethyl]-piperazine |
| 71 | 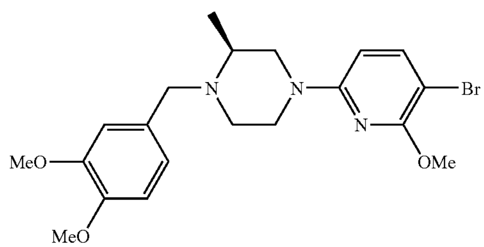 | 436 | (S)-4-(5-Bromo-6-methoxy-pyridin-2-yl)-1-(3,4-dimethoxybenzyl)-2-methyl-piperazine |
| 72 | 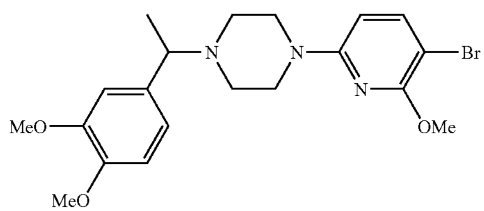 | 436 | 1-(5-Bromo-6-methoxy-pyridin-2-yl)-4-[1-(3,4-dimethoxy-phenyl)-ethyl]-piperazine |
| 73 | 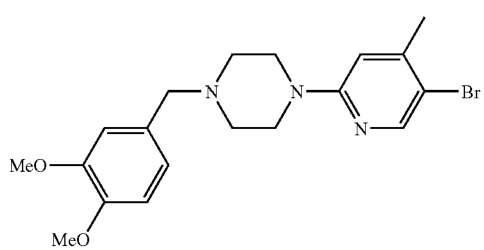 | 406 | 1-(5-Bromo-4-methyl-pyridin-2-yl)-4-(3,4-dimethoxy-benzyl)-piperazine |
| 74 | 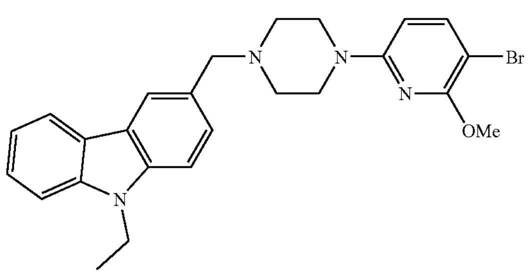 | 479 | 3-[4-(5-Bromo-6-methoxy-pyridin-2-yl)-piperazin-1-ylmethyl]-9-ethyl-9H-carbazole |
| 75 | 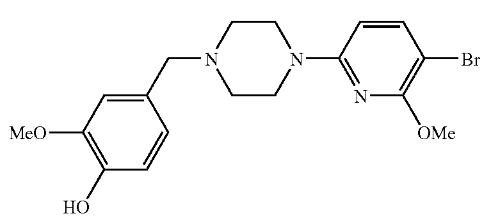 | 408 | 4-[4-(5-Bromo-6-methoxy-pyridin-2-yl)-piperazin-1-ylmethyl]-2-methoxy-phenol |

TABLE III-continued

| Cpd | STRUCTURE | MS | NAME |
|---|---|---|---|
| 76 | 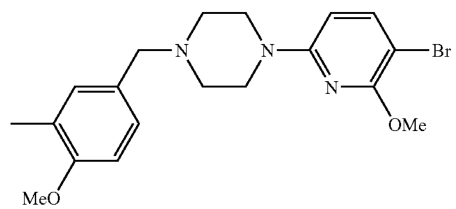 | 406 | 1-(5-Bromo-6-methoxy-pyridin-2-yl)-4-(4-methoxy-3-methyl-benzyl)-piperazine |
| 77 | 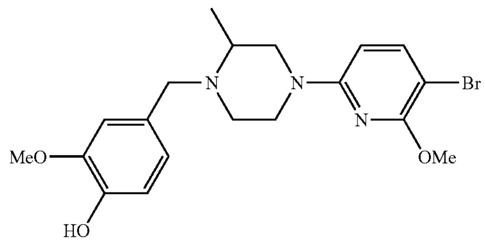 | 436 | 4-[4-(5-Bromo-6-methoxy-pyridin-2-yl)-2-methyl-piperazin-1-ylmethyl]-2-methoxy-phenol |
| 78 | 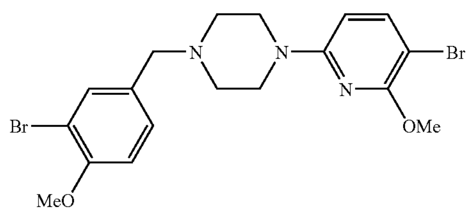 | 470 | 1-(3-Bromo-4-methoxy-benzyl)-4-(5-bromo-6-methoxy-pyridin-2-yl)-piperazine |
| 79 | 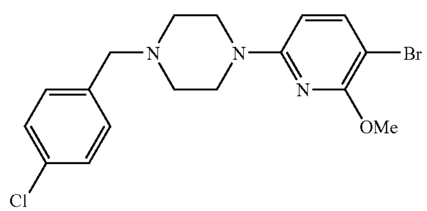 | 396 | 1-(5-Bromo-6-methoxy-pyridin-2-yl)-4-(4-chloro-benzyl)-piperazine |
| 80 | 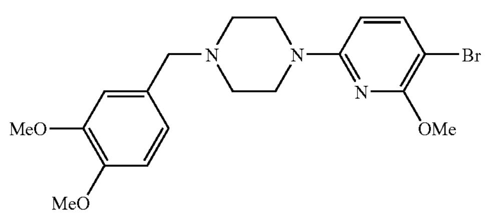 | 422 | 1-(5-Bromo-6-methoxy-pyridin-2-yl)-4-(3,4-dimethoxy-benzyl)-piperazine |
| 81 | 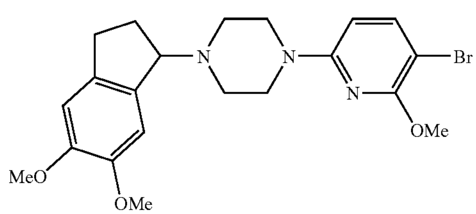 | 448 | 1-(5-Bromo-6-methoxy-pyridin-2-yl)-4-(5,6-dimethoxy-indan-1-yl)-piperazine |
| 82 | 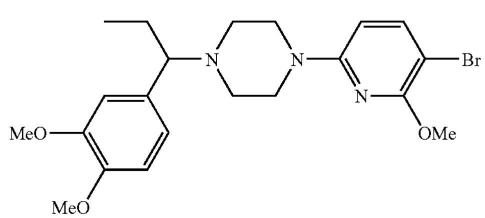 | 450 | 1-(5-Bromo-6-methoxy-pyridin-2-yl)-4-[1-(3,4-dimethoxy-phenyl)-propyl]-piperazine |

TABLE III-continued

| Cpd | STRUCTURE | MS | NAME |
|---|---|---|---|
| 83 | 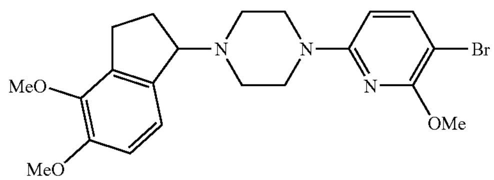 | 448 | 1-(5-Bromo-6-methoxy-pyridin-2-yl)-4-(4,5-dimethoxy-indan-1-yl)-piperazine |
| 84 | 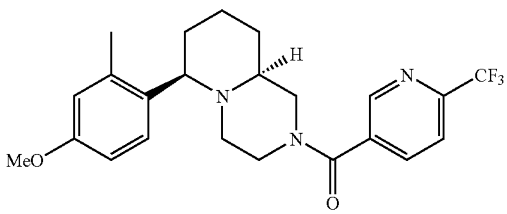 | 434 | (6R,9aS)-[6-(4-Methoxy-2-methyl-phenyl)-octahydro-pyrido[1,2-a]pyrazin-2-yl]-(6-trifluoromethyl-pyridin-3-yl)-methanone |

TABLE IV

| Cpd | STRUCTURE | MS | NAME |
|---|---|---|---|
| 85 | 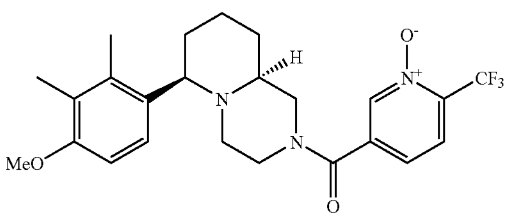 | 464 | [(6R,9aS)-6-(4-Methoxy-2,3-dimethyl-phenyl)-octahydro-pyrido[1,2-a]pyrazin-2-yl]-(1-oxy-6-trifluoromethyl-pyridin-3-yl)-methanone |
| 86 | 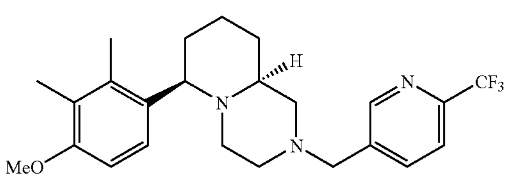 | 434 | (6R,9aS)-6-(4-Methoxy-2,3-dimethyl-phenyl)-2-(6-trifluoromethyl-pyridin-3-ylmethyl)-octahydro-pyrido[1,2-a]pyrazine |
| 87 | 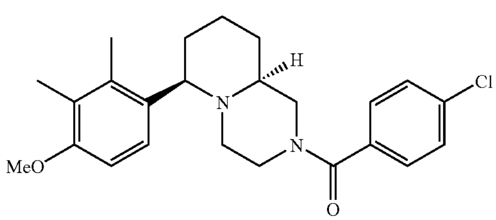 | 413 | (6R,9aS)-(4-Chloro-phenyl)-[6-(4-methoxy-2,3-dimethyl-phenyl)-octahydro-pyrido[1,2-a]pyrazin-2-yl]-methanone |
| 88 | 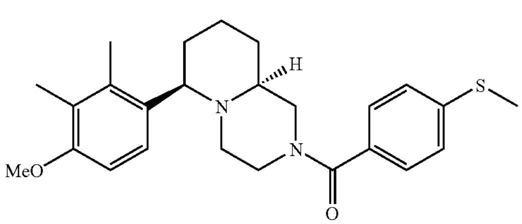 | 425 | [(6R,9aS)-6-(4-Methoxy-2,3-dimethyl-phenyl)-octahydro-pyrido[1,2-a]pyrazin-2-yl]-(4-methylsulfanyl-phenyl)-methanone |
| 89 | 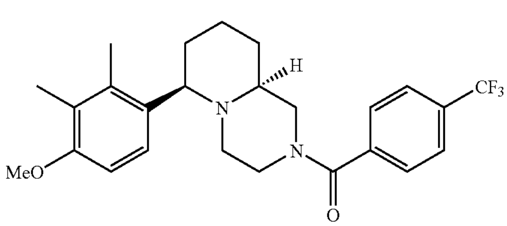 | 447 | (6R,9aS)-[6-(4-Methoxy-2,3-dimethyl-phenyl)-octahydro-pyrido[1,2-a]pyrazin-2-yl]-(4-trifluoromethyl-phenyl)-methanone |

TABLE IV-continued

| Cpd | STRUCTURE | MS | NAME |
|---|---|---|---|
| 90 | 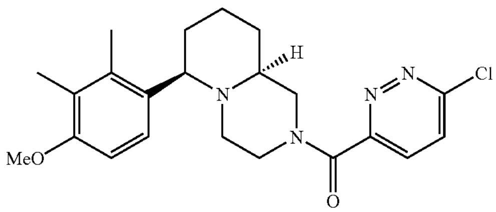 | 415 | (6R,9aS)-(6-Chloro-pyridazin-3-yl)-[6-(4-methoxy-2,3-dimethyl-phenyl)-octahydro-pyrido[1,2-a]pyrazin-2-yl]-methanone |
| 91 | 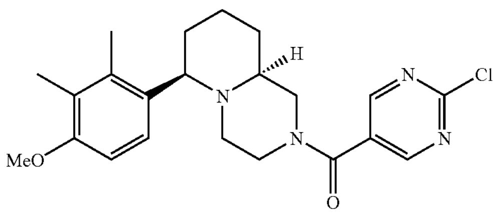 | 415 | (6R,9aS)-(2-Chloro-pyrimidin-5-yl)-[6-(4-methoxy-2,3-dimethyl-phenyl)-octahydro-pyrido[1,2-a]pyrazin-2-yl]-methanone |
| 92 | 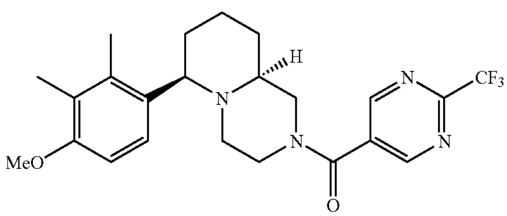 | 449 | [(6R,9aS)-6-(4-Methoxy-2,3-dimethyl-phenyl)-octahydro-pyrido[1,2-a]pyrazin-2-yl]-(2-trifluoromethyl-pyrimidin-5-yl)-methanone |
| 93 | 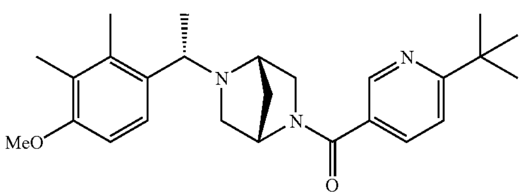 | 422 | (1S,4S)-(6-tert-Butyl-pyridin-3-yl)-{5-[1-(4-methoxy-2,3-dimethyl-phenyl)-ethyl]-2,5-diaza-bicyclo[2.2.1]hept-2-yl}-methanone |
| 94 | 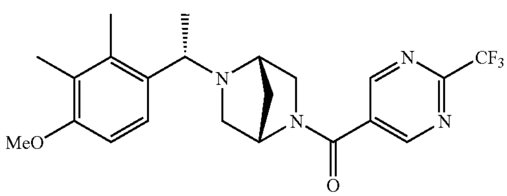 | 435 | {(1S,4S)-5-[1-(4-Methoxy-2,3-dimethyl-phenyl)-ethyl]-2,5-diaza-bicyclo[2.2.1]hept-2-yl}-(2-trifluoromethyl-pyrimidin-5-yl)-methanone |
| 95 | 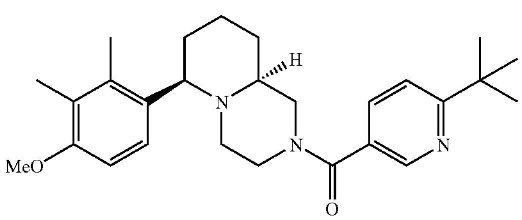 | 436 | (6R,9aS)-(6-tert-Butyl-pyridin-3-yl)-[6-(4-methoxy-2,3-dimethyl-phenyl)-octahydro-pyrido[1,2-a]pyrazin-2-yl]-methanone |
| 96 | 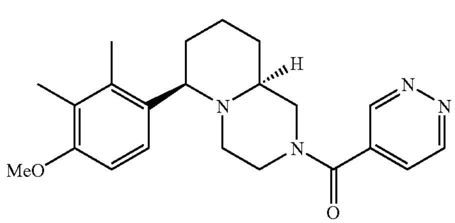 | 381 | (6R,9aS)-6-(4-Methoxy-2,3-dimethyl-phenyl)-octahydro-pyrido[1,2-a]pyrazin-2-yl]-pyridazin-4-yl-methanone |

TABLE IV-continued

| Cpd | STRUCTURE | MS | NAME |
|---|---|---|---|
| 97 | 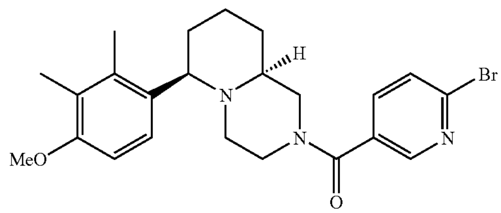 | 459 | (6R,9aS)-(6-Bromo-pyridin-3-yl)-[6-(4-methoxy-2,3-dimethyl-phenyl)-octahydro-pyrido[1,2-a]pyrazin-2-yl]-methanone |
| 98 | 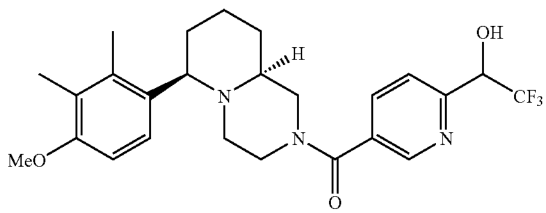 | 478 | [(6R,9aS)-6-(4-Methoxy-2,3-dimethyl-phenyl)-octahydro-pyrido[1,2-a]pyrazin-2-yl]-[6-(2,2,2-trifluoro-1-hydroxy-ethyl)-pyridin-3-yl]-methanone |
| 99 | 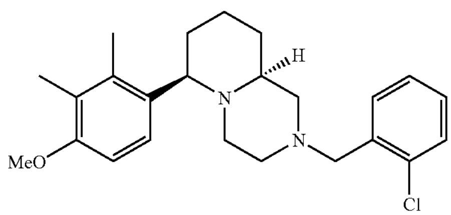 | 399 | (6R,9aS)-2-(2-Chloro-benzyl)-6-(4-methoxy-2,3-dimethyl-phenyl)-octahydro-pyrido[1,2-a]pyrazine |
| 100 | 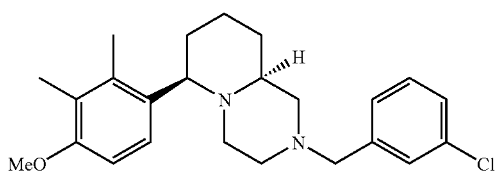 | 399 | (6R,9aS)-2-(3-Chloro-benzyl)-6-(4-methoxy-2,3-dimethyl-phenyl)-octahydro-pyrido[1,2-a]pyrazine |
| 101 | 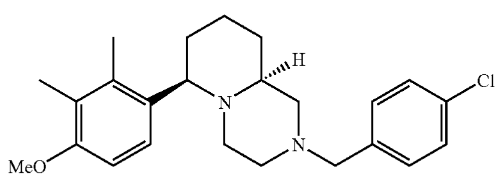 | 399 | (6R,9aS)-2-(4-Chloro-benzyl)-6-(4-methoxy-2,3-dimethyl-phenyl)-octahydro-pyrido[1,2-a]pyrazine |
| 102 | 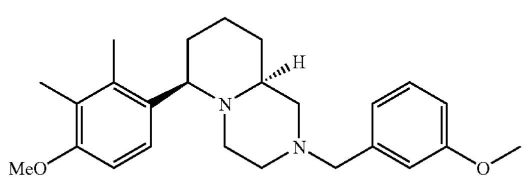 | 395 | (6R,9aS)-2-(3-Methoxy-benzyl)-6-(4-methoxy-2,3-dimethyl-phenyl)-octahydro-pyrido[1,2-a]pyrazine |
| 103 | 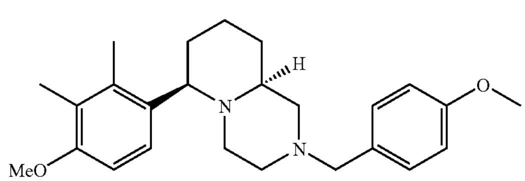 | 395 | (6R,9aS)-2-(4-Methoxy-benzyl)-6-(4-methoxy-2,3-dimethyl-phenyl)-octahydro-pyrido[1,2-a]pyrazine |
| 104 | 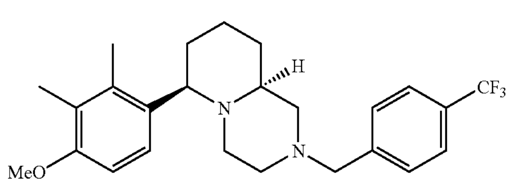 | 433 | (6R,9aS)-6-(4-Methoxy-2,3-dimethyl-phenyl)-2-(4-trifluoromethyl-benzyl)-octahydro-pyrido[1,2-a]pyrazine |

TABLE IV-continued

| Cpd | STRUCTURE | MS | NAME |
|---|---|---|---|
| 105 | 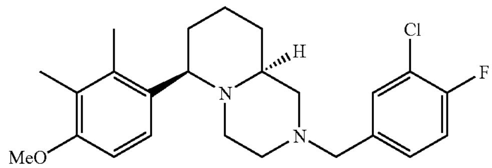 | 417 | (6R,9aS)-2-(3-Chloro-4-fluoro-benzyl)-6-(4-methoxy-2,3-dimethyl-phenyl)-octahydro-pyrido[1,2-a]pyrazine |
| 106 | 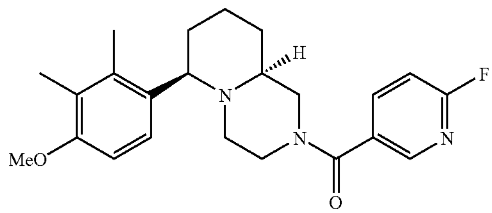 | 398 | (6R,9aS)-(6-Fluoro-pyridin-3-yl)-[6-(4-methoxy-2,3-dimethyl-phenyl)-octahydro-pyrido[1,2-a]pyrazin-2-yl]-methanone |

TABLE V

| Cpd | STRUCTURE | MS | NAME |
|---|---|---|---|
| 107 | 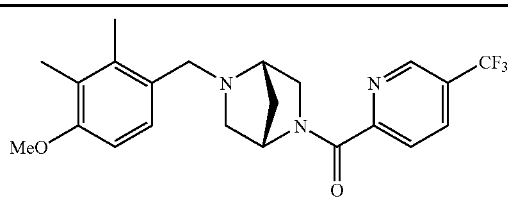 | 420 | (1S,4S)-2-(4-methoxy-2,3-dimethylbenzyl)-5-{[5-(trifluoromethyl)pyridin-2-yl]carbonyl}-2,5-diazabicyclo[2.2.1]heptane |
| 108 | 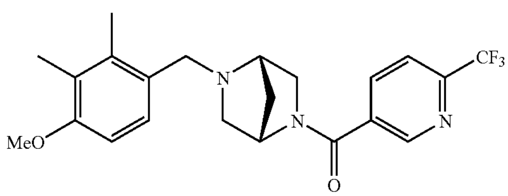 | 420 | (1S,4S)-2-(4-methoxy-2,3-dimethylbenzyl)-5-{[6-(trifluoromethyl)pyridin-3-yl]carbonyl}-2,5-diazabicyclo[2.2.1]heptane |
| 109 | 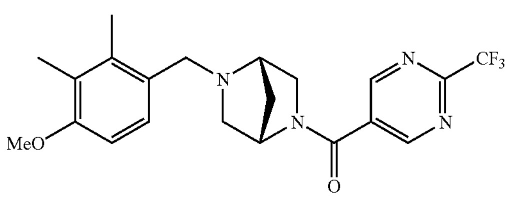 | 421 | (1S,4S)-2-(4-methoxy-2,3-dimethylbenzyl)-5-{[2-(trifluoromethyl)pyrimidin-5-yl]carbonyl}-2,5-diazabicyclo[2.2.1]heptane |

Example 9

Melanin Concentrating Hormone Receptor Binding Assay

This Example illustrates a standard assay of melanin concentrating hormone receptor binding that may be used to determine the binding affinity of compounds for the MCH receptor.

Cynomolgus macaque hypothalamus MCH1 cDNA is prepared and cloned into PCDNA3.1 (INVITROGEN Corp., Carlsbad, Calif.), and HEK293 cells (American Type Culture Collection, Manassas, Va.) are stably transfected with the MCH1 expression vector as described in PCT International Application publication number WO 03/059289, which published on Jul. 24, 2003. The disclosure of WO 03/059289 at page 52 directed to the preparation and storage of the transfected HEK293 cells is hereby incorporated by reference.

At the time of assay, pellets are thawed by addition of wash buffer (25 mM HEPES with 1.0 mM $CaCl_2$, 5.0 mM $MgCl_2$, 120 mM NaCl, pH 7.4) and homogenized for 30 seconds using a BRINKMAN POLYTRON, setting 5. Cells are centrifuged for 10 min at 48,000×g. The supernatant is discarded and the pellet is resuspended in fresh wash buffer, and homogenized again. An aliquot of this membrane homogenate is used to determine protein concentration via the Bradford method (BIO-RAD Protein Assay Kit, #500-0001, BIO-RAD, Hercules, Calif.). By this measure, a 1-liter culture of cells typically yields 50-75 mg of total membrane protein. The homogenate is centrifuged as before and resuspended to a protein concentration of 333 µg/mL in binding buffer (Wash buffer+0.1% BSA and 1.0 µM final phosphoramidon) for an assay volume of 50 μg membrane protein/150 μl binding buffer. Phosphoramidon was from SIGMA BIO-CHEMICALS, St. Louis, Mo. (cat# R-7385).

Competition binding assays are performed at room temperature in Falcon 96 well round bottom polypropylene plates. Each assay well contains 150 μL of MCH receptor-containing membranes prepared as described above, 50 μL $^{125}$I-Tyr MCH, 50 μL binding buffer, and 2 μL test compound in DMSO. $^{125}$I-Tyr MCH (specific activity=2200 Ci/mmol) is purchased from NEN, Boston, Mass. (Cat # NEX 373) and is diluted in binding buffer to provide a final assay concentration of 30 pM.

Non-specific binding is defined as the binding measured in the presence of 1 μM unlabeled MCH. MCH is purchased from BACHEM U.S.A., King of Prussia, Pa. (cat # H-1482). Assay wells used to determine MCH binding contain 150 μL of MCH receptor containing membranes, 50 μL $^{125}$I-Tyr MCH, 25 μL binding buffer and 25 μL binding buffer.

Assay plates are incubated for 1 h at room temperature. Membranes are harvested onto WALLAC™ glass fiber filters (PERKIN-ELMER, Gaithersburg, Md.) which were pre-soaked with 1.0% PEI (polyethyleneimine) for 2 h prior to use. Filters are allowed to dry overnight, and then counted in a WALLAC 1205 BETA PLATE counter after addition of WALLAC BETA SCINT™ scintillation fluid.

For saturation binding, the concentration of $^{125}$I-Tyr MCH is varied from 7 to 1,000 pM. Typically, 11 concentration points are collected per saturation binding curve. Equilibrium binding parameters are determined by fitting the allosteric Hill equation to the measured values with the aid of the computer program FitP™ (BIOSOFT, Ferguson, Mo.). For preferred compounds, $K_i$ values are below 1 micromolar, preferably below 500 nanomolar, more preferably below 100 nanomolar.

Example 10

Calcium Mobilization Assay

This Example illustrates a representative functional assay for monitoring the response of cells expressing melanin concentrating hormone receptors to melanin concentrating hormone. This assay can also be used to determine if test compounds act as agonists or antagonists of melanin concentrating hormone receptors.

Chinese Hamster Ovary (CHO) cells (American Type Culture Collection; Manassas, Va.) are stably transfected with the MCH expression vector via calcium phosphate precipitation, and are grown to a density of 15,000 cells/well in FALCON™ black-walled, clear-bottomed 96-well plates (#3904, BECTON-DICKINSON, Franklin Lakes, N.J.) in Ham's F12 culture medium (MEDIATECH, Herndon, Va.) supplemented with 10% fetal bovine serum, 25 mM HEPES and 500 μg/mL (active) G418. Prior to running the assay, the culture medium is emptied from the 96 well plates. Fluo-3 calcium sensitive dye (Molecular Probes, Eugene, Oreg.) is added to each well (dye solution: 1 mg FLUO-3 AM, 440 μL DMSO and 440 μL 20% pluronic acid in DMSO, diluted 1:4, 50 μL diluted solution per well). Plates are covered with aluminum foil and incubated at 37° C. for 1-2 h. After the incubation, the dye is emptied from the plates, cells are washed once in 100 μL KRH buffer (0.05 mM KCl, 0.115 M NaCl, 9.6 mM NaH$_2$PO$_4$, 0.01 mM MgSO$_4$, 25 mM HEPES, pH 7.4) to remove excess dye; after washing, 80 μL KRH buffer is added to each well.

Fluorescence response is monitored upon the addition of either human MCH receptor or test compound by a FLIPR™ plate reader (Molecular Devices, Sunnyvale, Calif.) by excitation at 480 nm and emission at 530 nm.

In order to measure the ability of a test compound to antagonize the response of cells expressing MCH receptors to MCH, the EC$_{50}$ of MCH is first determined. An additional 20 μL of KRH buffer and 1 μL DMSO is added to each well of cells, prepared as described above. 100 μL human MCH in KRH buffer is automatically transferred by the FLIPR instrument to each well. An 8-point concentration response curve, with final MCH concentrations of 1 nM to 3 μM, is used to determine MCH EC$_{50}$.

Test compounds are dissolved in DMSO, diluted in 20 μL KRH buffer, and added to cells prepared as described above. The 96 well plates containing prepared cells and test compounds are incubated in the dark, at room temperature for 0.5-6 h. It is important that the incubation not continue beyond 6 h. Just prior to determining the fluorescence response, 100 μL human MCH diluted in KRH buffer to 2×EC$_{50}$ is automatically added by the FLIPR instrument to each well of the 96 well plate for a final sample volume of 200 μL and a final MCH concentration of EC$_{50}$. The final concentration of test compounds in the assay wells is between 1 nM and 5 μM. Typically, cells exposed to one EC$_{50}$ of MCH exhibit a fluorescence response of about 10,000 Relative Fluorescence Units. Cells incubated with antagonists of the MCH receptor exhibit a response that is significantly less than that of the control cells to the $p \leq 0.05$ level, as measured using a parametric test of statistical significance. Typically, antagonists of the MCH receptor decrease the fluorescence response by about 20%, preferably by about 50%, and most preferably by at least 80% as compared to matched controls. IC$_{50}$ values for MCHR antagonists are determined using SIGMAPLOT software (SPSS Inc., Chicago, Ill.) and standard techniques. The IC$_{50}$ is then used to generate $K_i$ as described by Cheng and Prusoff (1973) *Biochem Pharmacol.* 22(23):3099-108.

The ability of a compound to act as an agonist of the MCH receptor is determined by measuring the fluorescence response of cells expressing MCH receptors, using the methods described above, in the absence of MCH. Compounds that cause cells to exhibit fluorescence above background are MCH receptor agonists (background autofluorescence of the test compound may be assessed using standard methods). Compounds that induce no detectable increase in the basal activity of the MCH receptor have no detectable agonist activity and are preferred.

Example 11

Purified Rat Striatum Cell Membranes

The MCH1R receptor source is a rat striatum homogenate. The rats are naïve Sprague Dawley or Wistar rats which are not food deprived overnight, and weigh roughly 250±25 grams. The striatum is rapidly/carefully dissected away from the cortex, mid-brain and hippocampus. The striatum is weighed, and homogenized in Prep buffer (50 mM Tris, pH 7.4, 10 mM MgCl$_2$, 2 mM EGTA: 23 mL per gram of striatum, typically 150 mg of tissue plus 3.5 mL of prep buffer), homogenizing for 30 seconds using a BRINKMAN POLYTRON at setting 5. The crude striatal homogenate is washed 2 times with Prep buffer and sampled for protein analysis between washes. Once the protein concentration has been determined, the final protein pellet is suspended in binding buffer at a protein density of 275 μg/200 μL binding buffer. The protein concentration of the resulting membrane preparation (hereinafter "rat striatal membranes") is conveniently measured using a Bradford protein assay (Bio-Rad Laboratories, Hercules, Calif.).

Example 12

Radioligand Binding Assays

This Example illustrates a standard assay of Melanin Concentrating Hormone receptor binding that may be used to determine the binding affinity of compounds for the MCH receptor. $^{125}$I-labeled S36057 (New England Nuclear Corp., Boston, Mass.), a stable analogue of MCH, is used as the radioligand.

Purified rat striatal membranes, prepared by the method given in Example 11 above, are resuspended by Dounce homogenization (tight pestle) in binding buffer (50 mM Tris pH. 7.4, 1.0 mM Mg Cl$_2$, 5 mM KCl, 1 mM CaCl$_2$, 120 mM NaCl, 1 mM bacitracin, 0.02 mg/mL Aprotinin & 0.1% BSA).

The optimal rat striatal homogenate input has been determined, via a protein linearity experiment, to be 275 µg/data point/250 µL. At 30 pM [$^{125}$I]-S36057, this amount of protein binds 10-15% of the input radioligand. At a [$^{125}$I]-S36057 input of 30 pM (roughly ½ to ⅓ Kd) the specific binding signal is routinely 50%. Non specific binding is defined with 1 µM MCH. Displacement binding studies, designed to determine the IC$_{50}$/K$_i$ of exogenously added compounds, are run at 30 pM [$^{125}$I]-S36057. These displacement studies are routinely run to verify activity in the rat striatum homogenate MCH1R preparation. Upon mixing of all assay components (100 µL tissue, 100 µl assay buffer, 25 µL radiolabel, and 2.5 µL compound if required, 25 µL assay buffer or nonspecific if required), the reaction is mixed and incubated at RT for 2 h in a 96-well deepwell dish. The binding reaction is terminated by rapid filtration over a 1% PEI treated filter on a 96-well Tomtec harvester, followed by washing with 50 mM Tris, pH 7.4, 120 mM NaCl. For saturation binding analysis, rat striatal membranes (275 µg) are added to polypropylene tubes containing 25 pM-0.5 nM [$^{125}$I]S36057. Nonspecific binding is determined in the presence of 10 µM MCH (Tocris Cookson Inc., Ellisville, Mo., USA) and accounts for less than 10% of total binding. For evaluation of guanine nucleotide effects on receptor affinity, GTPγS is added to duplicate tubes at the final concentration of 50 µM.

For competition analysis, membranes (275 µg) are added to polypropylene tubes containing 0.03 nM [$^{125}$I]S36057. Non-radiolabeled displacers are added to separate assays at concentrations ranging from $10^{-10}$ M to $10^{-5}$ M to yield a final volume of 0.250 mL. Nonspecific binding is determined in the presence of 10 µM MCH and accounts for less than 30% of total binding. Following a 2 h incubation at room temperature, the reaction is terminated by rapid vacuum filtration. Samples are filtered over presoaked (0.3% non-fat dry milk for 2 h prior to use) GF/C WHATMAN filters and rinsed 2 times with 5 mL cold 50 mM Tris pH 7.4. Remaining bound radioactivity is quantified by gamma counting. K$_i$ and Hill coefficient ("nH") are determined by fitting the Hill equation to the measured values with the aid of SIGMAPLOT software.

Example 13

Purified Recombinant CHO Cell Membranes Expressing Monkey MCH1R

Cynomolgus macaque hypothalamus MCH1 cDNA is prepared and cloned into PCDNA3.1 (INVITROGEN Corp., Carlsbad, Calif.) as described in PCT International Application publication number WO 03/059289, which published on Jul. 24, 2003. The resulting MCH1 expression vector is stably transfected into Chinese hamster ovary (CHO) cells (American Type Culture Collection, Manassas, Va.) via calcium precipitation. The disclosure of WO 03/059289 at page 51-52 directed to the preparation and storage of membrane pellets prepared from CHO cells stably transfected with the MCH1 vector is hereby incorporated by reference.

CHO mMCH1R cell pellets are resuspended in homogenization buffer (10 mM HEPES, 250 mM sucrose, 0.5 µg/mL leupeptin, 2 µg/mL Aprotinin, 200 µM PMSF, and 2.5 mM EDTA, pH 7.4) and homogenized using a BRINKMAN POLYTRON homogenizer (setting 5 for 30 seconds). The homogenate is centrifuged (536×g/10 min/4° C.) to pellet the nuclei. The supernatant containing isolated membranes is decanted to a clean centrifuge tube, centrifuged (48,000× g/30 min, 4° C.) and the resulting pellet resuspended in 30 mL homogenization buffer. This centrifugation and resuspension step is repeated twice. The final pellet is resuspended in ice cold Dulbecco's PBS containing 5 mM EDTA and stored in frozen aliquots at −80° C. until needed. The protein concentration of the resulting membrane preparation (hereinafter "P2 membranes") is conveniently measured using a Bradford protein assay (Bio-Rad Laboratories, Hercules, Calif.).

Example 14

Agonist-Induced GTP Binding

Agonist-stimulated GTP gamma$^{35}$S binding ("GTP binding") activity can be used to identify agonist and antagonist compounds and to differentiate neutral antagonist compounds from those that possess inverse agonist activity. This activity can also be used to detect partial agonism mediated by antagonist compounds. A compound being analyzed in this assay is referred to herein as a "test compound."

Agonist-stimulated GTP binding on purified P2 membranes (prepared as described in Example 13) is assessed using MCH as agonist in order to ascertain the level of signal, and EC$_{50}$ value of MCH as measured by GTP binding.

P2 membranes from the CHO cells are resuspended by Dounce homogenization (tight pestle) in GTP binding assay buffer (50 mM Tris pH 7.4, 120 mM NaCl, 5 mM MgCl2, 2 mM EGTA, 0.1% BSA, 0.1 mM bacitracin, 100 KIU/mL aprotinin, 5 µM GDP, 10 µg/mL saponin) and added to reaction tubes at a concentration of 50 µg protein/reaction tube. After adding increasing doses of the agonist MCH at concentrations ranging from $10^{-12}$ M to $10^{-6}$ M, reactions are initiated by the addition of 100 pM GTP gamma$^{35}$S. In competition experiments, non-radiolabeled test compounds (e.g. compounds provided herein) are added to separate assays at concentrations ranging from $10^{-10}$ M to $10^{-5}$ M along with 10 nM MCH to yield a final volume of 0.25 mL.

Neutral antagonists are those test compounds that reduce the MCH stimulated GTP binding activity towards, but not below, baseline (the level of GTP bound by membranes in this assay in the absence of added MCH or other agonist and in the further absence of any test compound).

An antagonist test compound that elevates GTP binding activity above baseline in the absence of added MCH in this GTP binding assay is characterized as having partial agonist activity. Preferred antagonist compounds described herein do not elevate GTP binding activity under such conditions more than 10% above baseline, preferably not more than 5% above baseline, and most preferably not more than 2% above baseline.

Following a 60-min incubation at room temperature, the reactions are terminated by vacuum filtration over GF/C filters (pre-soaked in wash buffer, 0.1% BSA) followed by washing with ice-cold wash buffer (50 mM Tris pH 7.4, 120 mM NaCl). The amount of G-alpha-bound (and thereby membrane-bound) GTP gamma$^{35}$S is determined by measuring the bound radioactivity, preferably by liquid scintillation spectrometry of the washed filters. Non-specific binding is determined using 10 mM GTP gamma$^{35}$S and typically represents less than 10% of total binding. Data is expressed as percent above basal (baseline). The results of these GTP binding experiments are analyzed using SIGMA-PLOT software and $IC_{50}$ determined. The $IC_{50}$ is then used to generate $K_i$ as described by Cheng and Prusoff (1973) *Biochem Pharmacol.* 22(23):3099-108.

Preferred compounds are MCH1 receptor antagonists that do not possess significant (e.g., greater than 5%) agonist activity in any of the MCH mediated functional assays discussed herein. Specifically, this undesired agonist activity can be evaluated, for example, in the GTP binding assay described above, by measuring small molecule mediated GTP binding in the absence of the agonist, MCH. The preferred extent of MCH1R agonist activity exhibited by compounds of the invention is less than 10%, more preferably less than 5% and most preferably less than 2% of the response elicited by the agonist, MCH.

Example 15

MDCK Cytotoxicity Assay

This Example illustrates the evaluation of compound toxicity using a Madin Darby canine kidney (MDCK) cell cytotoxicity assay.

1 μL of test compound is added to each well of a clear bottom 96-well plate (PACKARD, Meriden, Conn.) to give final concentration of compound in the assay of 10 μM, 100 μM or 200 μM. Solvent without test compound is added to control wells.

MDCK cells, ATCC no. CCL-34 (American Type Culture Collection, Manassas, Va.), are maintained in sterile conditions following the instructions in the ATCC production information sheet. Confluent MDCK cells are trypsinized, harvested, and diluted to a concentration of 0.1×10$^6$ cells/mL with warm (37° C.) medium (VITACELL Minimum Essential Medium Eagle, ATCC catalog # 30-2003). 100 μL of diluted cells is added to each well, except for five standard curve control wells that contain 100 μL of warm medium without cells. The plate is then incubated at 37° C. under 95% $O_2$, 5% $CO_2$ for 2 h with constant shaking. After incubation, 50 μL of mammalian cell lysis solution (from the PACKARD (Meriden, Conn.) ATP-LITE-M Luminescent ATP detection kit) is added per well, the wells are covered with PACKARD TOPSEAL stickers, and plates are shaken at approximately 700 rpm on a suitable shaker for 2 min.

Compounds causing toxicity will decrease ATP production, relative to untreated cells. The ATP-LITE-M Luminescent ATP detection kit is generally used according to the manufacturer's instructions to measure ATP production in treated and untreated MDCK cells. PACKARD ATP LITE-M reagents are allowed to equilibrate to room temperature. Once equilibrated, the lyophilized substrate solution is reconstituted in 5.5 mL of substrate buffer solution (from kit). Lyophilized ATP standard solution is reconstituted in deionized water to give a 10 mM stock. For the five control wells, 10 μL of serially diluted PACKARD standard is added to each of the standard curve control wells to yield a final concentration in each subsequent well of 200 nM, 100 nM, 50 nM, 25 nM and 12.5 nM. PACKARD substrate solution (50 mL) is added to all wells, which are then covered, and the plates are shaken at approximately 700 rpm on a suitable shaker for 2 min. A white PACKARD sticker is attached to the bottom of each plate and samples are dark adapted by wrapping plates in foil and placing in the dark for 10 min. Luminescence is then measured at 22° C. using a luminescence counter (e.g., PACKARD TOPCOUNT Microplate Scintillation and Luminescence Counter or TECAN SPECTRAFLUOR PLUS), and ATP levels calculated from the standard curve. ATP levels in cells treated with test compound(s) are compared to the levels determined for untreated cells. Cells treated with 10 μM of a preferred test compound exhibit ATP levels that are at least 80%, preferably at least 90%, of the untreated cells. When a 100 μM concentration of the test compound is used, cells treated with preferred test compounds exhibit ATP levels that are at least 50%, preferably at least 80%, of the ATP levels detected in untreated cells.

Example 16

Microsomal In Vitro Half-Life

This Example illustrates the evaluation of compound half-life values ($t_{1/2}$ values) using a representative liver microsomal half-life assay.

Pooled human liver microsomes are obtained from Xeno-Tech LLC (Kansas City, Kans.). Such liver microsomes may also be obtained from In Vitro Technologies (Baltimore, Md.) or Tissue Transformation Technologies (Edison, N.J.). Six test reactions are prepared, each containing 25 μL microsomes, 5 μL of a 100 μM solution of test compound, and 399 μL 0.1 M phosphate buffer (19 mL 0.1 M $NaH_2PO_4$, 81 mL 0.1 M $Na_2HPO_4$, adjusted to pH 7.4 with $H_3PO_4$). A seventh reaction is prepared as a positive control containing 25 μL microsomes, 399 mL 0.1 M phosphate buffer, and 5 μL of a 100 μM solution of a compound with known metabolic properties (e.g., DIAZEPAM or CLOZAPINE). Reactions are preincubated at 39° C. for 10 min.

Cofactor mixture is prepared by diluting 16.2 mg NADP and 45.4 mg glucose-6-phosphate in 4 mL 100 mM $MgCl_2$. Glucose-6-phosphate dehydrogenase solution is prepared by diluting 214.3 μL glucose-6-phosphate dehydrogenase suspension (Roche Molecular Biochemicals; Indianapolis, Ind.) into 1285.7 μL distilled water. 71 μL of starting reaction mixture (3 mL cofactor mixture; 1.2 mL glucose-6-phosphate dehydrogenase solution) is added to 5 of the 6 test reactions and to the positive control. 71 μL 100 mM $MgCl_2$ is added to the sixth test reaction, which is used as a negative control. At each time point (0, 1, 3, 5 and 10 min), 75 μL of each reaction mix is pipetted into a well of a 96-well deep-well plate containing 75 μL ice-cold acetonitrile. Samples are vortexed and centrifuged 10 min at 3500 rpm (Sorval T 6000D centrifuge, H1000B rotor). 75 μL of supernatant from each reaction is transferred to a well of a

What is claimed is:

1. A compound of the formula

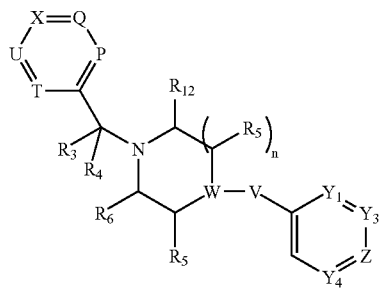

or a pharmaceutically acceptable salt thereof, wherein:
V is absent or —(C=O)—;
W is nitrogen,
$Y_1$ is CH or nitrogen;
$Y_3$ and $Y_4$ are independently $CR_1$ or nitrogen; and Z is nitrogen or $CR_2$; such that at least one of $Y_3$, $Y_4$ and Z is nitrogen, and at least one of $Y_3$, $Y_4$ and Z is substituted carbon;
each $R_1$ is independently:
  (i) hydrogen, halogen, hydroxy, nitro, cyano, amino, $C_1$-$C_6$alkyl, $C_2$-$C_6$alkenyl, $C_2$-$C_6$alkynyl, $C_1$-$C_6$alkoxy, halo$C_1$-$C_6$alkyl, halo$C_1$-$C_6$alkoxy, amino$C_1$-$C_6$alkyl, mono- or di-($C_1$-$C_6$alkyl)amino$C_0$-$C_6$alkyl, ($C_3$-$C_7$cycloalkyl)$C_0$-$C_6$alkyl or (4- to 7-membered heterocycloalkyl)$C_0$-$C_6$alkyl; or
  (ii) taken together with $R_2$ to form a fused 5- or 6-membered carbocycle or heterocycle, each of which is substituted with 0 to 3 substituents independently chosen from halogen, hydroxy, nitro, cyano, amino, $C_1$-$C_4$alkyl, $C_1$-$C_4$alkoxy, halo$C_1$-$C_4$alkyl and halo$C_1$-$C_4$alkoxy;
$R_2$ is halogen, nitro, cyano, amino, acetyl, carboxamide, $C_1$-$C_6$alkyl, $C_2$-$C_6$alkenyl, $C_2$-$C_6$alkynyl, $C_2$-$C_6$alkanoyl, $C_2$-$C_6$alkyloxime, $C_1$-$C_6$alkoxy, $C_1$-$C_6$alkoxy$C_1$-$C_4$alkyl, hydroxy$C_1$-$C_6$alkyl, $C_1$-$C_6$alkoxycarbonyl, mono- or di-alkylcarboxamide, $C_1$-$C_6$alkylthio, $C_1$-$C_6$alkylsulfonyl, halo$C_1$-$C_6$alkyl, halo$C_1$-$C_6$alkoxy, amino$C_1$-$C_6$alkyl, mono- or di-($C_1$-$C_6$alkyl)amino$C_0$-$C_6$alkyl or ($C_3$-$C_7$cycloalkyl)$C_0$-$C_6$alkyl; or
$R_2$ is (4- to 7-membered heterocycloalkyl)$C_0$-$C_6$alkyl, phenyl$C_0$-$C_2$alkyl, phenyl$C_1$-$C_2$alkoxy or (5 or 6-membered heteroaryl)$C_0$-$C_2$alkyl, each of which is substituted with 0 to 3 substituents independently chosen from halogen, $C_1$-$C_2$alkoxy and $C_1$-$C_2$alkyl; or
$R_2$ is taken together with a $R_1$ to form a fused 5- or 6-membered carbocycle or heterocycle, each of which is substituted with 0 to 3 substituents independently chosen from halogen, hydroxy, nitro, cyano, amino, $C_1$-$C_4$alkyl, $C_1$-$C_4$alkoxy, halo$C_1$-$C_4$alkyl and halo$C_1$-$C_4$alkoxy;
n is 1 or 2;
$R_3$ is: taken together with $R_6$ to form a fused heterocycle having one ring, wherein the ring contains 6 ring members and 0 additional heteroatoms;
$R_4$ is hydrogen, $C_1$-$C_6$alkyl or halo$C_1$-$C_6$alkyl;
each $R_5$ is independently:
  (i) hydrogen, halogen, hydroxy, nitro, cyano, amino, $C_1$-$C_6$alkyl, $C_2$-$C_6$alkenyl, $C_2$-$C_6$alkynyl, $C_1$-$C_6$alkoxy, halo$C_1$-$C_6$alkyl, halo$C_1$-$C_6$alkoxy, mono- or di-($C_1$-$C_6$alkyl)amino or amino$C_1$-$C_6$alkyl;
$R_6$ is: taken together with $R_3$ to form a fused heterocycle having one ring, wherein the ring contains 6 ring members and 0 additional heteroatoms;
P is N or $CR_7$;
Q is N or $CR_8$;
U is N or $CR_9$;
T is N or $CR_{10}$;
X is N or $CR_{11}$;
$R_7$ is: (i) hydrogen, halogen, hydroxy, nitro, cyano, —COOR or a group of the formula L-M; or (ii) taken together with $R_8$ to form a fused 5- or 6-membered carbocycle or heterocycle;
$R_8$ is: (i) halogen, hydroxy, nitro, cyano, —COOH or a group of the formula L-M; or (ii) taken together with $R_7$ to form a fused 5- or 6-membered carbocycle or heterocycle;
$R_9$ is: (i) hydrogen, halogen, hydroxy, nitro, cyano, —COOH or a group of the formula L-M; or (ii) taken together with $R_{10}$ or $R_{11}$ to form a fused 5- to 10-membered carbocycle or heterocycle;
$R_{10}$ is: (i) hydrogen, halogen, hydroxy, nitro, cyano, —COOH or a group of the formula L-M; (ii) taken together with $R_9$ to form a fused 5- to 10-membered carbocycle or heterocycle;
$R_{11}$ is: (i) halogen, hydroxy, nitro, cyano, —COOH or a group of the formula L-M; or (ii) taken together with $R_9$ to form a fused carbocycle or heterocycle;
$R_{12}$ is: (i) hydrogen, halogen, hydroxy, nitro, cyano, amino, $C_1$-$C_6$alkyl, $C_2$-$C_6$alkenyl, $C_2$-$C_6$alkynyl, $C_1$-$C_6$alkoxy, halo$C_1$-$C_6$alkyl, halo$C_1$-$C_6$alkoxy, mono- or di-($C_1$-$C_6$alkyl)amino or amino$C_1$-$C_6$alkyl; or
each L is independently a single covalent bond, $N(R_{13})$, O, C(=O), $SO_2$, $SO_2NH$, C(=))$N(R_{13})$ or $N(R_{13})C$(=O), wherein each $R_{13}$ is independently hydrogen, $C_1$-$C_6$alkyl, $C_2$-$C_6$alkenyl, $C_2$-$C_6$alkynyl or halo$C_1$-$C_6$alkyl; and
each M is independently hydrogen, $C_1$-$C_6$alkyl, $C_2$-$C_6$alkenyl, $C_2$-$C_6$alkynyl, halo$C_1$-$C_6$alkyl, amino$C_1$-$C_6$alkyl or a 5- to 10-membered cycloalkyl or heterocycloalkyl;
such that if $Y_1$ and $Y_3$ are both nitrogen and $R_{11}$ is trifluoromethyl, then $R_2$ is not amino.

2. A compound or salt of claim 1, wherein Q is $CR_8$ and X is $CR_{11}$.

3. A compound or salt of claim 2, wherein P is $CR_7$.

4. A compound or salt of claim 3, wherein $R_7$ is not hydrogen.

5. A compound or salt of claim 1, wherein $R_{11}$ is $C_1$-$C_4$alkoxy.

6. A compound or salt of claim 5, wherein U is $CR_9$ and T is $CR_{10}$.

7. A compound or salt of claim 1, wherein $R_7$ and $R_8$ are each chosen from $C_1$-$C_4$alkyl.

8. A compound or salt of claim 1, wherein V is C=O.

9. A compound or salt of claim 1, wherein Z is $CR_2$.

10. A compound or salt of claim 9, wherein $R_2$ is halogen, cyano, amino, $C_1$-$C_4$alkyl, $C_2$-$C_4$alkenyl, $C_2$-$C_4$alkynyl, $C_1$-$C_4$alkoxy, $C_1$-$C_4$alkylthio, halo$C_1$-$C_4$alkyl, mono- or di-($C_1C_4$alkyl)amino, ($C_3$-$C_7$cycloalkyl)$C_0$-$C_4$alkyl or (4- to 7-membered heterocycloalkyl)$C_0$-$C_4$alkyl, or $R_2$ is taken together with a $R_1$ to form a fused 5- or 6-membered carbocycle or heterocycle.

11. A compound or salt of claim 10, wherein $R_2$ is halogen, cyano, methyl, ethyl, isopropyl, methoxy, ethoxy, methylthio, ethylthio, trifluoromethyl or mono- or di-methylamino.

12. compound or salt of claim 1, wherein the compound has the formula:

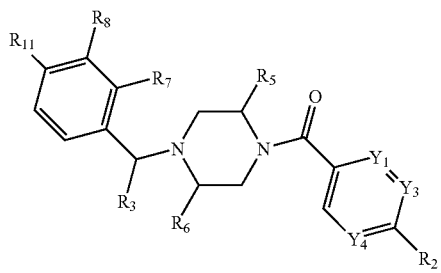

wherein:

$Y_1$ is CH, C—$CH_3$ or nitrogen;

$Y_3$ and $Y_4$ are independently $CR_1$ or nitrogen, such that at least one of $Y_3$ and $Y_4$ is nitrogen, and $Y_1$ is carbon if $Y_3$ is nitrogen;

each $R_1$ is independently:
(i) hydrogen, halogen, hydroxy, cyano, amino, $C_1$-$C_6$alkyl, $C_2$-$C_6$alkenyl, $C_2$-$C_6$alkynyl, $C_1$-$C_6$alkoxy, halo$C_1$-$C_6$alkyl, amino$C_1$-$C_6$alkyl or ($C_3$-$C_7$cycloalkyl)$C_0$-$C_2$alkyl; or
(ii) taken together with $R_2$ to form a fused 5- or 6-membered carbocycle or heterocycle;

$R_2$ is halogen, cyano, amino, $C_1$-$C_4$alkyl, $C_2$-$C_4$alkenyl, $C_2$-$C_4$alkynyl, $C_1$-$C_4$alkoxy, $C_1$-$C_4$alkylthio, halo$C_1$-$C_4$alkyl, mono- or di-($C_1$-$C_4$alkyl)amino, ($C_3$-$C_7$cycloalkyl)$C_0$-$C_4$alkyl, or (4- to 7-membered heterocycloalkyl)$C_0$-$C_4$alkyl or taken together with a $R_1$ to form a fused 5-or 6-membered carbocycle or heterocycle;

$R_3$ is: taken together with $R_6$ to form a fused 6-membered heterocycloalkyl;

$R_5$ is: (i) hydrogen, halogen, hydroxy, nitro, cyano, amino, $C_1$-$C_6$alkyl, $C_2$-$C_6$alkenyl, $C_2$-$C_6$alkynyl, $C_1$-$C_6$alkoxy, halo$C_1$-$C_6$alkyl, halo$C_1$-$C_6$alkoxy, mono- or di-($C_1$-$C_6$alllcyl)amino or amino$C_1$-$C_6$alkyl; or $R_6$ is: taken together with $R_3$ to form a fused 6-membered heterocycloalkyl;

$R_7$ is hydrogen, halogen, hydroxy, cyano, $C_1$-$C_6$alkyl, $C_2$-$C_6$alkenyl, $C_2$-$C_6$alkynyl or $C_1$-$C_6$alkoxy;

$R_8$ is halogen, hydroxy, cyano, $C_1$-$C_6$alkyl, $C_2$-$C_6$alkenyl, $C_2$-$C_6$alkynyl or $C_1$-$C_6$alkoxy; and $R_{11}$ is halogen, hydroxy, cyano, amino, $C_1$-$C_6$alkyl, $C_2$-$C_6$alkenyl, $C_2$-$C_6$alkynyl, $C_1$-$C_6$alkoxy, $C_1$-$C_6$alkylamino, halo$C_1$-$C_6$alkyl, halo$C_1$-$C_6$alkoxy or amino$C_1$-$C_6$alkyl.

13. A compound or salt of claim 1, wherein the compound has the formula:

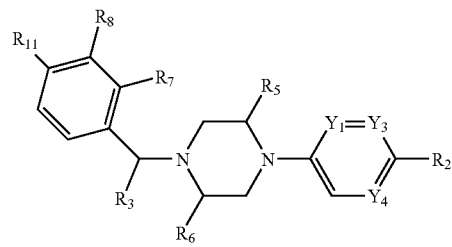

wherein:

$Y_1$ is CH or nitrogen;

$Y_3$ and $Y_4$ are independently $CR_1$ or nitrogen, such that at least one of $Y_3$ and $Y_4$ is nitrogen, and $Y_1$ is carbon if $Y_3$ is nitrogen;

each $R_1$ is independently:
(i) hydrogen, halogen, hydroxy, cyano, amino, $C_1$-$C_6$alkyl, $C_2$-$C_6$alkenyl, $C_2$-$C_6$alkynyl, $C_1$-$C_6$alkoxy, halo$C_1$-$C_6$alkyl, amino$C_1$-$C_6$alkyl or ($C_3$-$C_7$cycloalkyl)$C_0$-$C_2$alkyl; or
(ii) taken together with $R_2$ to form a fused 5- or 6-membered carbocycle or heterocycle;

$R_2$ is halogen, cyano, amino, $C_1$-$C_4$alkyl, $C_2$-$C_4$alkenyl, $C_2$-$C_4$alkynyl, $C_1$-$C_4$alkoxy, $C_{1-c4}$alkylthio, halo$C_1$-$C_4$alkyl, mono- or di-($C_1$-$C_4$alkyl)amino, ($C_3$-$C_7$cycloalkyl)$C_0$-$C_4$alkyl or (4- to 7-membere heterocycloalkyl)$C_0$-$C_4$alkyl or taken together with a $R_1$ to form a fused 5-or 6-membered carbocycle or heterocycle;

$R_3$ is: taken together with $R_6$ to form a fused 6-membered heterocycloalkyl;

$R_5$ is: (i) hydrogen, halogen, hydroxy, nitro, cyano, amino, $C_1$-$C_6$alkyl, $C_2$-$C_6$alkenyl, $C_2$-$C_6$alkynyl, $C_1$-$C_6$alkoxy, halo$C_1$-$C_6$alkyl, halo$C_1$-$C_6$alkoxy, mono- or di-($C_1$-$C_6$alkyl)amino or amino$C_1$-$C_6$alkyl; or $R_6$ is: taken together with $R_3$ to form a fused 6-membered heterocycloalkyl;

$R_7$ is hydrogen, halogen, hydroxy, cyano, $C_1$-$C_6$alkyl, $C_2$-$C_6$alkenyl, $C_2$-$C_6$alkynyl or $C_1$-$C_6$alkoxy;

$R_8$ is halogen, hydroxy, cyano, $C_1$-$C_6$alkyl, $C_2$-$C_6$alkenyl, $C_2$-$C_6$alkynyl or $C_1$-$C_6$alkoxy; and $R_{11}$ is halogen, hydroxy, cyano, amino, $C_1$-$C_6$alkyl, $C_2$-$C_6$alkenyl, $C_2$-$C_6$alkynyl, $C_1$-$C_6$alkoxy, $C_1$-$C_6$alkylamino, halo$C_1$-$C_6$alkyl, halo$C_1$-$C_6$alkoxy or amino$C_1$-$C_6$alkyl.

14. A pharmaceutical composition, comprising a compound or salt of claim 1, in combination with at least one physiologically acceptable carrier or excipient.

15. The pharmaceutical composition of claim 14, wherein the composition is formulated as an injectible fluid, an aerosol, a cream, a gel, a pill, a capsule, a syrup or a transdermal patch.

16. A packaged pharmaceutical preparation, comprising a pharmaceutical composition of claim 14 in a container; and instructions for using the composition to treat a patient suffering from a disorder associated with MCH receptor activation.

17. The packaged pharmaceutical preparation of claim 16, wherein the disorder is an eating disorder, a sexual disorder, obesity, diabetes, heart disease or stroke.

18. A method for treating obesity or diabetes type II, comprising administering to a patient in need of such treatment a therapeutically effective amount of a compound or salt of claim 1.

19. The method of claim 18, wherein the compound or salt thereof is administered orally.

20. The method of claim 18, wherein the compound or salt thereof is achninistered intranasally, intravenously or topically.

21. The method of claim 18, wherein the patient is a human.

22. The method of claim 18 wherein the patient is a dog or a cat.

23. A compound or salt of claim 12, wherein $R_7$ is not hydrogen.

24. A compound or salt of claim 23, wherein $R_8$ is $C_1$-$C_4$alkyl.

25. A compound or salt of claim 13, wherein $R_7$ is not hydrogen.

26. A compound or salt of claim 25, wherein $R_8$ is $C_1$-$C_4$alkyl.

* * * * *